United States Patent
Daniel et al.

(10) Patent No.: US 10,537,561 B2
(45) Date of Patent: Jan. 21, 2020

(54) CSF-1R INHIBITORS FOR TREATMENT OF BRAIN TUMORS

(71) Applicants: Novartis AG, Basel (CH); Sloan-Kettering Institute for Cancer Research, New York, NY (US)

(72) Inventors: Dylan Daniel, San Francisco, CA (US); Johanna Joyce, Epalinges (CH); James Sutton, Pleasanton, CA (US)

(73) Assignees: Novartis AG, Basel (CH); Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 15/996,945

(22) Filed: Jun. 4, 2018

(65) Prior Publication Data
US 2019/0030013 A1     Jan. 31, 2019

Related U.S. Application Data

(63) Continuation of application No. 14/754,152, filed on Jun. 29, 2015, now abandoned, which is a
(Continued)

(51) Int. Cl.
*A61K 31/4439*     (2006.01)
*A61K 31/175*     (2006.01)
(Continued)

(52) U.S. Cl.
CPC ........ *A61K 31/4439* (2013.01); *A61K 31/175* (2013.01); *A61K 31/4545* (2013.01);
(Continued)

(58) Field of Classification Search
None
See application file for complete search history.

(56) References Cited

U.S. PATENT DOCUMENTS 7,553,854 B2    6/2009   Sutton et al.

FOREIGN PATENT DOCUMENTS

| WO | 2007/119046 | 10/2007 |
| WO | 2007/121484 | 10/2007 |

(Continued)

OTHER PUBLICATIONS

Adamson et al. Glioblastoma multiforme: a review of where we have been and where we are going. Expert Opinion on Investigational Drugs. 18(8): 1061-1063.*
(Continued)

*Primary Examiner* — Anna Pagonakis
(74) *Attorney, Agent, or Firm* — Michelle Han

(57) ABSTRACT

The present invention provides a compound of formula I;

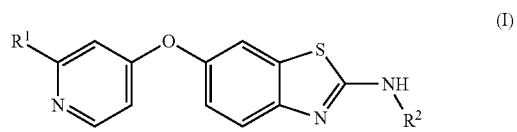

wherein $R^1$ is an alkyl pyrazole or an alkyl carboxamide, and
$R^2$ is a hydroxycycloalkyl;
or a pharmaceutically acceptable salt thereof,
and compositions containing these compounds, for use to treat a brain tumor, particularly glioblastoma. The invention provides effective treatment of a brain tumor and can be used by oral administration of a compound of Formula I as further described herein. The invention also provides a method to treat a subject having a brain tumor such as glioblastoma, wherein the method comprises administering to the subject an effective amount of a compound of Formula I. Gene signatures correlated with successful treatment using these methods are also disclosed.

8 Claims, 27 Drawing Sheets

Related U.S. Application Data continuation of application No. 14/114,878, filed as application No. PCT/US2012/036589 on May 4, 2012, now abandoned.

(60) Provisional application No. 61/624,861, filed on Apr. 16, 2012, provisional application No. 61/482,723, filed on May 5, 2011.

(51) Int. Cl.
| | | |
|---|---|---|
| *A61K 31/4545* | (2006.01) | |
| *A61K 31/675* | (2006.01) | |
| *A61K 45/06* | (2006.01) | |
| *C07D 417/12* | (2006.01) | |
| *C07D 417/14* | (2006.01) | |
| *A61K 39/395* | (2006.01) | |

(52) U.S. Cl.
CPC ........ *A61K 31/675* (2013.01); *A61K 39/3955* (2013.01); *A61K 45/06* (2013.01); *C07D 417/12* (2013.01); *C07D 417/14* (2013.01)

(56) References Cited

FOREIGN PATENT DOCUMENTS

| WO | 2007/124319 A1 | 11/2007 |
|---|---|---|
| WO | 2008/144062 | 11/2008 |

OTHER PUBLICATIONS

West et al. Cancer Research. AACR 102nd Annual Meeting 2011, Apr. 2-6, 2011.*
Komohara et al., "Possible Involvement of the M2 Anti-Inflamatory Macrophage Phenotype in Growth of Human Gliomas" Journal of Pathology 216(1):15-24, Sep. 2008.
Coniglio et al., "Microglial Stimulation of Gliobloastoma Invasion Involves Epidermal Growth Factor Receptor (EGFR) and Colony Stimulating Factor 1 Receptor (CSF-1R) Signaling" Molecular Medicine 18:519-527, 2012.
Tracey and Jefferson, "NIBR Postdoctoral Program" Sep. 21, 2010 pp. 1-2 and 40.
Dylan Daniel, Novartis Institutes for BioMedical Research, Douglas Hanahan Lab Alumni Symposium May 29, 2011.
Pyonteck et al. "CSF-1R Inhibition Alters Macrophage Polarization and Blocks Glioma Progression" Nature Medicine 19(10):1264-1272 Oct. 2013.
Motzer et al.: "Sutinib malate for the treatment of solid tumours: a review of current clinical data", Expert Opin. Investig. Drugs, 2006, 15(5): 553-561.
Pardridge, W. et al.: "The Blood-Brain Barrier: Bottleneck in Brain Drug Development", The American Society for Experimental NeuroTherapeutics, vol. 2. No. 1 (2005), pp. 3-14.
Mcnamara, M. G. et al.:"Antiangiogenic therapies in glioblastoma multiforme", Expert Rev. Anticancer Therapy, vol. 12 No. 5, pp. 643-654 (2012).
Schueneman, A. J. et al.: "SU11248 Maintenance Therapy Prevents Tumor Regrowth after Fractionated Irradiation of Murine Tumor Models", Cancer Research, vol. 63, (Jul. 2003), pp. 4009-4016.
Oberoi, R. K. et al.: "Pharmacokinetic Assessment of Efflux Transport in Sunitinib Distribution to the Brain", Journal of Pharmacol. Exp. Ther., vol. 347, pp. 755-764 (Dec. 2013).
Reardon, D. A. et al.: "Phase I study of sunitinib and irinotecan for patients with recurrent malignant glioma", J. Neuroncol, (2011), vol. 105, pp. 621-627.
Friedman et al. Temozolomide and treatment of malignant glioma. Clinical Cancer Research. vol. 6, 2585-2597, Jul. 2000.
Glioblastoma multiforme. Electronic Resource. Retrieved on Mar. 28, 2017: [http://www.cancercenter.com/brain-cancer/types/tab/glioblastoma-multiforme/].
Motzer et al. Sunitinib versus interferon alfa in life in metastatic renal-cell carcinoma. NEJM, Jan. 11, 2007; vol. 356, No. 2.

* cited by examiner

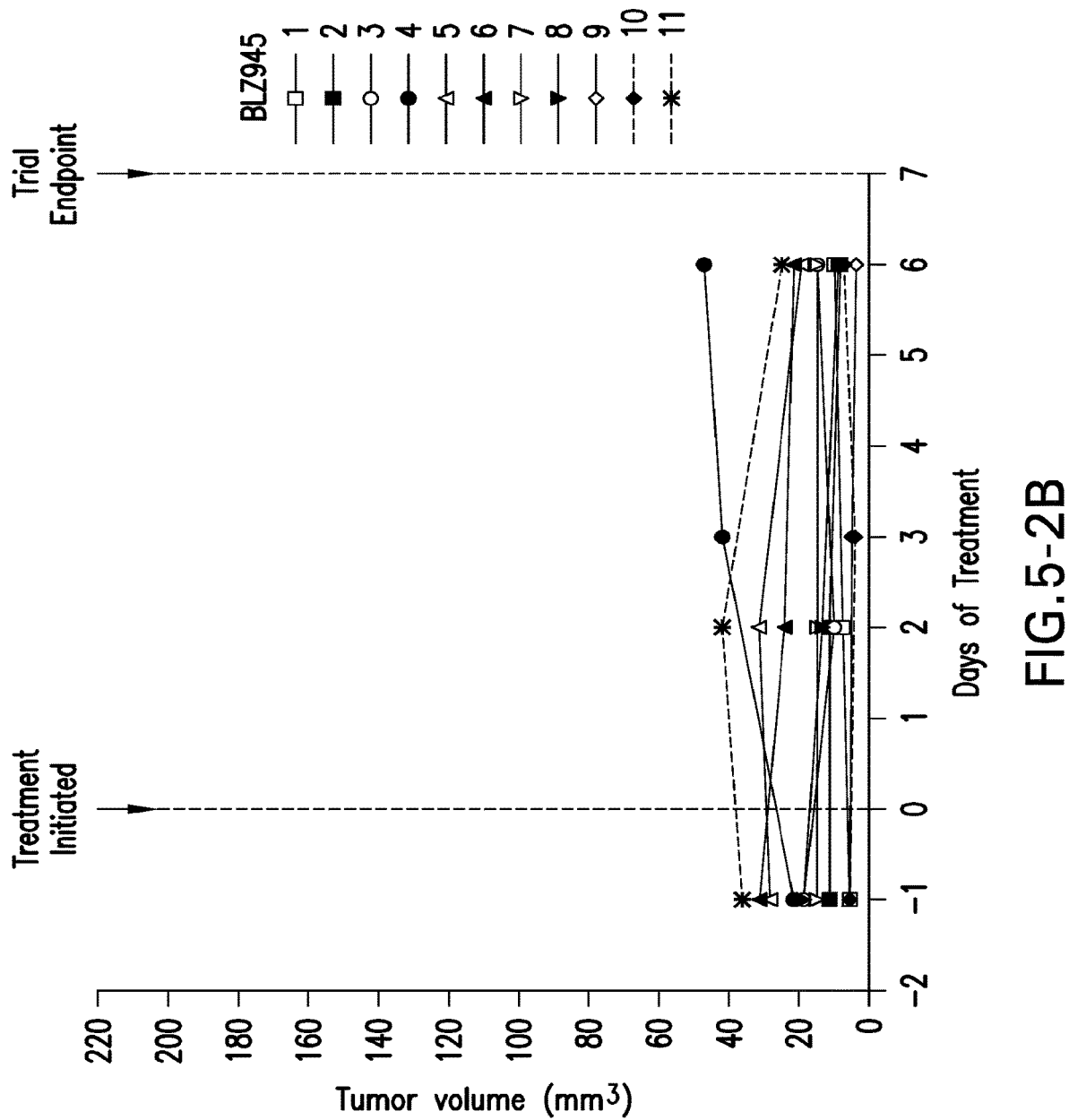

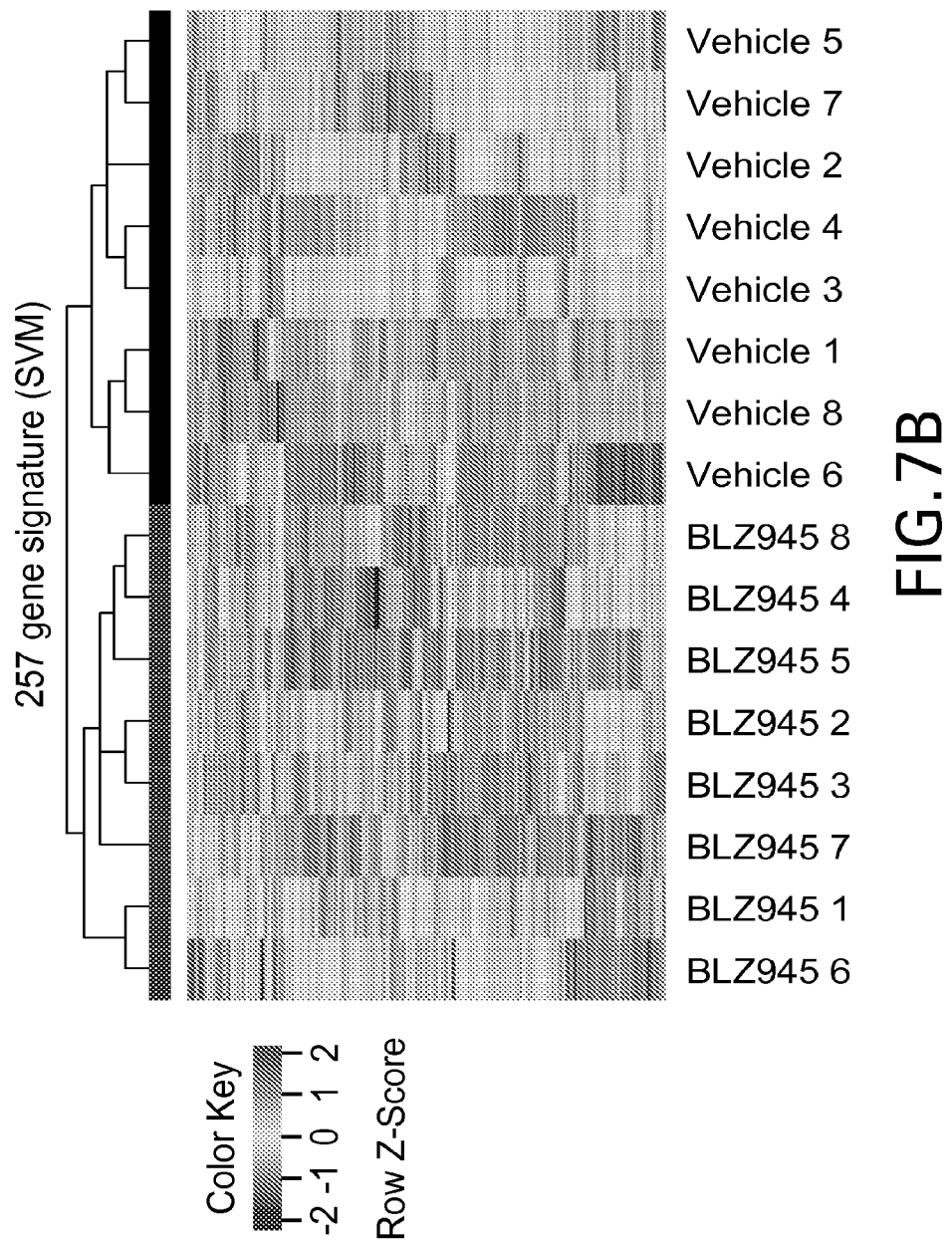

CSF-1R INHIBITORS FOR TREATMENT OF BRAIN TUMORS

BACKGROUND

Cancers of the brain and nervous system are among the most difficult to treat. Prognosis for patients with these cancers depends on the type and location of the tumor as well as its stage of development. For many types of brain cancer, average life expectancy after symptom onset may be months or a year or two. Treatment consists primarily of surgical removal and radiation therapy; chemotherapy is also used, but the range of suitable chemotherapeutic agents is limited, perhaps because most therapeutic agents do not penetrate the blood-brain barrier adequately to treat brain tumors. Using known chemotherapeutics along with surgery and radiation rarely extends survival much beyond that produced by surgery and radiation alone. Thus improved therapeutic options are needed for brain tumors.

Gliomas are a common type of brain tumor. They arise from the supportive neuronal tissue comprised of glial cells (hence the name glioma), which maintain the position and function of neurons. Gliomas are classified according to the type of glial cells they resemble: astrocytomas (including glioblastomas) resemble star-shaped astrocyte glial cells; oligodendrogliomas resemble oligodendrocyte glial cells; and ependymomas resemble ependymal glial cells that form the lining of fluid cavities in the brain. In some cases, a tumor may contain a mixture of these cell types, and would be referred to as a mixed glioma.

The typical current treatment for brain cancers is surgical removal of the majority of the tumor tissue, which may be done by invasive surgery or using biopsy or extractive methods. Gliomas tend to disseminate irregularly, though, and are very difficult to remove completely. As a result, recurrence nearly always occurs soon after tumor removal. Radiation therapy and/or chemotherapy can be used in combination with surgical removal, but these generally provide only modest extension of survival time. For example, recent statistics showed that only about half of patients in the U.S. who are diagnosed with glioblastoma are alive one year after diagnosis, and only about 25% are still alive after two years, even when treated with the current standard of care combination treatments.

Glioblastoma multiforme (GBM) is the most common adult primary brain tumor and is notorious for its lethality and lack of responsiveness to current treatment approaches. Unfortunately, there have been no substantial improvements in treatment options in recent years, and minimal improvements in the survival prospects for patients with GBM. Thus there remains an urgent need for improved treatments for cancers of the brain such as gliomas.

Gliomas develop in a complex tissue microenvironment comprised of many different types of cells in the brain parenchyma in addition to the cancer cells themselves. Tumor-associated macrophages (TAMs) are one of the prominent stromal cell types present, and often account for a substantial portion of the cells in the tumor tissues. Their origin is not certain: these TAMs may originate either from microglia, the resident macrophage population in the brain, or they may be recruited from the periphery.

TAMs can modulate tumor initiation and progression in a tissue-specific manner: they appear to suppress cancer development in some cases, but they enhance tumor progression in the majority of studies to date. Indeed, in approximately 80% of the cancers in which there is increased macrophage infiltration, the elevated TAM levels are associated with more aggressive disease and poor patient prognosis. Several studies have shown that human gliomas also exhibit a significant increase in TAM numbers, which correlates with advanced tumor grade, and TAMs are typically the predominant immune cell type in gliomas. However, the function of TAMs in gliomagenesis remains poorly understood, and it is currently not known whether targeting of these cells represents a viable therapeutic strategy. In fact, opposing effects on tumor growth have been reported in the literature, in some cases even where a similar experimental strategy was used to deplete macrophages in the same orthotopic glioma implantation model. In some studies, TNF-α or integrin β3 produced by TAMs have been implicated in the suppression of glioma growth, whereas in other reports CCL2 and MT1-MMP have been proposed as enhancers of tumor development and invasion.

Inhibition of CSF-1R signaling represents a novel, translationally relevant approach that has been used in several oncological contexts, including xenograft intratibial bone tumors. However, it has not yet been shown to be effective in brain tumors. Some non-brain cancers have been targeted with compounds that affect a variety of cell types that are associated with, or support, tumor cells rather than directly targeting the tumor cells themselves. For example, PLX3397 is reported to co-inhibit three targets (FMS, Kit, and Flt3-ITD) and to down-modulate various cell types including macrophages, microglia, osteoclasts, and mast cells. PLX3397 has been tested for treating Hodgkin's lymphoma. However, Hodgkin's lymphoma responds well to various chemotherapeutics, according to the PLX3397 literature, while brain tumors are much more resistant to chemotherapeutics and have not been successfully treated. As demonstrated herein, a CSF-1R inhibitor had no direct effect on proliferation of glioblastoma cells in culture, though, and it did not reduce numbers of macrophage cells in tumors of treated animals. It is thus surprising that, as also demonstrated herein, a CSF-1R inhibitor can effectively inhibit growth of brain tumors in vivo, cause reduction in tumor volume in advanced stage GBM, and even apparently eradicating some glioblastomas.

SUMMARY OF EMBODIMENTS OF THE INVENTION

The present invention is based on demonstrations that brain tumors, particularly glioblastoma, can be treated with an inhibitor of CSF-1R. The effectiveness of the CSF-1R inhibitors described herein is believed to be due to their inhibition of certain activities of TAMs, even though it does not appear to significantly reduce the number of TAMs present, and is likely also a function of the demonstrated ability of these compounds to penetrate the blood-brain barrier effectively in subjects with a brain tumor. These methods provide much needed new therapeutic options for patients diagnosed with brain tumors, particularly glioblastomas.

Colony stimulating factor-1 (CSF-1), also termed macrophage colony stimulating factor (M-CSF), signals through its receptor CSF-1R (also known as c-FMS) to regulate the differentiation, proliferation, recruitment and survival of macrophages. Small molecule inhibitors of CSF-1R have been developed that block receptor phosphorylation by competing for ATP binding in the active site, as for other receptor tyrosine kinase inhibitors. The present invention uses a potent, selective CSF-1R inhibitor, which penetrates the blood-brain barrier (BBB), to block CSF-1R signaling in glioma as illustrated in the RCAS-PDGF-B-HA/Nestin-Tva; Ink4a/Arf$^{-/-}$ mouse model of gliomagenesis. This genetically engineered glioma model is ideal for preclinical testing as a model for human GBM, as it recapitulates all features of human GBM in an immunocompetent setting. Because it closely models human GBM, and proneural GBM in particular, efficacy in this model is expected to translate into clinical efficacy on human glioblastomas such as glioblastoma multiforme and mixed gliomas.

The invention can be practiced with any inhibitor of CSF-1R capable of penetrating the brain. Some such compounds are the 6-O-substituted benzoxazole and benzothiazole compounds disclosed in WO2007/121484, particularly the compounds of Formula IIa and IIb in that reference, and the compounds disclosed herein.

In one aspect, the invention provides a method to treat a brain tumor in a mammalian subject, comprising administering to the subject an effective amount of a compound of Formula (I):

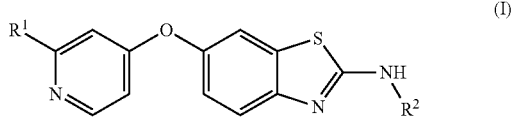

wherein R$^1$ is an alkyl pyrazole or an alkyl carboxamide; and R$^2$ is a hydroxycycloalkyl;
or a pharmaceutically acceptable salt thereof.

The method can be used to treat a patient, frequently a human subject, who has been diagnosed with a brain tumor. Further embodiments of the invention are described below.

BRIEF DESCRIPTION OF THE DRAWINGS

FIG. 5-2 shows data on tumor volume for individual animals in the control group for Example 5 (5-2A) and the treated group (5-2B), and FIG. 5-2C shows the tumor size data for the large tumor subjects treated with BLZ945 in Example 5.

FIG. 7B shows the SVM gene signature for treated and untreated animals, from which genes upregulated and downregulated by the treatment were identified.

DETAILED DESCRIPTION

Figure 1A:
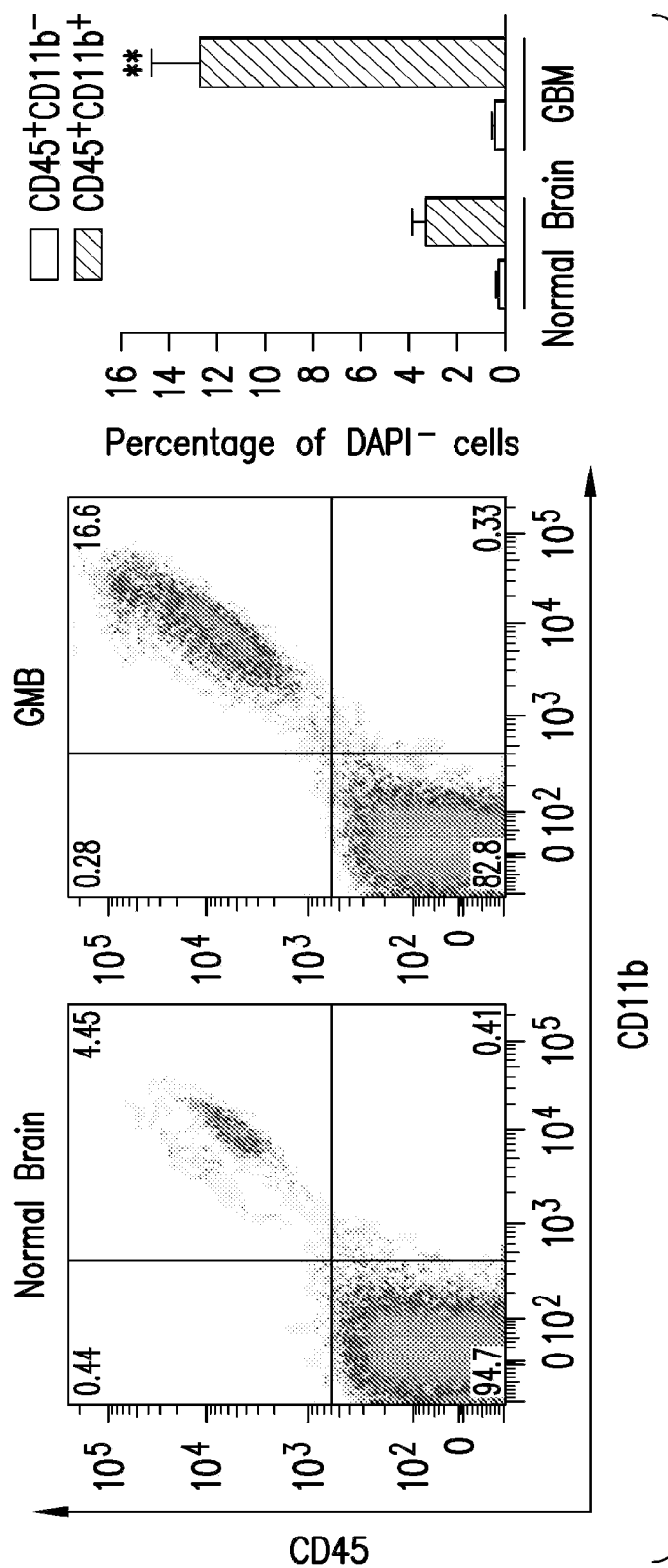
FIG. 1A is a graph showing the relative amounts of Live DAPI-positive cells in normal brain and glioblastoma tissue, as measured by the increased proportion of cells staining positive for CD45 (pan-leukocyte marker) and CD11b (myeloid cell marker) in the tumor tissue. The fluorescence activated cell sorting (FACS) data is shown, also.

The invention provides compounds of Formula (I) for use to treat brain tumors, and methods of using compounds of Formula (I) for the treatment of brain tumors. The compounds of Formula (I) have this formula:

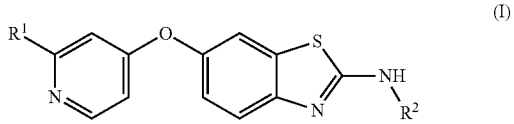

wherein R¹ is an alkyl pyrazole or an alkyl carboxamide; and

R² is a hydroxycycloalkyl;

and include pharmaceutically acceptable salts as well as neutral compounds of this formula.

Specific compounds within the scope of the invention are further described below.

The treatment of a brain tumor can include inhibition of the rate of growth of a brain tumor (slowing tumor growth), or reversal of growth of a brain tumor (i.e., reduction in tumor volume), or substantial elimination of the tumor, which has been demonstrated by the treatment herein of mice having such tumors. In particular, the treatment can slow progression or reverse progression of a glioblastoma. It may be used in conjunction with other treatments including removal of the bulk of a brain tumor, and may be used to slow or reverse regrowth or to reduce the volume or mass of residual tumorous tissue following brain tumor removal by surgical or biopsy methods. The compounds may also be used in conjunction with other chemotherapeutics.

The compounds of formula (I) include compounds wherein R¹ is an alkyl-substituted pyrazole or carboxamide, e.g., a C1-C4 alkyl pyrazole or a carboxamide of the formula —C(O)NHR, where R is a C1-C4 alkyl group. In preferred embodiments, the alkyl group is Me or Et. Certain preferred compounds for use in the invention are disclosed below. In some embodiments of these methods, R¹ is

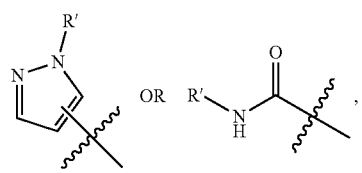

wherein R' is Me or Et. Preferably, the pyrazole ring is attached at position 4, i.e.:

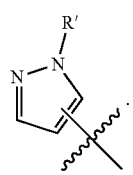

In these compounds, R² can be a hydroxycyclohexyl group such as this:

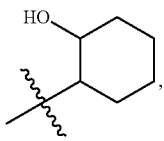

or a 2-hydroxycyclopent-1-yl group.

Specifically preferred compounds include any of the following compounds, or a mixture of any two or more of these compounds, or a pharmaceutically acceptable salt of any one of these:

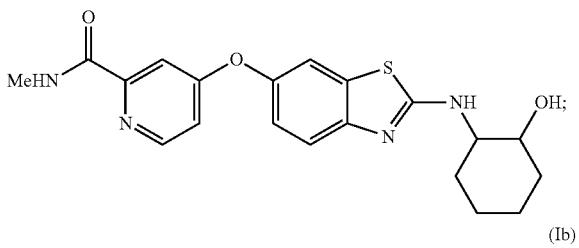
(Ia)

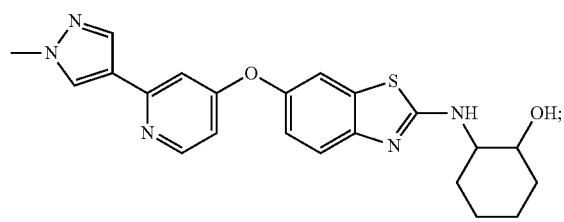
(Ib)

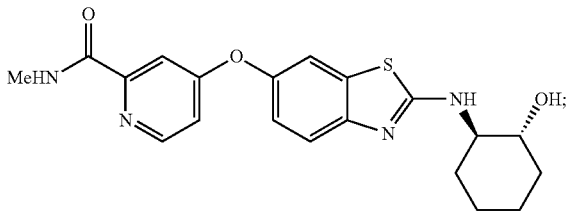
(Ic)

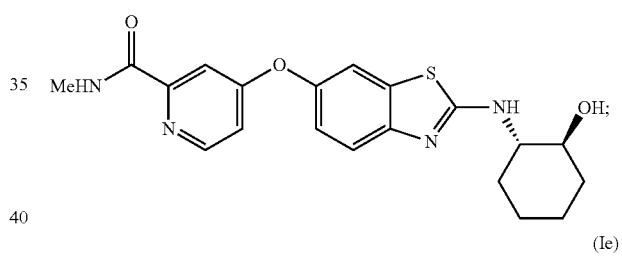
(Id)

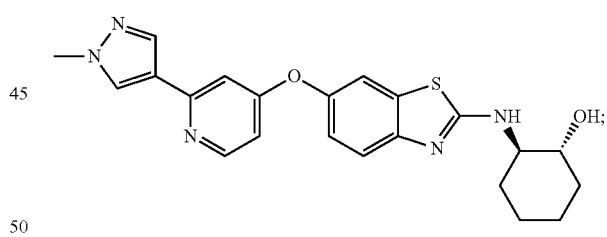
(Ie)

or

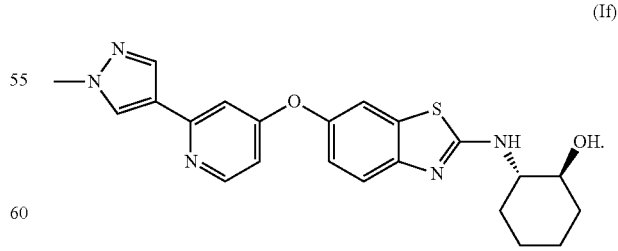
(If)

Each of these compounds and their pharmaceutically acceptable salts are preferred embodiments for purposes of the present invention. Preferred embodiments of these compounds also include compounds of these formulas:

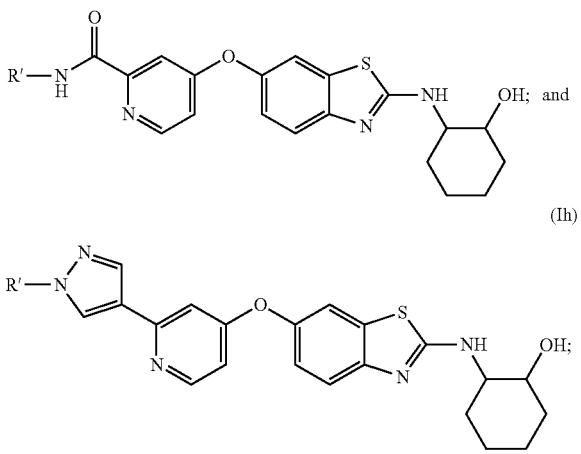

where R' is Me, Et or Propyl, preferably methyl. Specific embodiments of these compounds can be of (R,R) absolute stereochemistry or (S,S) absolute stereochemistry.

These compounds are expected to exhibit blood-brain barrier penetration like BLZ945, based on their very similar physicochemical properties, and are therefore suitable for use in the present treatment methods.

Compounds of Formula (I) are known in the art, and methods for making them are disclosed, for example, in WO2007/121484; their usefulness to treat glioma and their penetration of the blood-brain barrier were not previously known. Compound (1c) corresponds to BLZ945, which was utilized for in vitro and in vivo tests described herein.

Compounds of Formula (Ih) having the (1S,2S) stereochemstry at the cyclohexyl ring are novel. These compounds are unexpectedly good inhibitors of PDGFRβ while also inhibiting CSF-1R very effectively (see data herein). Accordingly, the novel compounds of this formula

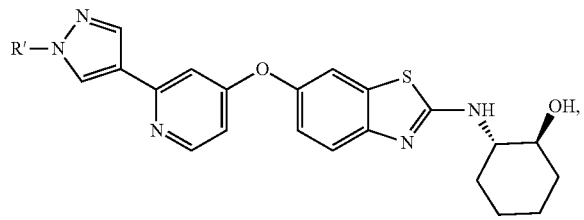

where R' is Me, Et or Propyl are another aspect of the present invention that provide a dual-inhibitor effect that is expected to increase effectiveness in the treatment methods disclosed herein.

The compounds can be used alone or they can be formulated into a pharmaceutical composition that also contains at least one pharmaceutically acceptable excipient, and often contains at least two pharmaceutically acceptable excipients. It will be understood that pharmaceutically acceptable excipients are typically sterilized. Some suitable excipients are disclosed herein; in some embodiments, the compound is formulated as a composition comprising captisol, e.g, 20% captisol.

In some embodiments, the brain tumor is selected from a brain metastasis, an astrocytoma (including glioblastoma), an oligodendroglioma, an ependymomas, and a mixed glioma. In preferred embodiments, the brain tumor is a glioma, particularly glioblastoma multiforme. In other embodiments, the brain tumor is a brain metastasis, i.e., a metastatic tumor arising from a cancer that originated elsewhere in the body.

In some embodiments, the patient is one having glioblastoma. In specific embodiments, the subject is one diagnosed with proneural glioblastoma. See Verhaak, et al., *Cancer Cell* 17(1):98-110 (2010). This subtype of glioblastoma tends to occur in younger subjects and to involve mutations of TP53, IDH1 and PDGFRA. Verhaak, et al. reported that patients with proneural glioblastoma were less responsive than other subtypes (classical, neural, mesenchymal) to the aggressive chemotherapies in use in 2010, and even suggested that such treatment may be contraindicated for these patients. The present methods are especially effective to treat proneural glioblastoma, as demonstrated by the proneural GBM animal model used herein. Specific genetic signatures found in TAMs in mice treated with BLZ945 were found to match those of human proneural glioblastoma patients who had longer than average median survival times; this correlation did not occur when compared with patients having other subtypes of glioblastoma. Thus the genetic signature information can be used to select patients for treatment with a CSF-1R inhibitor as described herein, or to assess prognosis for a subject receiving such treatments.

In some embodiments, the method is used to treat a subject before other treatment methods such as tumor removal. In other embodiments, the method is used to treat a subject in conjunction with other treatment methods such as tumor removal by either surgical or biopsy methods, or in conjunction with radiation therapy, or in conjunction with both tumor removal and radiation therapy.

Optionally, other chemotherapeutic agents can be used along with the compounds and methods disclosed above. Suitable additional chemotherapeutic agents for use in these methods are those known in the art as conventional ones for use in treating glioblastoma. Some such chemotherapeutics include antiangiogenic agents, bevacizumab with or without irinotecan, nitrosoureas such as Carmustine (BCNU), platins such as cis-platinum (cisplatin), alkylating agents such as temozolomide, tyrosine kinase inhibitors (gefitinib or erlotinib), Ukrain, and cannabinoids. These additional therapeutic agents (co-therapeutics) can be used simultaneously with the CSF-1R inhibitor as by concurrent administration, admixing the cotherapeutic with the CSF-1R inhibitor, or by sequential administration. A preferred embodiment involves use of a compound selected from those of Formula I disclosed herein, (e.g., Formula Ia, Ib, Ic, Id, Ie, If, Ig or Ih) in combination with temozolomide or a platin compound.

In addition, macrophages have been implicated in reduced therapeutic responses in breast cancer and increased revascularization in glioblastoma xenografts following radiation therapy. Since these macrophage effects reduce the efficacy of other therapies, compounds of the invention, which inhibit macrophage activities in glioblastoma in vivo, may be expected to provide a synergistic effect when used in combination with other therapeutic agents or radiation therapy.

In some embodiments, the methods described herein are practiced with a compound of Formula (Ic). In other embodiments, the methods may be practiced with a compound of Formula (I) that is not the compound of Formula (Ic), such as the other species disclosed herein.

In some embodiments, the compound of Formula (I) also inhibits at least one other target to provide enhanced antitumor effects. For example, compounds of these formulas:

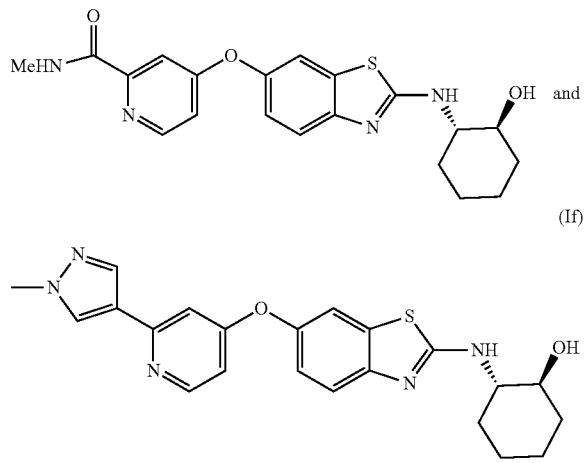

(Id)

(If)

also inhibit PDGFR at concentrations achieved in typical therapeutic dosages such as those described herein. Accordingly, these compounds can be used where a dual mechanism of action is desired, and can be used in any of the methods described above.

Exemplary compounds of Formula Ig and Ih are included in the following table to illustrate the relative activities on CSF-1R and PDGFR. Many such compounds are known in the art, see WO2007/066898, and methods to make these compounds are also well known. The compounds of Formula I are quite active on CSF-1R regardless of the stereochemistry at the cyclohexyl ring as shown in the table below. Among the various isomers, the S,S isomers are also highly active on PDGFR-β as well as on CSF-1R, and thus may act on gliomas by two mechanisms to provide enhanced efficacy.

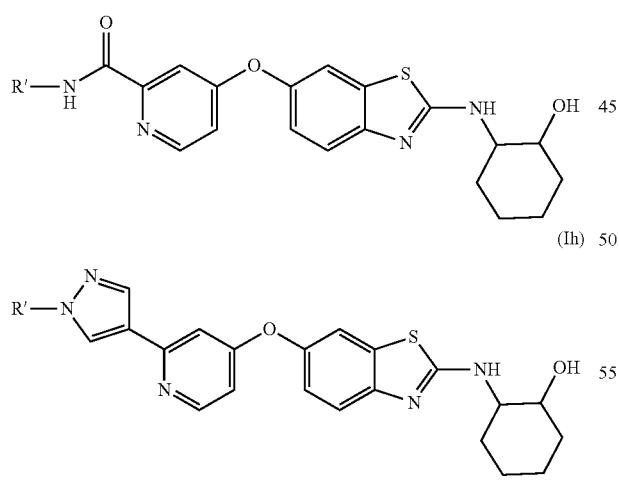

(Ig)

(Ih)

| Compound | R' | Stereochem. | CSF-1R IC-50 (μM) | PDGFR-β IC-50 (μM) |
|---|---|---|---|---|
| Ig-A | Me | (1R,2R) | 0.001 | 5.9 |
| Ig-B | Et | (1R,2R) | 0.006 μM | 13.9 |
| Ig-C | Pr | (1R,2R) | 0.008 | 7.7 |
| Ig-D | Me | (1S,2S) | 0.0008 | 0.048 |
| Ig-E | Me | (1R,2S) | 0.006 | 6.6 |
| Ig-F | Me | (1S,2R) | 0.001 | 0.78 |
| Ih-A | Me | (1R,2R) | 0.0009 | 0.74 |
| Ih-B | Et | (1R,2R) | 0.003 | 1.7 |
| Ih-C | Pr | (1R,2R) | 0.007 | 1.5 |
| Ih-D | Me | (1S,2S) | 0.001 | 0.02 |
| Ih-E | Me | (1S,2R) | 0.002 | 0.63 |

The following enumerated embodiments are representative of the invention:

1. A method to treat a brain tumor in a mammalian subject, comprising administering to the subject an effective amount of a compound of Formula (I):

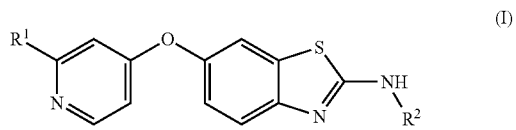

(I)

wherein $R^1$ is an alkyl pyrazole or an alkyl carboxamide; and $R^2$ is a hydroxycycloalkyl;

or a pharmaceutically acceptable salt thereof.

2. The method of embodiment 1, wherein $R^1$ is

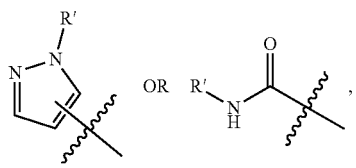

wherein R' is Me or Et.

3. The method of embodiment 1 or 2, wherein $R^2$ is

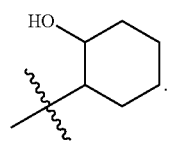 [SMILES: *C1CCCCC1O]

4. The method of any of the preceding embodiments, wherein the brain tumor is a glioma, preferably proneural glioblastoma.

5. The method of embodiment 4, wherein the glioma is glioblastoma multiforme.

6. The method of any of embodiment s 1-3, wherein the brain tumor is a brain metastasis, astrocytoma (including glioblastoma), oligodendroglioma, ependymomas, or a mixed glioma.

7. The method of any of the preceding embodiments, wherein the compound of formula (I) is

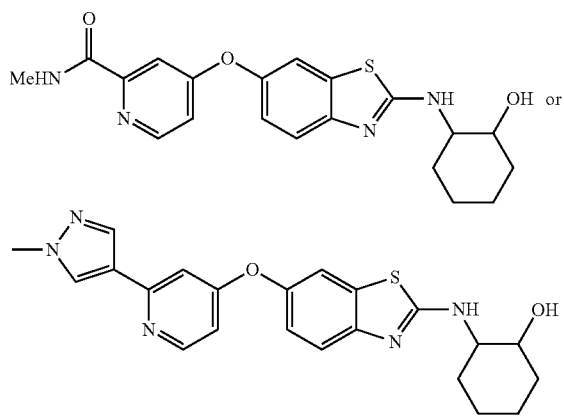

or a pharmaceutically acceptable salt thereof;
or an isolated stereoisomer of one of these.

8. The method of embodiment 7, wherein the compound of Formula (I) is:

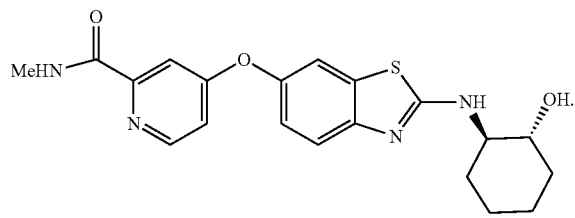 [SMILES: CNC(=O)c1cc(Oc2ccc3nc(N[C@@H]4CCCC[C@H]4O)sc3c2)ccn1]

9. The method of embodiment 7, wherein the compound of Formula (I) is:

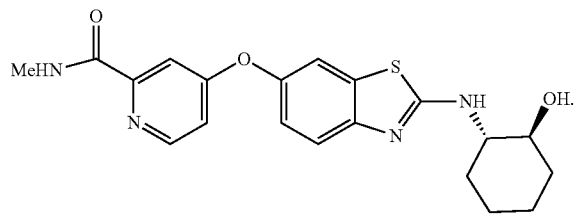 [SMILES: CNC(=O)c1cc(Oc2ccc3nc(N[C@H]4CCCC[C@@H]4O)sc3c2)ccn1]

10. The method of embodiment 7, wherein the compound of Formula (I) is:

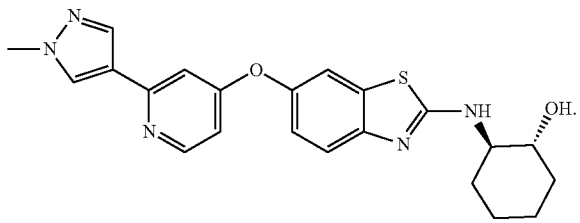 [SMILES: Cn1cc(-c2cc(Oc3ccc4nc(N[C@@H]5CCCC[C@H]5O)sc4c3)ccn2)cn1]

11. The method of embodiment 7, wherein the compound of Formula (I) is:

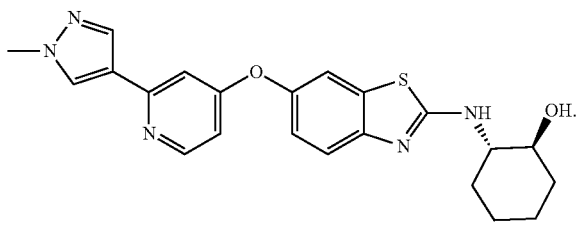 [SMILES: Cn1cc(-c2cc(Oc3ccc4nc(N[C@H]5CCCC[C@@H]5O)sc4c3)ccn2)cn1]

12. The method of any of the preceding embodiments, wherein the method further comprises administering to the subject an effective amount of an additional cancer therapeutic an antiangiogenic agents, bevacizumab with or without irinotecan, nitrosoureas such as Carmustine (BCNU), platins such as cis-platinum (cisplatin), alkylating agents such as temozolomide, tyrosine kinase inhibitors (gefitinib or erlotinib), Ukrain, and cannabinoids.

13. The method of any of the preceding embodiments, wherein the compound of Formula (I) is administered orally.

14. The method of any of the preceding embodiments, wherein the amount of the compound of Formula (I) administered to the subject is between about 50 mg/kg per day and about 500 mg/kg per day, or between 5-500 mg/kg, or between 100 and 300 mg/kg per day.

15. The method of any of the preceding embodiments, wherein the subject has proneural glioblastoma.

16. The method of any of the preceding embodiments, wherein the subject is one selected because the subject has an elevated level of PDGF or PDGFR signaling.

17. The method of any of the preceding embodiments, wherein the subject is contemporaneously treated with an inhibitor of PDGFR, or is treated with a CSF-1R inhibitor having sub-nanomolar activity as an inhibitor of PDGFR, e.g., compound (Id) or (If).

18. The method of any of the preceding embodiments, wherein the subject is a human.

19. A compound of embodiment 1 for use to treat a brain tumor.

20. The compound of embodiment 19, wherein the brain tumor is glioblastoma.

21. The compound of embodiment 20, wherein the glioblastoma is proneural glioblastoma.

22. The compound of embodiment 20, which is formulated for use with a cotherapeutic agent.

23. A compound of the formula:

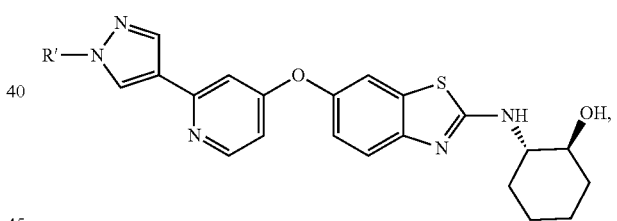

where R' is Me, Et or Propyl.

24. The compound of embodiment 23, wherein R' is Me.

25. A pharmaceutical composition comprising the compound of embodiment 23 or 24, and at least one pharmaceutically acceptable excipient.

As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be prepared by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in REMINGTON'S PHARMACEUTICAL SCIENCES, 20th ed., Mack Publishing Company, Easton, Pa., (1985); and in HANDBOOK OF PHARMACEUTICAL SALTS: PROPERTIES, SELECTION, AND USE by Stahl and Wermuth (Wiley-VCH, Weinheim, Germany, 2002).

Any formula given herein is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. In preferred embodiments, the compounds of the invention are unlabeled, i.e., they comprise approximately natural isotope abundances for all atoms. In other embodiments, the compounds of the invention are labeled by selective incorporation of an enriched non-natural isotope for one atom in the compound of Formula (I). The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art in view of the description of synthesis of the compounds of Formula I in, for example, U.S. patent publication no. US2008/0045528 (WO2007/121484). BLZ945 is described in that reference as well as several of its isomers. Examples 173 and 174 in that reference describe synthesis of pyrazole compound (Ie) using 1R,2R-aminocyclohexanol, and can be adapted for synthesis of other pyrazole compounds of Formula I, both labeled and unlabeled. The same publication at page 163 describes synthesis of both 1R,2R- and 1S,2S-aminocyclohexanol, which can readily be substituted into the method of Example 173 to produce (If) and other compounds of Formula I, both labeled and unlabeled.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

As used herein, the term "pharmaceutically acceptable excipients" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by CSF-1R, or (ii) associated with CSF-1R activity, or (iii) characterized by activity (normal or abnormal) of CSF-1R; or (2) reducing or inhibiting the activity of CSF-1R; or (3) reducing or inhibiting the expression of CSF-1R. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of CSF-1R; or at least partially reducing or inhibiting the expression of CSF-1R. The meaning of the term "a therapeutically effective amount" as illustrated in the above embodiment for CSF-1R also applies by the same means to any other relevant proteins/peptides/enzymes, such as PDGFR and the like.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In preferred embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder. In reference to a brain tumor, 'treating' typically includes either slowing rate of growth of a tumor or of regrowth of a tumor after the bulk of the tumor has been removed, or reducing the size of the tumor or of remnants of the tumor after the bulk of the tumor has been removed.

As used herein, a subject is "in need of" a treatment if such subject would benefit biologically, medically or in quality of life from such treatment. Typically the subject has been diagnosed with a brain tumor, frequently a form of glioblastoma, and preferably with glioblastoma multiforme.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

In some embodiments, the present invention utilizes a pharmaceutical composition comprising a compound of the present invention and a pharmaceutically acceptable carrier or excipient. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

In some embodiments, the pharmaceutical composition comprises at least one additional chemotherapeutic agent such as temozolomide, in an effective amount.

Typically, the pharmaceutical compositions are tablets or gelatin capsules comprising the active ingredient together with at least one excipient, such as captisol (used in the Examples herein) one of the following:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired;
d) carriers such as an aqueous vehicle containing a co-solvating material such as captisol, PEG, glycerin, cyclodextrin, or the like;
e) disintegrants, e.g., starches, agar, alginic acid or its sodium salt, or effervescent mixtures; and/or
f) absorbents, colorants, flavors and sweeteners.

Tablets may be either film coated or enteric coated according to methods known in the art.

Preferably, the compound or composition is prepared for oral administration, as a tablet or capsule, for example, or as a solution or suspension of the compound of Formula (I), optionally packaged in a single-dose container such as a capsule.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In some embodiments, the compound or composition is prepared to be administered by injection. Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

In some embodiments, the compound or composition is prepared to be administered topically. Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

In some embodiments, the effective amount of the compound of Formula (I) is between about 10 mg/kg per day, and about 500 mg/kg per day. In particular embodiments, the effective amount is between about 25 mg/kg per day and about 300 mg/kg per day, such as about 100 to about 250 mg/kg per day. The dosage may be administered in 1-4 doses per day, or it may be administered on alternating days. In a preferred embodiment, the dosage is about 200 mg/kg per day, and is administered in one or two oral doses per day.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds and methods described herein are useful to treat a variety of brain tumors, based on their demonstrated ability to penetrate the blood-brain barrier and to inhibit accumulation of TAMs in and/or around a tumor in the brain. In some embodiments, the brain tumor is a metastasis of a cancer that originated elsewhere in the body. In other embodiments, the brain tumor is a glioma such as glioblastoma multiforme.

The compounds of formula I in free form or in salt form, exhibit valuable pharmacological properties, e.g. CSF-1R and optionally PDGFR modulating properties, e.g. as indicated in in vitro and in vivo tests as provided in the next sections and are therefore indicated for therapy.

Thus, as a further embodiment, the present invention provides the use of a compound of formula (I) or in therapy. In a further embodiment, the therapy is selected from a disease which may be treated by inhibition of CSF-1R. In another embodiment, the disease is selected from the aforementioned list, suitably any brain tumor, more suitably a glioblastoma such as glioblastoma multiforme.

In another embodiment, the invention provides a method of treating a disease which is treated by inhibition of CSF-1R, comprising administration of a therapeutically acceptable amount of a compound of formula (I) or any of the embodiments of these compounds disclosed herein. In a further embodiment, the disease is selected from the aforementioned list, suitably a brain tumor, such as one of the gliomas, specifically including glioblastoma multiforme.

The pharmaceutical composition or combination of the present invention can be in unit dosage of about 1-1000 mg of active ingredient(s) fora subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to treat or inhibit the progress of the disorder or disease based on the present disclosure.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, typically 10-400 mg/kg, or between about 100-300 mg/kg, or between 1-100 mg/kg. In some embodiments, a dose of about 200 mg/kg is suitable for treatment of glioblastoma, and can be administered orally.

The activity of a compound according to the present invention can be assessed by the following in vitro & in vivo methods.

Using the test assay methods described in US20080045528, the compounds of the invention can be shown to inhibit CSF-1R. As described herein these compounds readily traverse the blood-brain barrier, and also inhibit or reverse growth of a tumor in the brain. Preferably the tumor is detectable by known methods, and progress of treatment can be monitored by known methods. In some embodiments, the progress of the treatment is monitored by using MRI (magnetic resonance imaging) to determine the size of the tumor and any metastases.

The compound of the present invention may be administered either simultaneously with, or before or after, one or more other therapeutic agents such as the cotherapeutic agents described herein. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by inhibition of CSF-1R. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above, or more than one such cotherapeutic agent.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by CSF-1R, wherein the medicament is prepared for administration with another therapeutic agent, including one of the additional chemotherapeutic agents disclosed herein as suitable for use in combination with compounds of Formula I. The invention also provides the use of another therapeutic agent for treating a disease or condition mediated by CSF-1R wherein the medicament is administered with a compound of formula (I).

The invention also provides a compound of formula (I) for use in a method of treating a disease or condition mediated by CSF-1R], wherein the compound of formula (I) is prepared for administration with another therapeutic agent. The invention also provides another therapeutic agent for use in a method of treating a disease or condition mediated by CSF-1R, wherein the other therapeutic agent is prepared for administration with a compound of formula (I). The invention also provides a compound of formula (I) for use in a method of treating a disease or condition mediated by CSF-1R wherein the compound of formula (I) is administered with another therapeutic agent. The invention also provides another therapeutic agent for use in a method of treating a disease or condition mediated by CSF-1R, wherein the other therapeutic agent is administered with a compound of formula (I).

The invention also provides the use of a compound of formula (I) for treating a disease or condition mediated by CSF-1R wherein the patient has previously (e.g. within 24 hours) been treated with another therapeutic agent. The invention also provides the use of another therapeutic agent for treating a disease or condition mediated by CSF-1R wherein the patient has previously (e.g. within 24 hours) been treated with a compound of formula (I).

In one embodiment, the other therapeutic agent is selected from an antiangiogenic agents, bevacizumab with or without irinotecan, nitrosoureas such as Carmustine (BCNU), platins such as cis-platinum (cisplatin), alkylating agents such as temozolomide, tyrosine kinase inhibitors (gefitinib or erlotinib), Ukrain, and cannabinoids. In some embodiments, the other agent is a cotherapeutic agent selected from: an antiangiogenic compound, a cannabinoid, and temozolomide.

Specific individual combinations which may provide particular treatment benefits include compound Ia, Ib, Ic, Id, Ie, If, 1g, or 1h, in combination with temozolomide. This combination may be administered orally as described herein to treat various brain tumors, such as glioblastoma multiforme.

In addition to the treatment methods, compounds and pharmaceutical composition, certain gene signature changes associated with efficacy of the CSF-1R compounds for treatment of GBM have also been identified. The Examples below provide information about these changes and identify gene signatures or biomarkers that can be used in conjunction with the treatment methods disclosed herein. As will be evident to the skilled reader, the Lasso signature and SVM signature data provided herein can be used in the determination of a prognosis for a patient treated with these methods by obtaining a sample from the patient and comparing gene expression data for the sample against the gene expression changes and signatures disclosed herein as correlating with positive prognosis and/or prolonged survival.

EXAMPLES

Compounds of the invention were prepared according to methods known in the art, particularly those described in WO2007/121484.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18-5 ⨆, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

Mass spectrometric analysis was performed on one of two LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50 V; column temperature 30° C.). All masses were reported as those of the protonated parent ions.

Analytical Data for Compound (If): HPLC retention time 1.93 min. Molecular Ion (MH+): m/z=422.1 (LC/MS RT=0.50 min).

Example 1: Macrophage Numbers are Increased in a Mouse Model of Gliomagenesis Compared to Normal Brain This example demonstrated the contribution of tumor-associated macrophages (TAMs) to gliomagenesis in the RCAS-PDGF-B-HA/Nestin-Tv-a; Ink4a/Arf$^{-/-}$ mouse model. In these mice, when tumor development is induced in adults, the vast majority of lesions that develop are high-grade glioblastoma multiforme (GBM), which histologically models human GBM. FIG. 1. (A) Cerebrum/forebrain from uninjected Nestin-Tv-a; Ink4a/Arf−/− mice (normal brain) or grade IV tumors (GBM) from symptomatic RCAS-PDGF-B-HA/Nestin-Tv-a; Ink4a/Arf−/− (PDG) mice were processed to a single cell suspension with papain for flow cytometry (n=5 each). There was a significant increase in CD45+ leukocytes from 3.6±0.6% to 13.1±2.0%. CD11b+ myeloid cells/macrophages accounted for the overwhelming majority of leukocytes (89.9-98.5% of CD45+ cells), with a 3.8-fold increase in CD45+CD11b+ cells in the tumors (12.7±2.0%) compared to normal brain (3.3±0.5%), and no differences in the populations of CD45+CD11b− cells. (B) Normal brain or GBM tissue sections from symptomatic PDG mice were immunofluorescently co-stained for CSF-1R, CD68 (macrophages), and DAPI. (C) Normal brain and GBM tumors (n=3 each) were used for RNA isolation, cDNA synthesis, and qPCR. Assays were run in triplicate and expression normalized to ubiquitin C (Ubc) for each sample. Expression is depicted relative to normal brain. (D) Normal brain or GBM tissue sections from symptomatic PDG mice were stained for CSF-1R in combination with the macrophage markers F4/80 and CD11b as well as F4/80, CD11b, and CD68 in combination with Iba-1 (macrophages/microglia). DAPI was used for the nuclear counterstain. Scale bar, 50 µm. Data are presented as mean+SEM. P values were obtained using unpaired two-tailed Student's t-test; *P<0.05; **P<0.01.

Figure 1B:
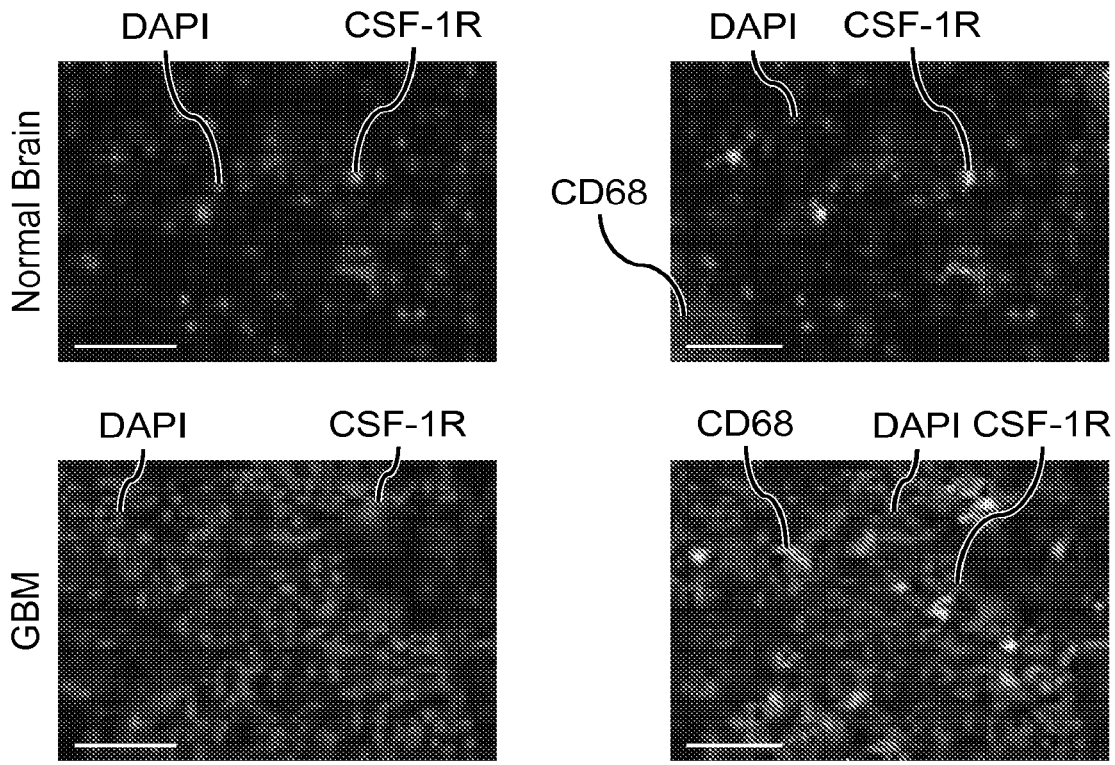
FIG. 1B depicts CD68 stained brain cells from Normal Brain tissue and from a Grade IV glioblastoma, and shows abundant macrophage infiltration in the tumor tissue. See Example 1.
Figure 1C:
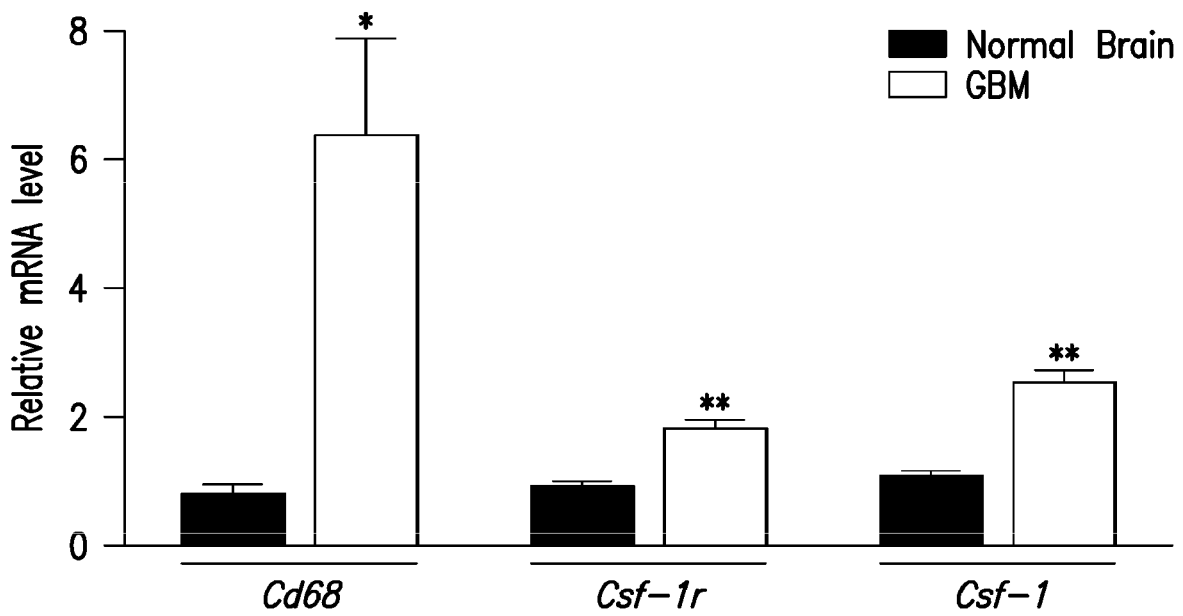
FIG. 1C depicts the increased level of mRNAs for CD68, CSF-1R and CSF-1 relative to the housekeeping gene Ubiquitin C (Ubc), for GBM tissue relative to normal brain tissue.

Numbers of macrophage cells were substantially higher in GBM tissue relative to normal brain, as shown by staining with the macrophage-specific antibody CD68 (FIG. 1B). This was confirmed by flow cytometry analysis, in which tumor-associated leukocytes (CD45$^+$) constitute 13.1% of the tumor mass, and the vast majority are macrophages (CD11b$^+$) (FIG. 1A). Expression analysis of normal brain compared to GBM revealed that the mRNA level of CSF-1 and CSF-1R, as well as CD68, increases in tumors (FIG. 1C).

Figure 1D:
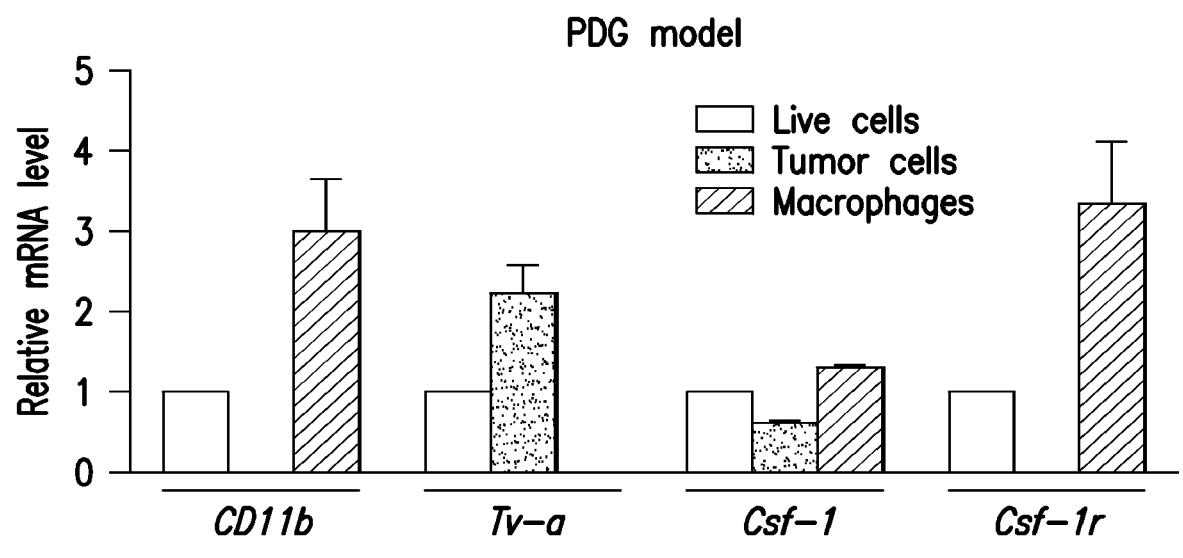
FIG. 1D shows the relative amounts of CD11b, TVA, CSF-1 and CSF-1R in TAMs relative to tumor cells.

The different cell type-specific populations were also from GBMs to determine the source of CSF-1 and its receptor. The purity of the distinct populations was confirmed by expression of the TVA receptor only in the tumor cell fraction and CD11b solely in the TAMs. While CSF-1 was expressed by both tumor cells and TAMs, CSF-1R was only expressed by TAMs (FIG. 1D). The first column in each group of three in FIG. 1D is Mixed cells, the second is FACS-purified tumor cells, and the third is FACS-purified TAMs; Mixed cells are set to 1 to normalize the data. The graphs show no CD11b expression in tumor cells and no CSF-1R expression in tumor cells, while TVA stains tumor cells only, not TAMs, and CSF-1 is present in approximately equal amounts in both tumor and TAM cells. These findings were confirmed by immunostaining, and all CSF-1R$^+$ cells were also positive for CD68 (not shown). This demonstrates that any effects on tumorigenesis following CSF-1R inhibition in this model are macrophage dependent.

Example 2: Analysis of the CSF-1R Inhibitor BLZ945: Pharmacokinetics and Cell-Based Assays BLZ945 (Compound Ic) has been disclosed as a selective c-fms (CSF-1R) kinase inhibitor for the suppression of tumor-induced osteolytic lesions in bone. BLZ945 is an ATP competitive inhibitor that inhibits CSF-1R in biochemical assays at 1 nM, and inhibits CSF-dependent cell proliferation at an IC-50 of about 67 nM. By comparison, the IC50 values for most of >200 miscellaneous kinases tested are >10 µM (10,000 nM), and for cKIT and PDGFRβ the IC-50's are 3.5 µM (3500 nM) and 5.9 µM (5900 nM) respectively. When screened against several hundred kinases in the Ambit® kinase array, the compound showed activity lower than 50% of control only against CSF-1R, PDGFRα and PDGFRβ, and the activity on the two PDGFRs was far lower than its activity on CSF-1R in direct inhibition assays. As discussed herein, compounds like BLZ945 but having the (S,S) stereochemistry exhibit activity against PDGFRβ at levels similar to their high level of activity on CSF-1R.

Figure 2:
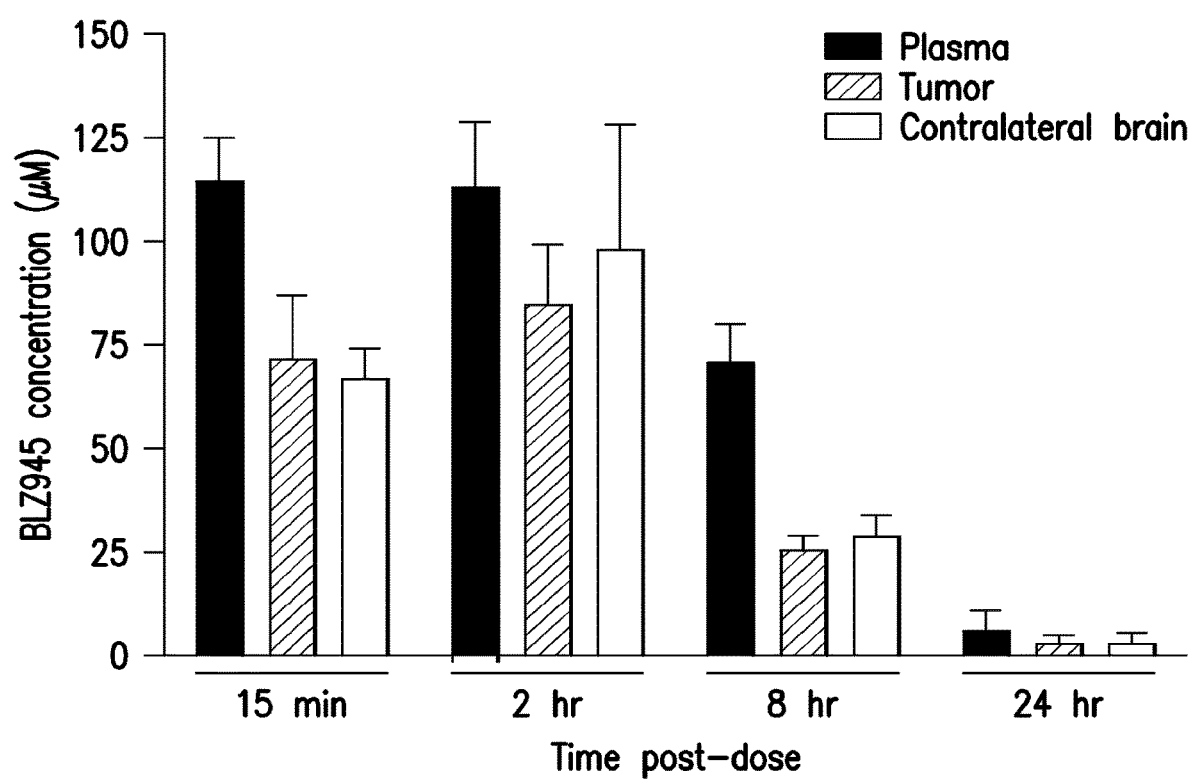
FIG. 2 depicts amounts of BLZ945 in Plasma, brain tissue from the left half of a brain containing GBM, and from the right half of the same brain with no visible GBM at several time points after treating cohorts of mice with BLZ945.

Mice having GBM detectable in only the right half of their brains were treated with BLZ945, and the concentration of compound in plasma, and in the right and left halves of the brain were then measured at various time points (15 mins, 2 hr, 8 hr, 24 hr). As FIG. 2 shows, the plasma concentration rises rapidly to a little over 100 uM and remains above 50 uM at 8 hr, then declines to a low level by 24 hr. The concentration in brain tissue follows a similar pattern: it remains a little lower than the plasma level, but rises well above 50 uM at the 15 min and 2 hr time points. This shows that BLZ945 crosses the blood-brain barrier (BBB), and that concentrations sufficient to inhibit macrophage growth and/or survival can be achieved in the brain. It also shows that the compound penetrates at similar levels into tumor-containing and tumor-free halves of the brain, suggesting that penetration may not depend on a lesion in the BBB caused by the presence of the tumor. This demonstrates sufficiently rapid penetration of the blood-brain barrier to provide therapeutically effective drug levels in the brain, well above the levels needed to effectively inhibit macrophages in culture.

Example 3: Inhibitory Activity of BLZ945 Against Different Cell Types In Vitro

Figure 3A:
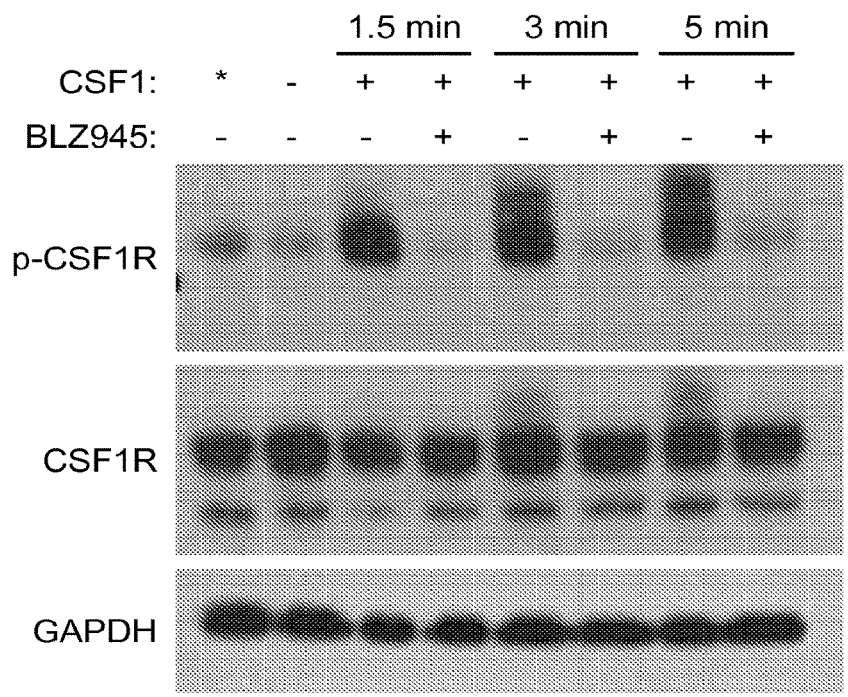
FIG. 3A shows inhibition by BLZ945 of CSF-1R phosphorylation, following CSF-1 stimulation, in bone-marrow derived macrophage cells (BMDM).

Bone marrow-derived macrophages (BMDMs) were isolated and differentiated as previously described in the literature, and were then treated with 67 nM BLZ945. BLZ945 caused a clear inhibition of CSF-1R phosphorylation following CSF-1 stimulation (FIG. 3A) at each time point (1.5 min, 3 min, 5 min).

Figure 3B:
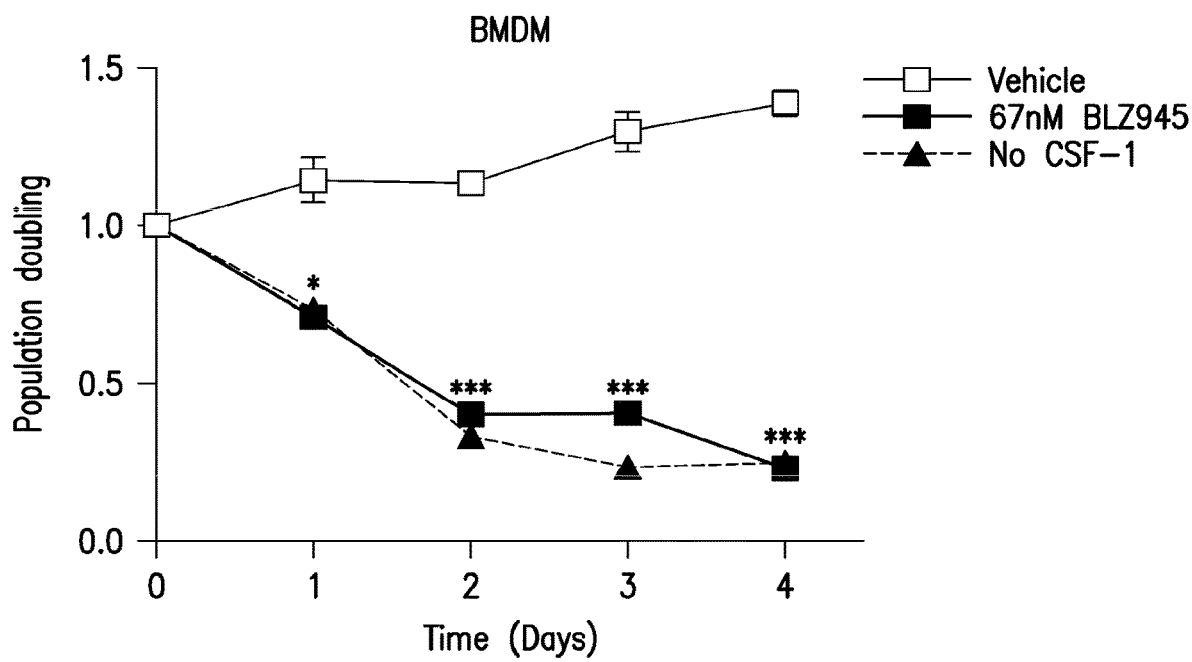
FIG. 3B shows the rate of population doubling of BMDM cells untreated, and demonstrates that treating the cells with 67 nM BLZ945 has the same effect on this rate as absence of CSF-1 stimulation.

The effects of BLZ945 on macrophages were also examined: a range of doses, from 67 nM to 6700 nM dramatically blocked macrophage survival, comparable to the effects of CSF-1 withdrawal (FIG. 3B).

Figure 3C:
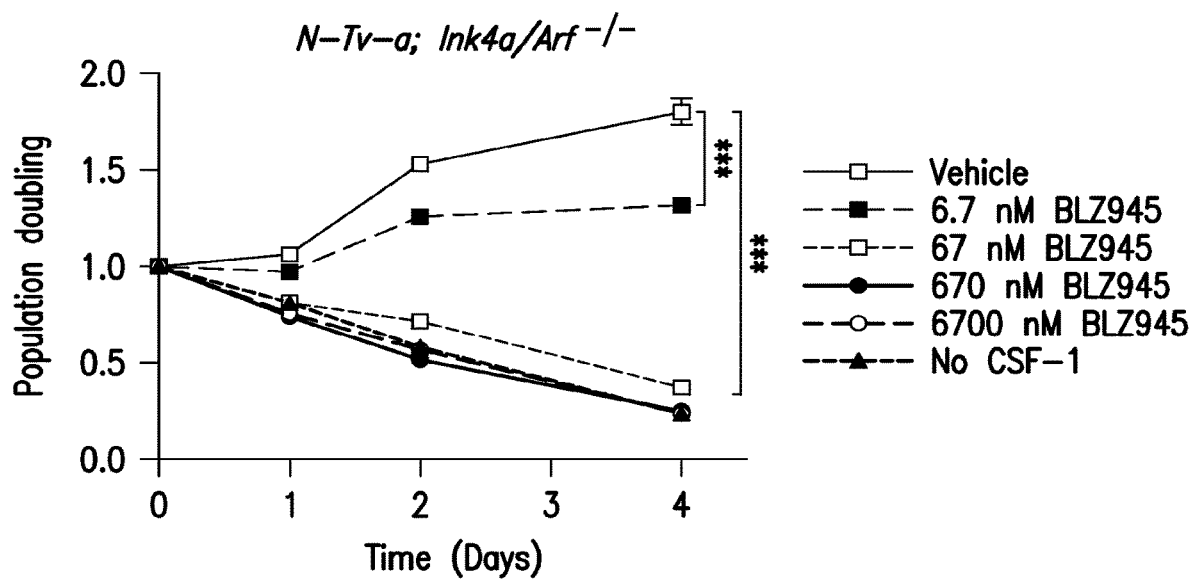
FIGS. 3C-3E show rate of proliferation of BMDM cells from the Ink4a/Arf–/– mice, of CRL-2647 normal mouse brain cells, and for two mouse GBM cell cultures.
Figure 3D:
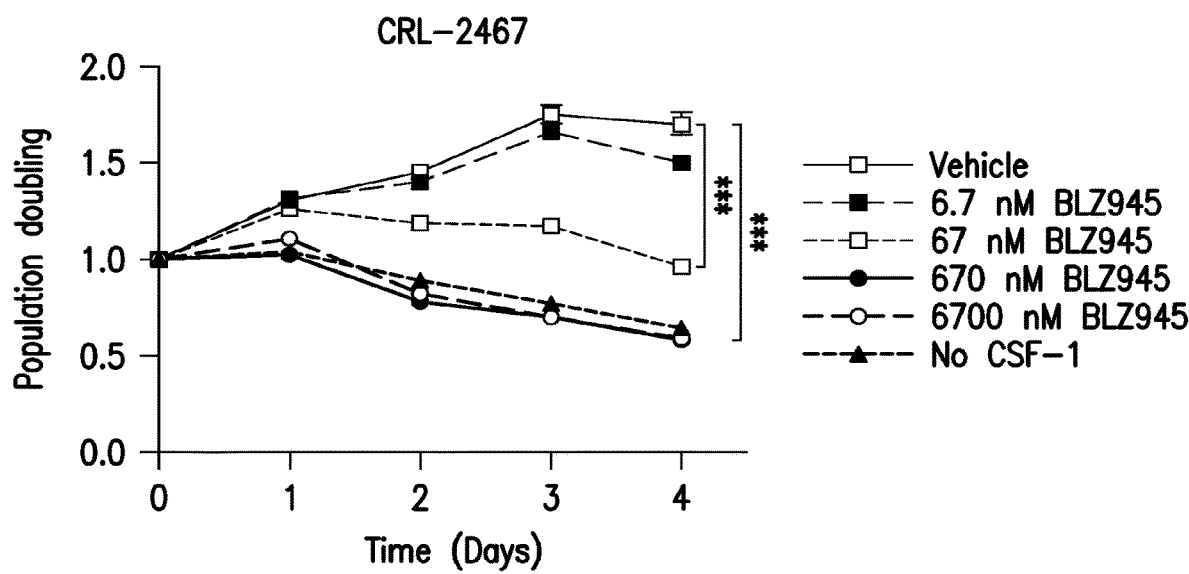
Figure 3E:
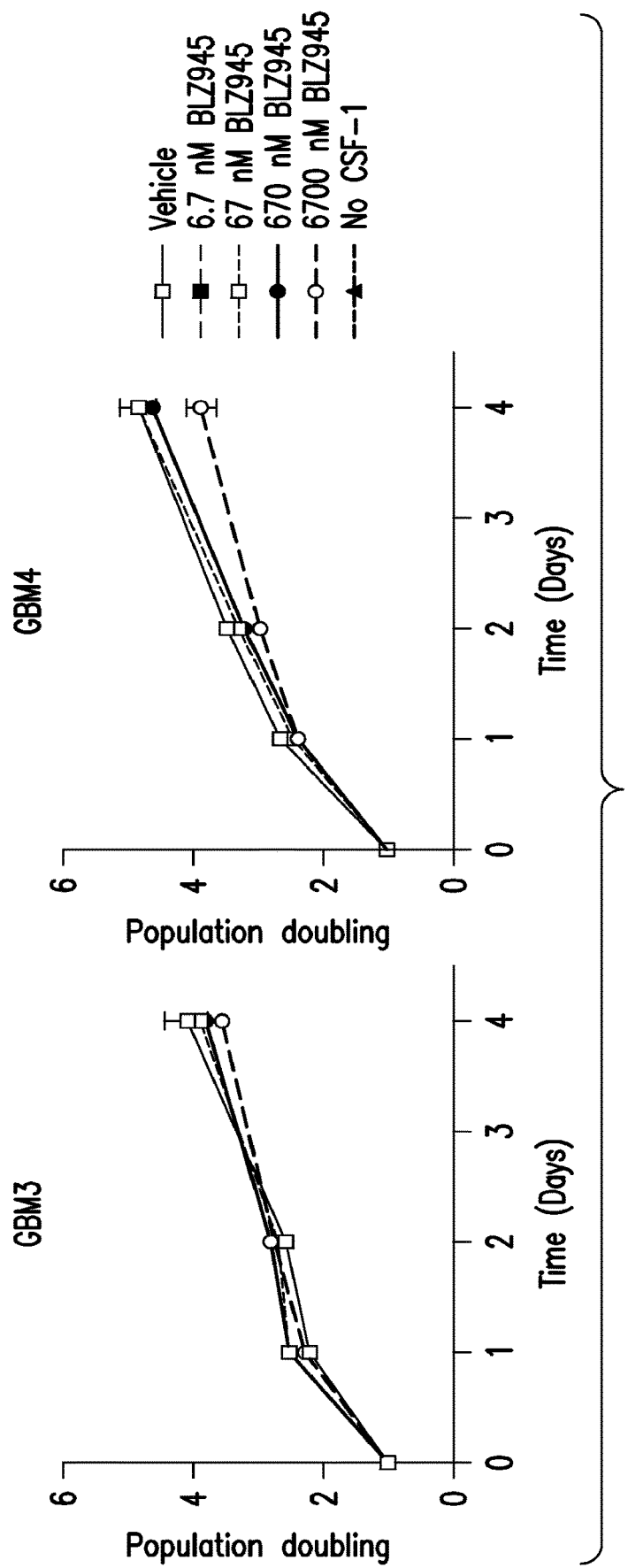
Figure 3F:
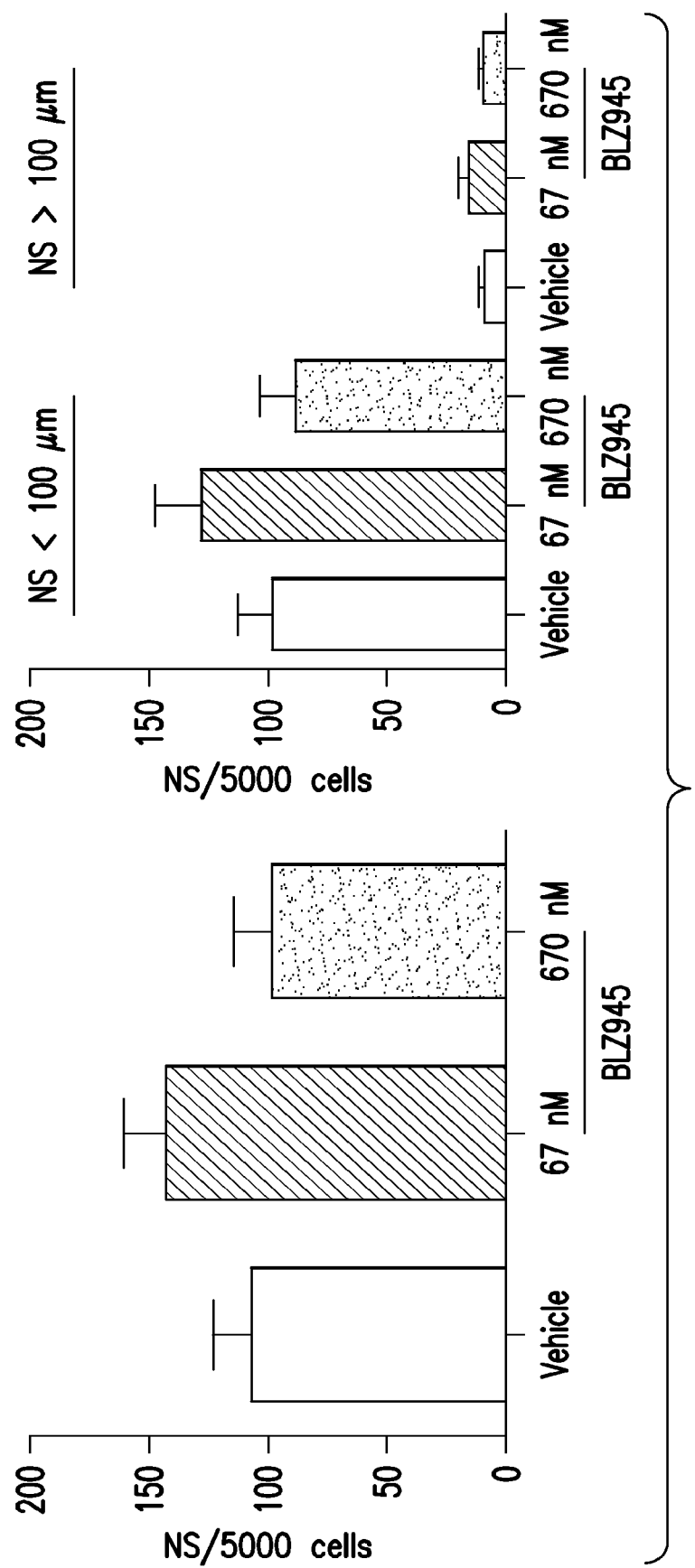
FIG. 3F shows that the total number and size of neurospheres was unaffected by BLZ945 at 670 nM.

BMDMs from Ink4a/Arf null mice (the genetic background of the GBM model), were also tested in the presence and absence of BLZ945. FIG. 3C shows that these BMDMs, like those from the wild-type mice, were substantially inhibited by concentrations of BLZ945 of 67 nM and above (FIG. 3D). Thus, BLZ945 is an effective inhibitor of CSF-1R signaling, which leads to a complete block in macrophage viability. FIGS. 3C-3E demonstrate that proliferation of BMDM cells from the Ink4a/Arf−/− mice as strongly inhibited at concentrations of BLZ945 of 67 nM and above, as were CRL-2467 cells (normal mouse brain), while even at 6700 nM it has little or no effect on proliferation of four mouse and one human glioblastoma cell cultures To determine the lack of a direct effect of BLZ945 on tumor cells, a human glioma cell line and a series of primary tumor cells and neurospheres were treated with BLZ945 at similar concentrations to those found effective against macrophage growth. U87-MG cells, derived from a human GBM, which have been shown to be dependent on PDGFR signaling in culture and in vivo, were not affected by BLZ945 treatment at the same doses as above (FIG. 3E). Similarly, the formation of secondary neurospheres from primary neurospheres (derived from mouse RCAS-PDGF-B-HA/Nestin-Tv-a; Ink4a/Arf$^{-/-}$ GBMs) was not altered by BLZ945 treatment (FIG. 3F). Neither the number nor the size of neurospheres were significantly affected by BLZ945. Finally, the effects of BLZ945 on multiple tumor cell lines that were established from secondary mouse GBM neurospheres were examined, and again, there were no differences (FIG. 3F). Collectively, these experiments demonstrate that the effects of CSF-1R inhibition by BLZ945 are specific to macrophages, with no discernible direct consequences on tumor cells.

Example 4: Treatment with the CSF-1R Inhibitor BLZ945 Blocks Glioma Progression

Figure 4A:
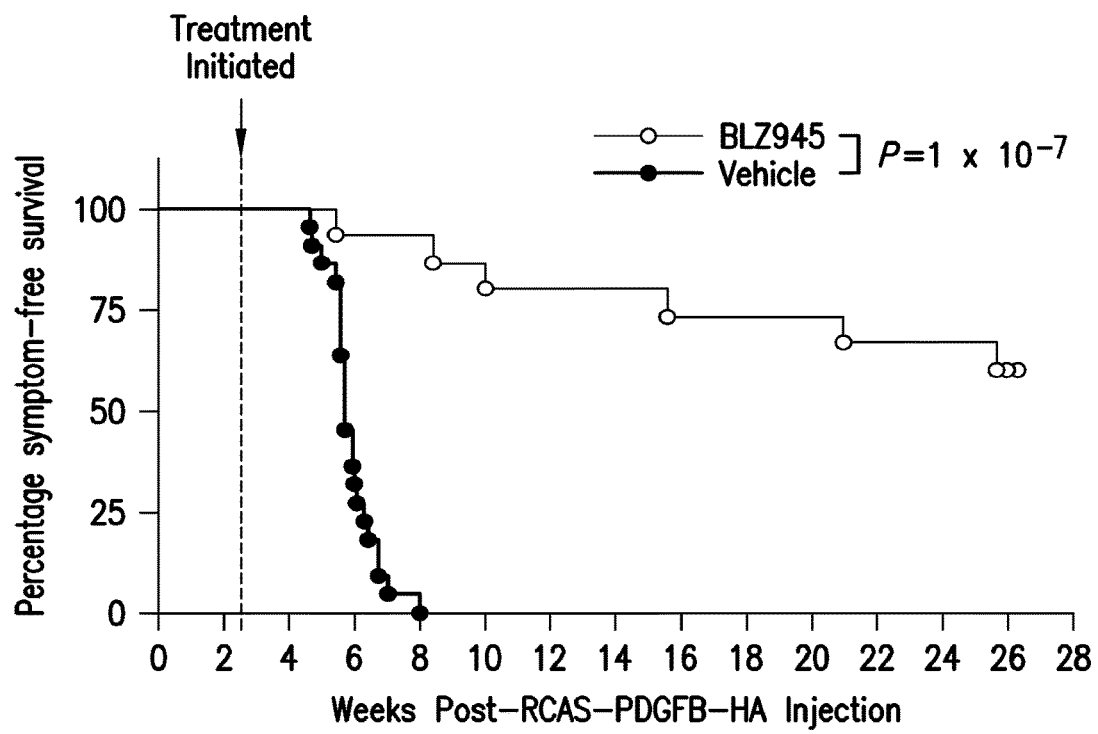
FIG. 4A depicts symptom-free survival of RCAS-PDGF-B-HA/Nestin-Tv-a; Ink4a/Arf$^{-/-}$ mice treated with vehicle alone or vehicle+BLZ945. See Example 4.

Given the potent inhibitory effects of BLZ945 in macrophage cell-based assays, and its demonstrated ability to cross the blood-brain barrier, it appeared desirable to test this inhibitor in preclinical trials in the RCAS-PDGF-B-HA/Nestin-Tv-a; Ink4a/Arf$^{-/-}$ model. These genetically engineered mice were injected at 5-6 weeks of age with RCAS-PDGF-B-HA virus-infected DF-1 cells to initiate glioma formation as described (Hambardzumyan, et al., *Transl. Oncol.*, vol. 2, 89-95 (2009)). At 2.5 weeks following tumor initiation, cohorts of mice were dosed via oral gavage daily with either 200 mg/kg BLZ945 in 20% captisol, or the vehicle (20% captisol) as a control. The mice were subsequently evaluated for symptom-free survival. The median survival in the vehicle treated cohort was 5.71 weeks (40 days), whereas 64.4% of the BLZ945 treated cohort were still alive at the trial endpoint of 26 weeks post-injection (31-32 weeks of age) (FIG. 4A, P<0.0001). This endpoint was chosen because mice in the Ink4a/Arf$^{-/-}$ background start developing spontaneous tumors, mostly lymphomas and sarcomas, around 30 weeks of age, which would complicate interpretation of the glioma phenotype in longer studies. The data in FIG. 4A shows that none of the control mice (vehicle only) were symptom free by 8 weeks after virus injection, while over half of the treated mice were symptom free at the endpoint of 26 weeks. Note: 4 treated mice were sacrificed at 12 weeks for histology studies. Of these, 3 were tumor free, and one had a grade II glioma.

Figure 4B:
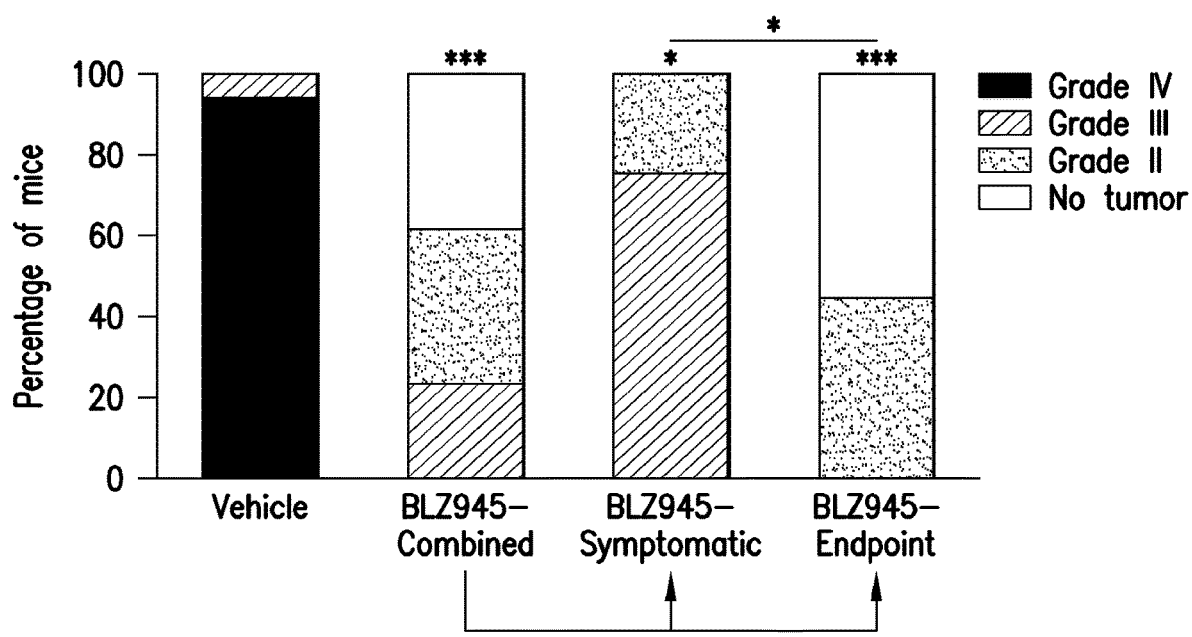
FIG. 4B depicts tumor grade for treated and untreated mice at the 26 week study endpoint. All control mice had grade III or IV tumors.

Tumor Grades were determined for the mice in both cohorts of mice (see FIG. 4B). All vehicle-treated mice at end stage had high-grade tumors, with Grade IV GBM lesions in 13 of 14 mice. In contrast, the BLZ945 treated animals had significantly less malignant tumors: 80% were either Grade II or tumor free; the remaining 20% had Grade III tumor. In 56% of the mice alive at the 26-week trial endpoint, there were no detectable lesions (FIG. 4B). Five of the BLZ945 treated mice were sacrificed as symptomatic during the trial (n=5), and compared to the group that were still asymptomatic when sacrificed at the end of the trial (n=9). In both groups, there was still a significant decrease in tumor grade compared to the vehicle-treated animals. This shows a dramatic increase in survival and reduction in tumor malignancy in this long-term trial with BLZ945 treatment.

Example 5: MRI Imaging to Monitor Effects of BLZ945 on Tumor Growth

Figure 5A:
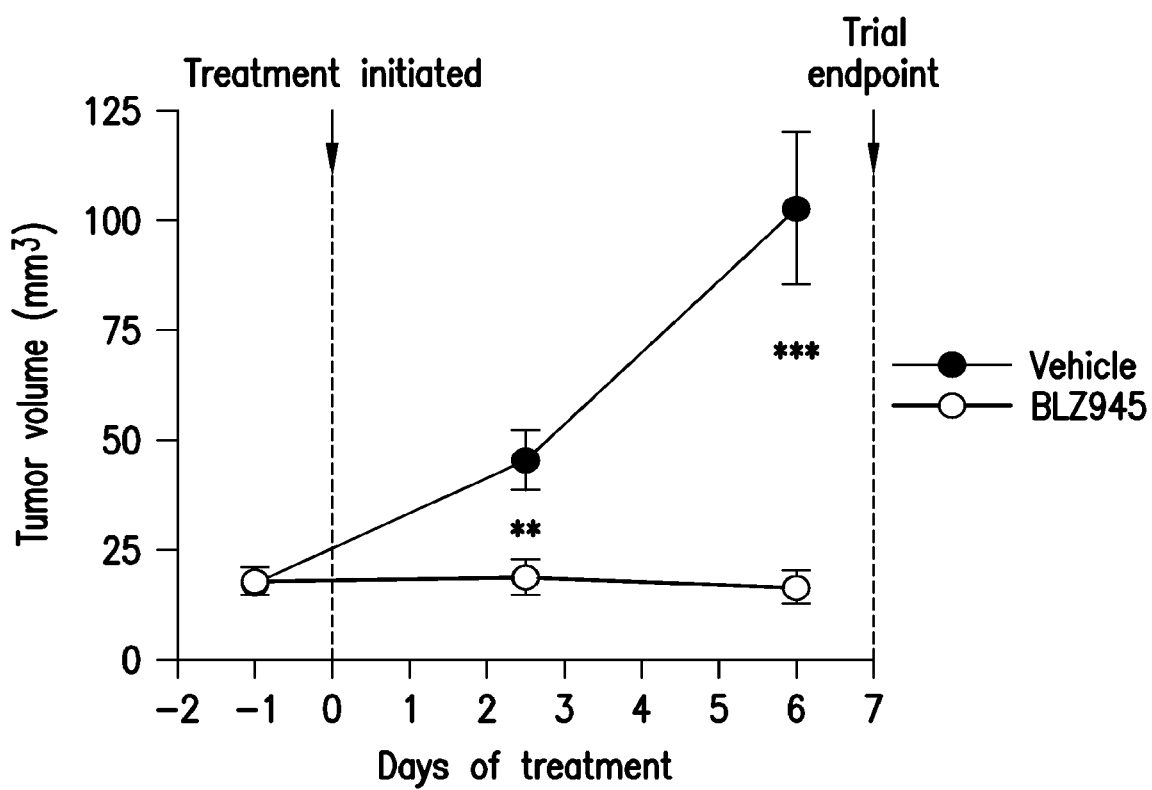
FIG. 5A shows tumor size data measured by MRI for treated and control anmals during the first 6 days of treatment with BLZ945.
Figure 5B:
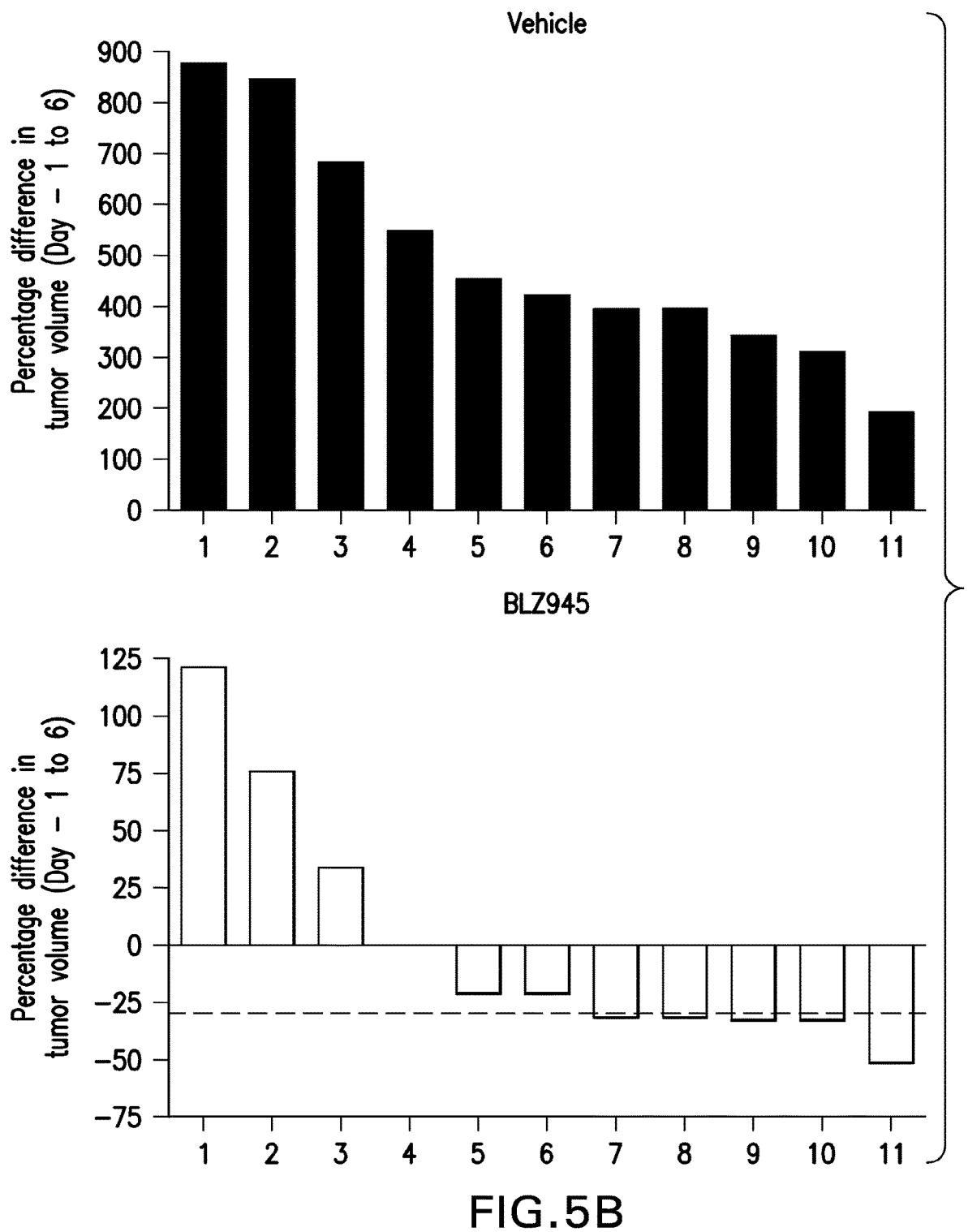
FIG. 5B shows tumor volume for individual control mice (upper graph) and treated mice (lower graph) during the first 6 days after dosing with BLZ945 started.
Figure 5C:
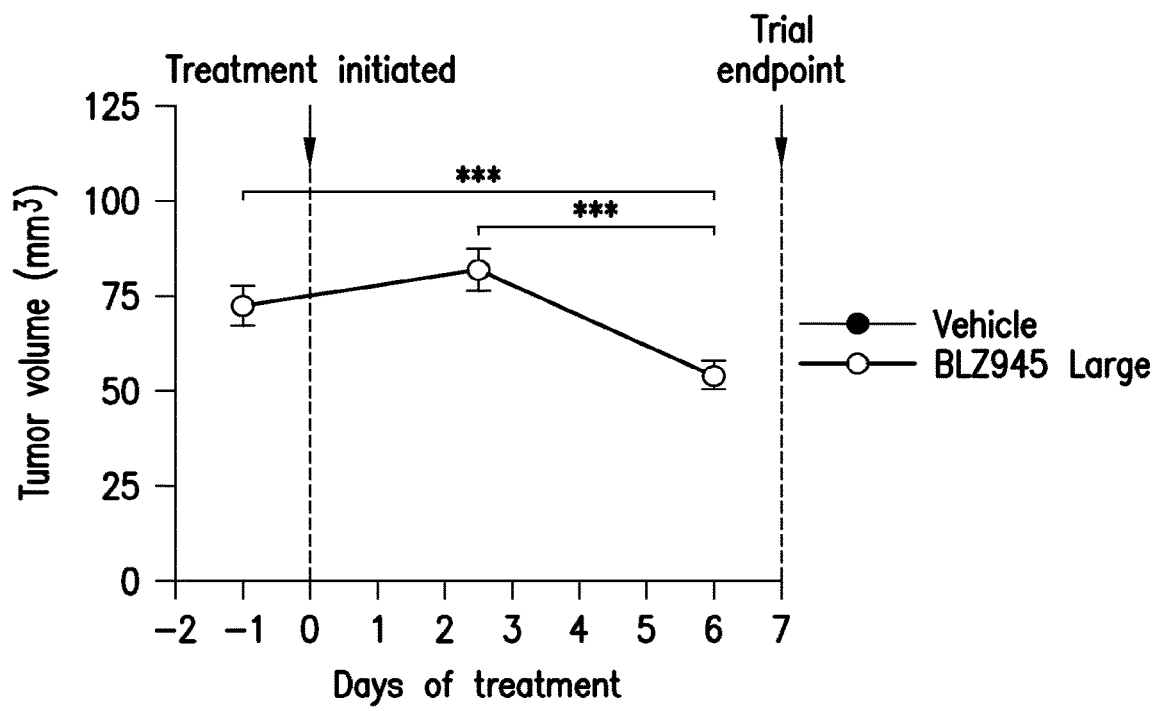
FIGS. 5C and 5D depict tumor volume measured by MRI in BLZ945-treated animals beginning with large tumors (volume >40 mm$^3$), and shows that even with large tumors, tumor volume decreased in nearly all subjects.

A short-term, 7 day trial of BLZ945 in tumor-induced mice was monitored by regular MRI scans to measure tumor size changes during a short treatment period when tumor growth is normally rapid. Tumor volume in the RCAS-PDGF-B-HA/Nestin-Tv-a; Ink4a/Arf$^{-/-}$ mice was determined by MRI, and mice were added to the trial when this was at least 4.5 mm$^3$ or greater. Mice were treated with BLZ945 or the vehicle control for 7 days, as described above. MRI scans were performed on the day before treatment was initiated, at the mid-point of the treatment, and at the day before the end of the trial period. Vehicle-treated mice showed a progressive, dramatic increase in tumor volume over this short trial, as shown in FIG. 5A, with the average tumor volume increasing about 5-fold. BLZ945 treatment blocked tumor progression as determined by MRI (FIG. 5A), with no increase in tumor size over the same short period. Treated subjects, (lower line) showed little or no tumor enlargement, while tumor volume increased sharply in the vehicle-treated controls. FIG. 5B shows tumor volume for individual control mice (upper graph) and treated mice (lower graph) during the first 6 days after dosing with BLZ945 started. Nearly all of the BLZ945 treated animals show little or no increase in tumor size, while all of the control animals show large increases in tumor volume.

Figure 5D:
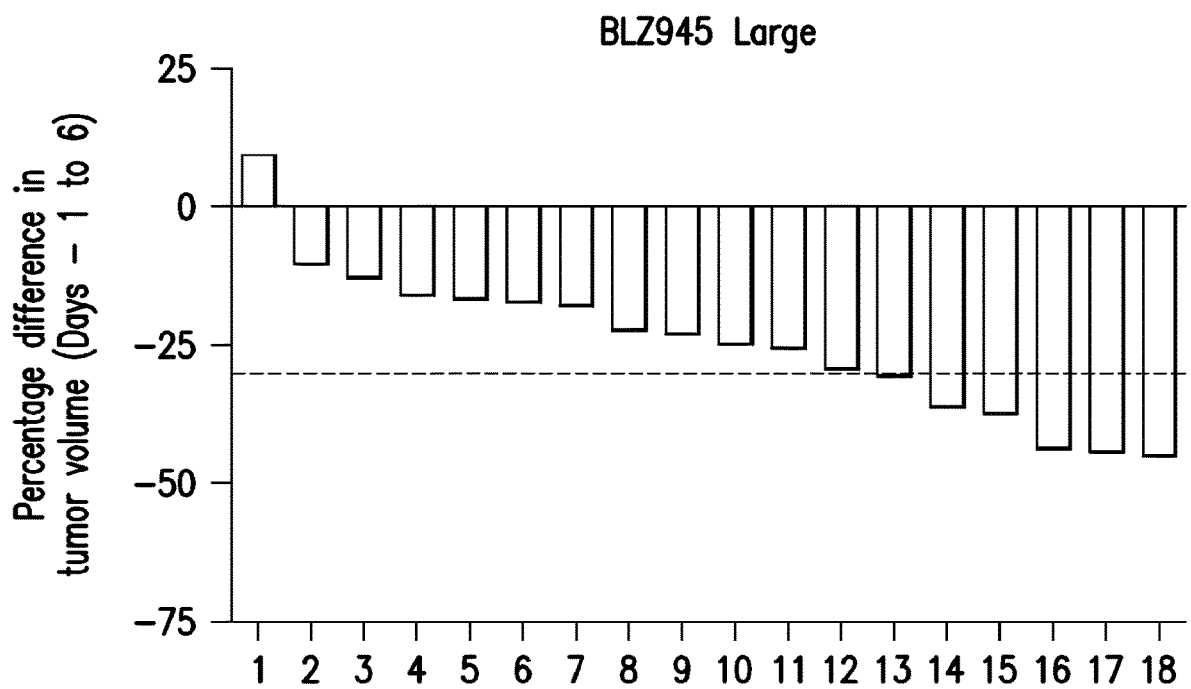
Figures 2A, 5:
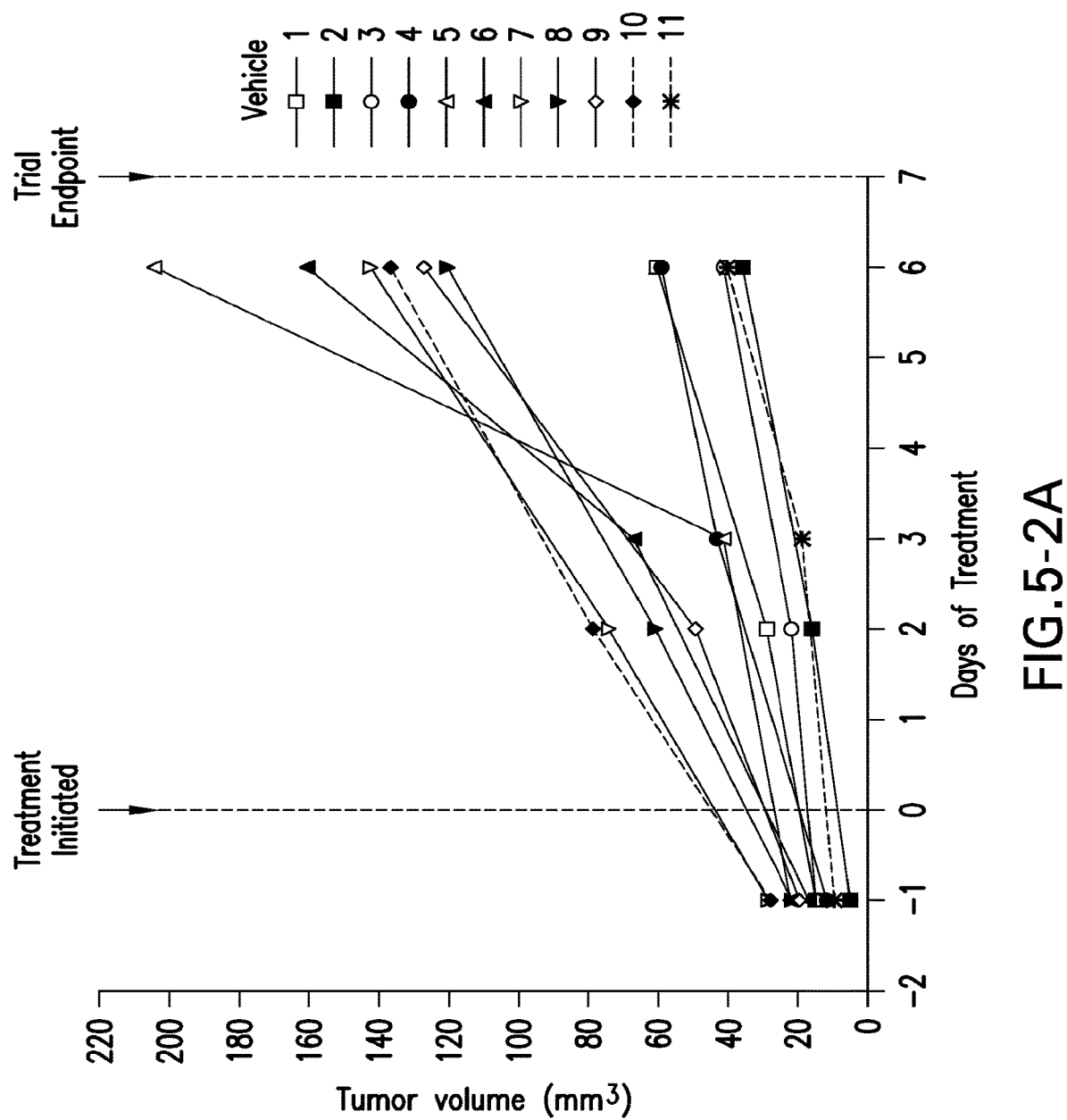

As shown in FIG. 5B, untreated tumors increased by about 150-850% in volume during this time, while tumor size was reduced in 7 of 11 treated animals and only two of the treated animals had tumor volume increases over 50%. FIGS. 5-2A and 5-2B depict the tumor volume data for all 11 test and control animals, and show that treatment largely stopped tumor size increases, while untreated tumors grew substantially in the 6-day treatment. These results indicate that CSF-1R signaling, and the presumed contribution of CSF-1R-dependent macrophages, is critical for glioma progression in this mouse model, and that BLZ945 can prevent growth of a brain tumor in a highly relevant mammalian model for human glioblastoma.

Figures 2C, 5:
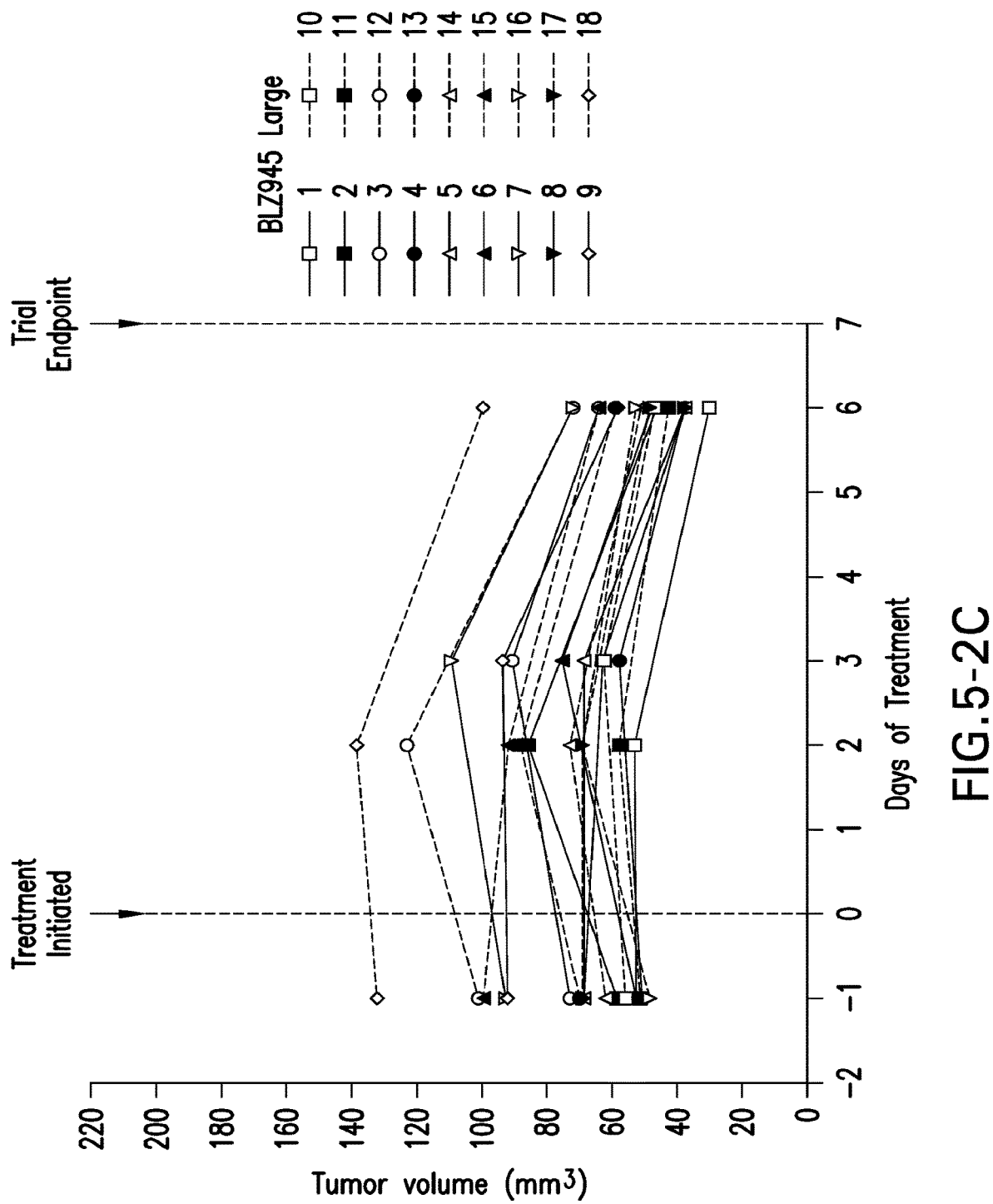

In a second in vivo test on larger tumors in the same GBM model ("large tumor" cohort), mice with tumor volumes of 48.7 to 132 mm$^3$ were treated with BLZ945, and changes in tumor volume were monitored by MRI over a span of 6 days. Tumor volume actually decreased in nearly all test animals, and 6 of 18 treated mice had a reduction of at least 30% in tumor size (FIGS. 5D and 5-2C). Control animals were not included in this test, because they would not have been expected to survive to the endpoint.

Figure 6A:
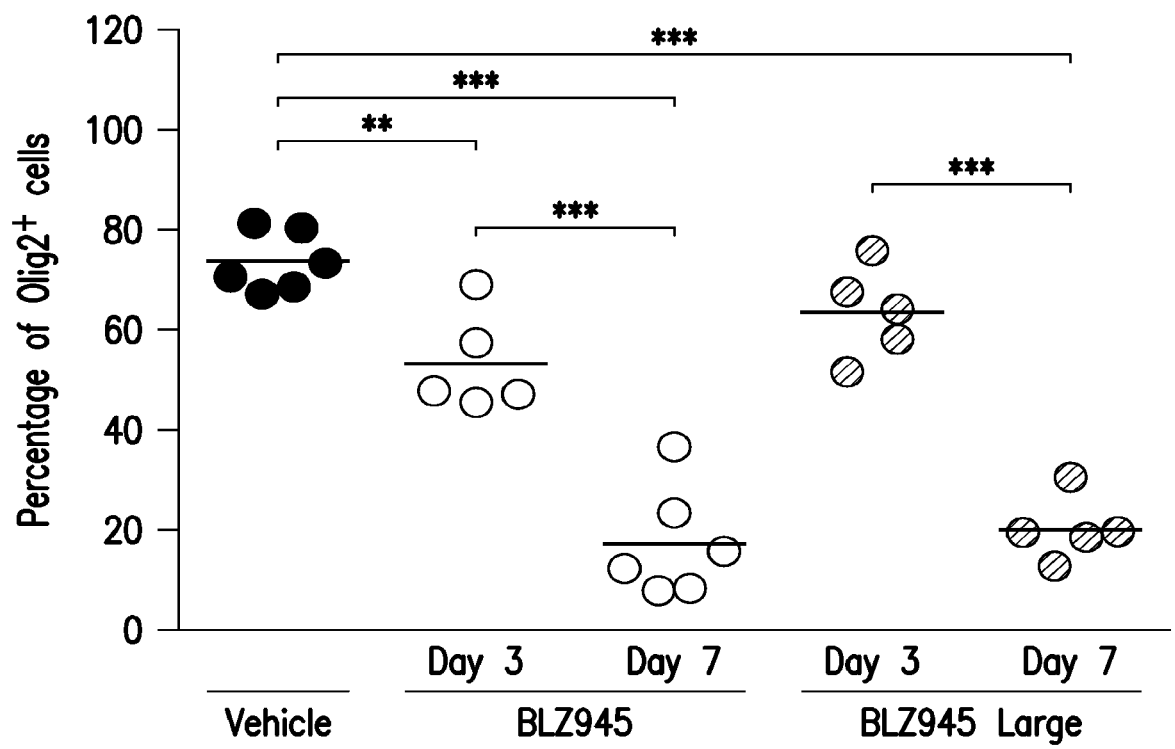
FIG. 6A-6C: the first graph shows the percentage of Olig2+ cells in the brains of animals in the vehicle, treated, and 'Large tumor' groups in Example 5. The second graph shows the fraction of tumor cells that were actively dividing, as measured by bromodeoxyuridine (BrdU) labeling. The third graph shows the level of apoptosis in the tumor cells, as measured by cleaved caspase 3 (CC3) staining, and demonstrates that BLZ945 promotes apoptosis of tumor cells.

Example 6: Analysis of Hallmark Capabilities of Cancer in BLZ945 Treated Tumors The identification of a striking effect of CSF-1R inhibition on gliomagenesis led us to investigate the underlying mechanisms for this response and determine how BLZ945 treatment affected several of the hallmark capabilities of cancer. The analyses were performed on tissues from the short-term trial (see Example 5), so that tumors from the different treatment groups could be compared at the same defined endpoint. Tumor cell density was examined using the oligodendrocyte marker Olig2, which has previously been used to identify glioma cells. Olig2 was significantly reduced in the BLZ945 treated group compared to the vehicle controls, showing that BLZ945 significantly reduced numbers of tumor cells. (FIG. 6A).

Figure 6B:
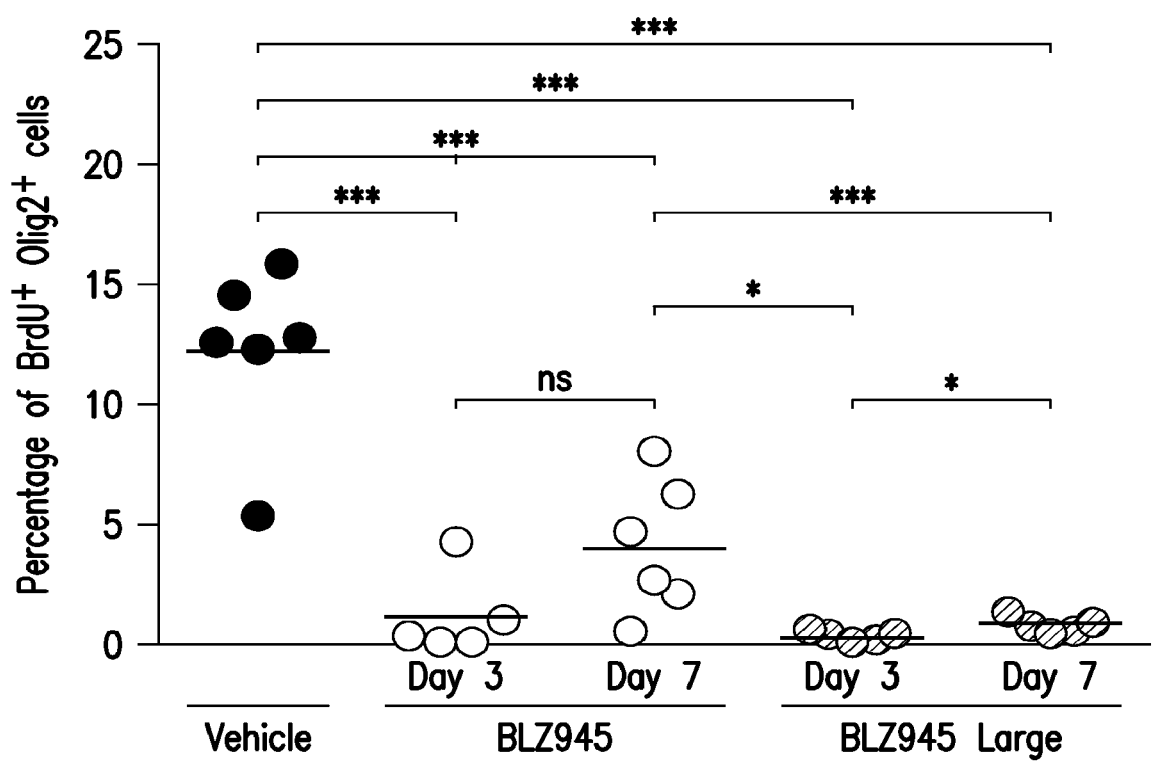

Analysis of the proportion of Olig2+ cells that were proliferating, as determined by bromodeoxyuridine (BrdU) incorporation, revealed a significant reduction in the BLZ945 group (FIG. 6B). Again, BLZ945 significantly reduced proliferation of tumor cells.

Figure 6C:
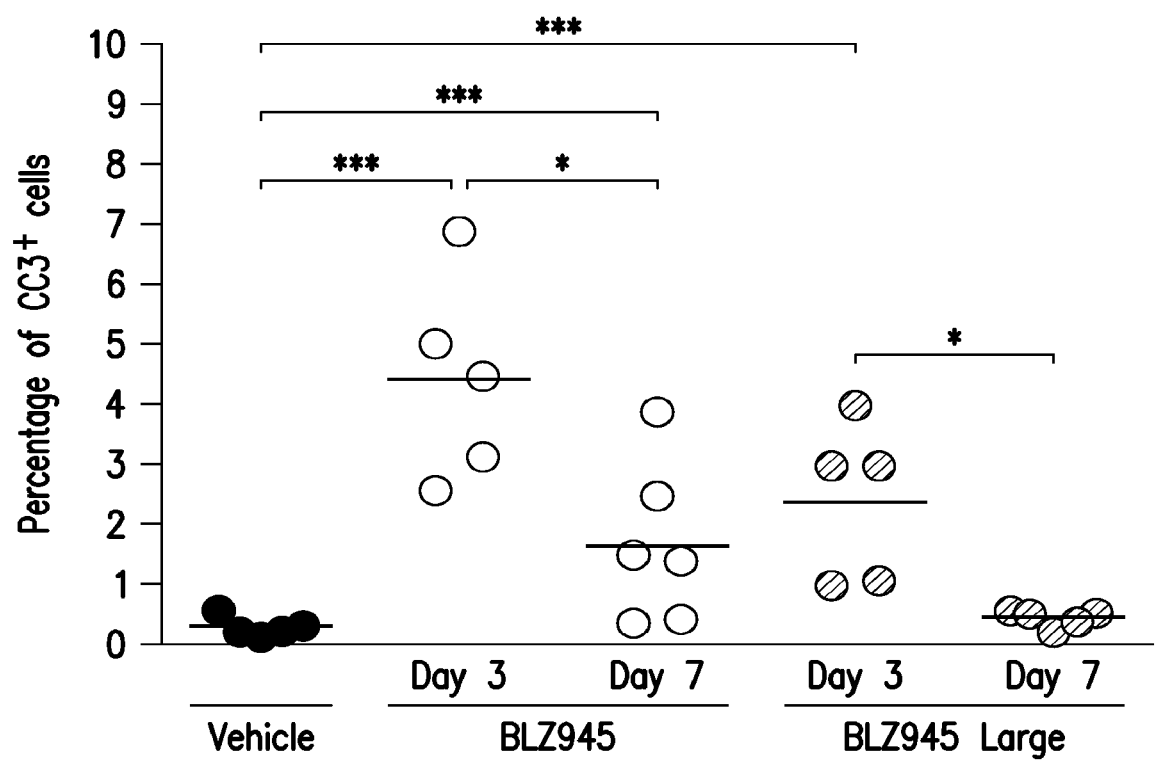

The level of apoptosis in these cells was assessed, also. Apoptotic cells were counted as those that had cytoplasmic cleaved caspase-3 (CC3)+ staining and condensed nuclei. As shown in FIG. 6C, the CSF-1R inhibitor treatment caused an increase in apoptosis at the earlier time point in particular, although little staining was observed in the Day 7 large tumor cohort.

The following table summarizes the histological analyses performed on the samples from Example 5:

TABLE 1

Histologic analyses.

| Parameter | Vehicle | BLZ945, Day 3 | BLZ945, Day 7 | BLZ945 Large, Day 3 | BLZ945 Large, Day 7 |
|---|---|---|---|---|---|
| Tumor Volume (Day −1 vs Day 6) | +498% | — | +0.68% | — | −24.3% |
| Total DAPI$^+$ Cells | — | −72% | −80% | −40% | −65% |
| Tumor Cells (% Olig2$^+$) | — | −27% | −77% | −14% | −73% |
| Proliferation (% BrdU$^+$Olig2$^+$) | — | −91% | −67% | −98% | −94% |
| Apoptosis (% CC3$^+$) | — | +17-fold | +6-fold | +9-fold | +2-fold |
| Vasculature (CD31 MVD) | — | — | −17% | — | −67% |
| Macrophages (% CD68$^+$) | — | +3-fold | +2-fold | +2-fold | +4-fold |
| Phagocytic Index | — | +2.6-fold | +3.0-fold | +2.2-fold | +4.1-fold |
| Phagocytic Capacity | — | +11.5-fold | +5.0-fold | +7.1-fold | +6.0-fold |

Tumor volume change is volume at endpoint (day 6) relative to day one, and the reported changes are relative to the control (vehicle) group.

Together, these analyses demonstrate that inhibition of CSF-1R signaling effectively blocks the growth and malignancy of gliomas through a combined effect on reducing tumor cell proliferation and increasing cell death.

In summary, these data demonstrate that the CSF-1R inhibitor BLZ945 is a potent new therapy that blocks tumor progression in a very aggressive glioma model in mice. The compound dramatically enhanced survival in a preclinical mouse model of gliomagenesis, and sharply reduced tumor growth rates and also reduced tumor size over a short and longer test period. In the long term test, BLZ945 appears to eliminate visible tumors in significant numbers of mice, and sharply reduces the tumor grade in most of the treated mice.

Since increased macrophage infiltration has been shown to correlate with malignancy in human gliomas, the potency of BLZ945 in this mouse model, apparently due to therapeutic targeting of TAMs in subjects with GBM, is expected to translate into efficacy against glioblastoma in other mammals, including humans. Since myeloid cells, including macrophages, have been implicated in blunting chemotherapeutic response in breast cancer models and in enhancing the adaptive response following irradiation in GBM xenograft models, this and similar CSF-1R inhibitors may be effective in combination with therapies directed against the cancer cells in gliomas, a possibility that merits further investigation. In particular, compounds such as

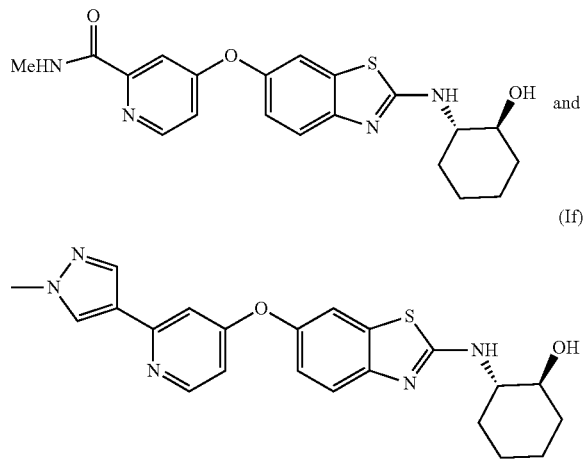

offer the ability to target CSF-1R and PDGFR at similar concentrations, and thus may be even more effective than BLZ945. Indeed, compound (Id) inhibits PDGFR with an IC50 only about 4-fold higher than its IC50 for CSF-1R. Thus a therapeutically effective concentration of either of these compounds is expected to affect both target sites, and to exhibit synergistic activity on gliomas.

Example 7

To investigate the molecular mechanisms whereby BLZ945-treated TAMs can elicit such a striking anti-tumor response in vivo, despite a lack of evident depletion of TAMs or any direct antiproliferative effect on human GBM cells, CD11b$^+$Gr-1$^-$ TAMs were isolated from mice treated with vehicle or BLZ945, and microarray expression profiling was performed (see FIG. 7). Microarray analysis identified 257 genes as significantly differentially expressed between the groups: 52 genes were upregulated and 205 downregulated (FIG. 7B; also 8A). Among these, gene set enrichment analysis (GSEA) revealed that targets of Egr2, a transcription factor downstream of CSF-1R signaling, were downregulated in BLZ945 treated TAMs (FIG. 7C). Disproportionately, genes associated with M2 phase were upregulated (FIGS. 7D and 7E).

Example 8: Gene Expression Changes Induced by the CFR-1R Inhibitor

Figure 8A:
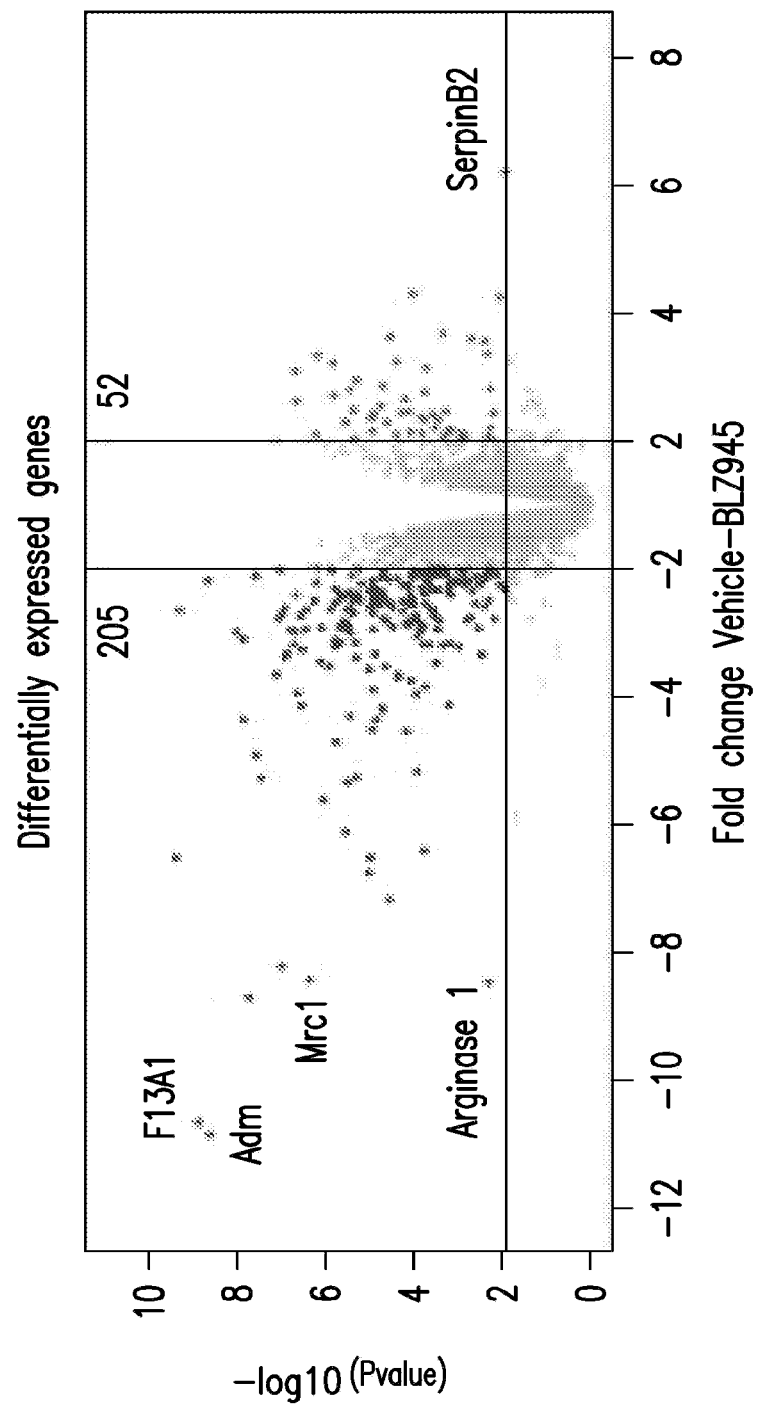
FIG. 8A graphically depicts the degree of upregulation and statistical relevance used to classify differentially-expressed genes in the SVM gene signature.
Figure 8B:
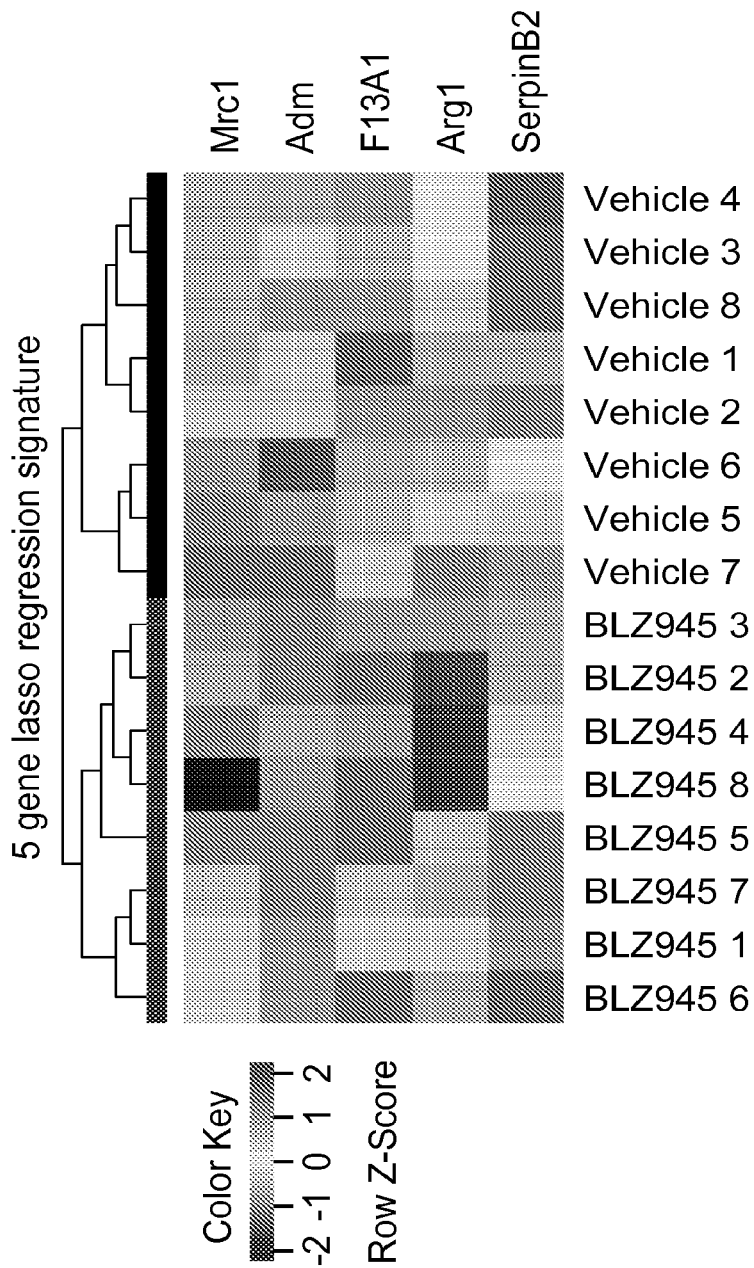
FIG. 8B shows the 5-gene Lasso regression signature.

Lasso regression modeling was employed to determine the minimal number of genes that best discriminated the two treatment groups. This identified a 5-gene signature for BLZ945 treatment comprised of adrenomedullin (Adm), arginase 1 (Arg1), the clotting factor F13a1, mannose receptor C type 1 (Mrc1/CD206), and the protease inhibitor serpinB2 (FIG. 8B). Interestingly, each of these genes has been associated with alternatively activated/M2 macrophage polarization, and 4 of 5 genes are downregulated following BLZ945 treatment. SerpinB2 (also known as PAI2), the only upregulated gene in the 5-gene signature, generally correlates positively with increased survival, particularly in breast cancer patients.

Figure 7A:
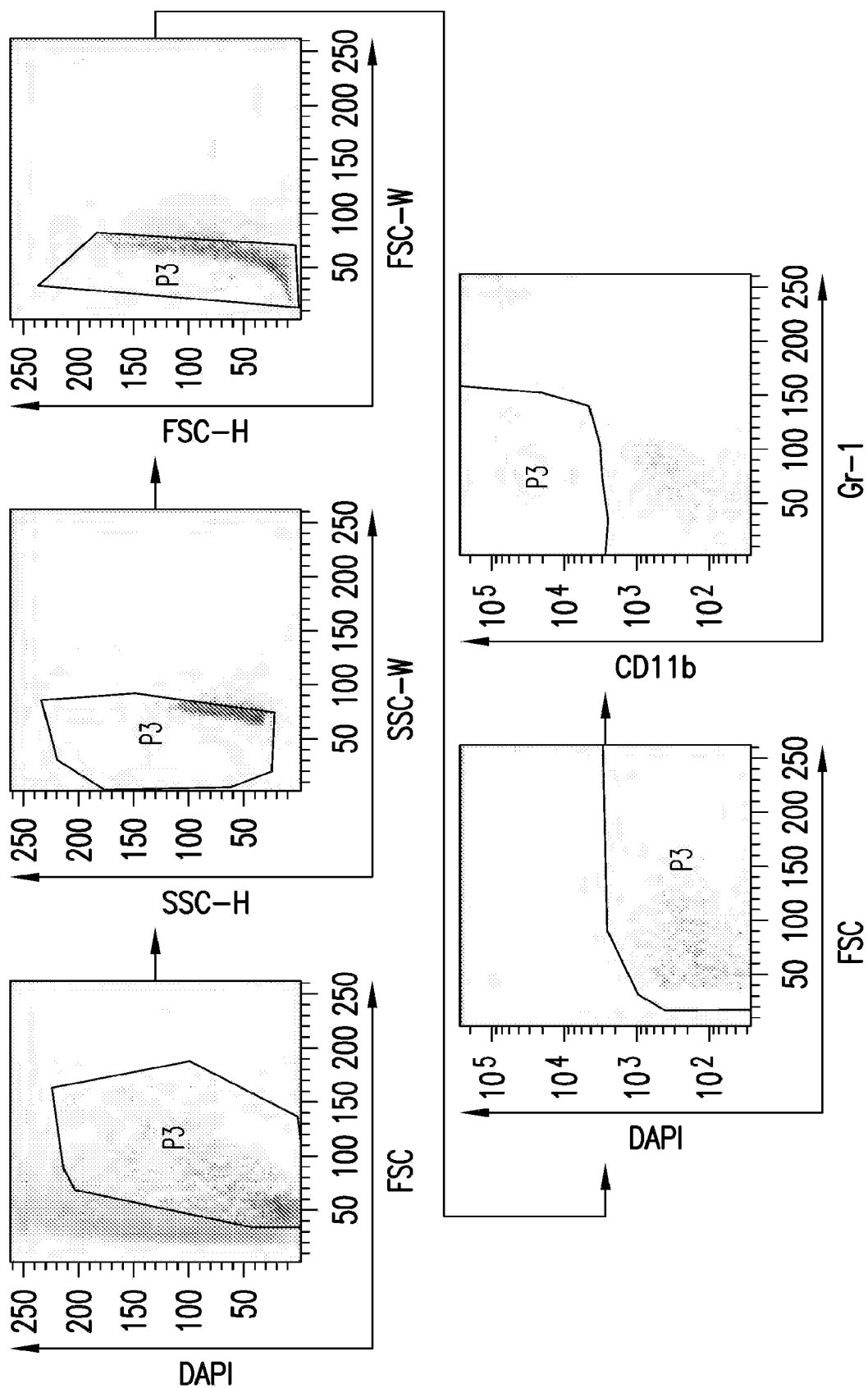
FIG. 7A shows the steps used for FACS separation of cells for gene expression analyses in Example 7.
Figure 7C:
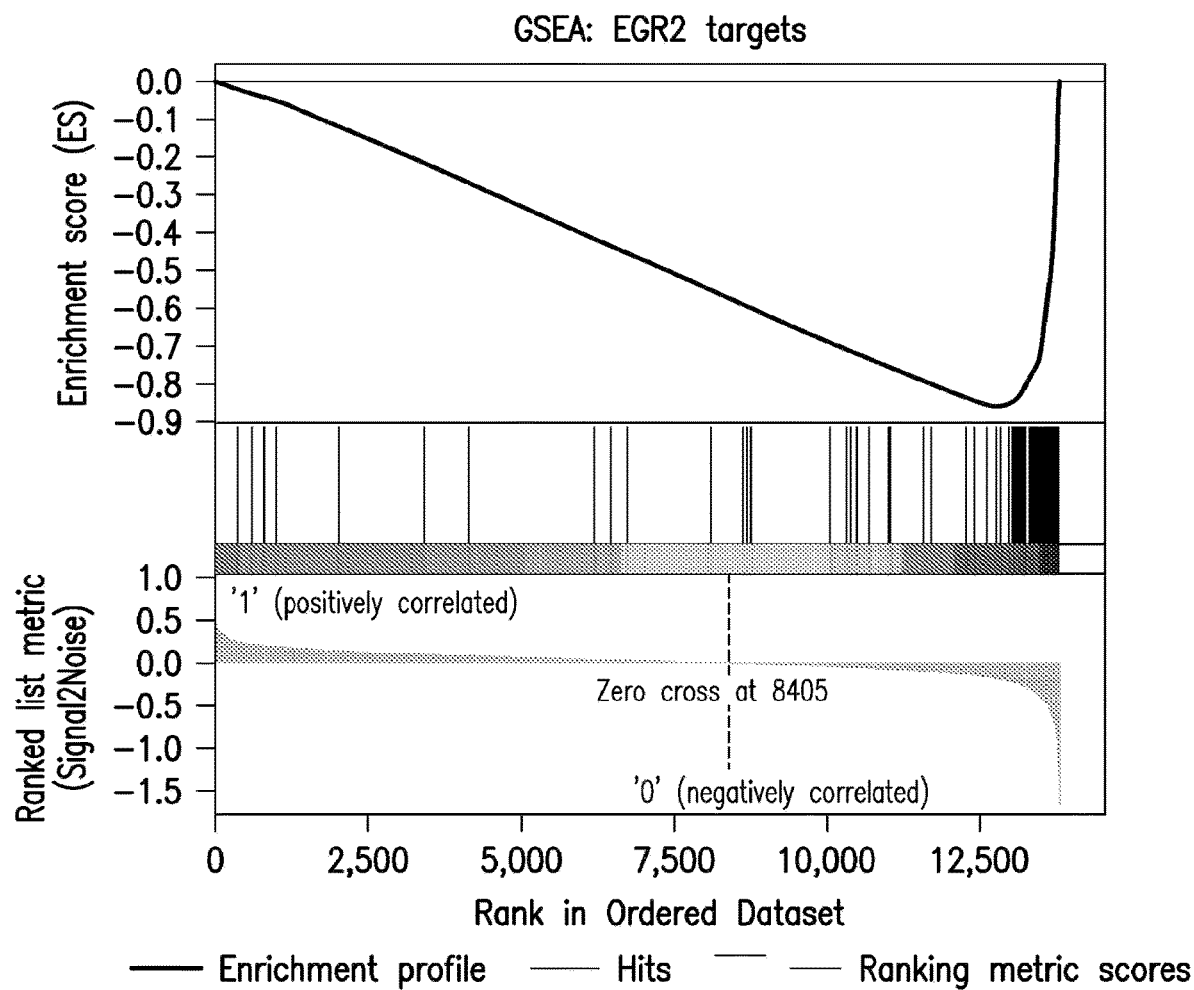
FIGS. 7C-7E show selective upregulation of M2-associated genes and EGR2 targets.
Figure 7D:
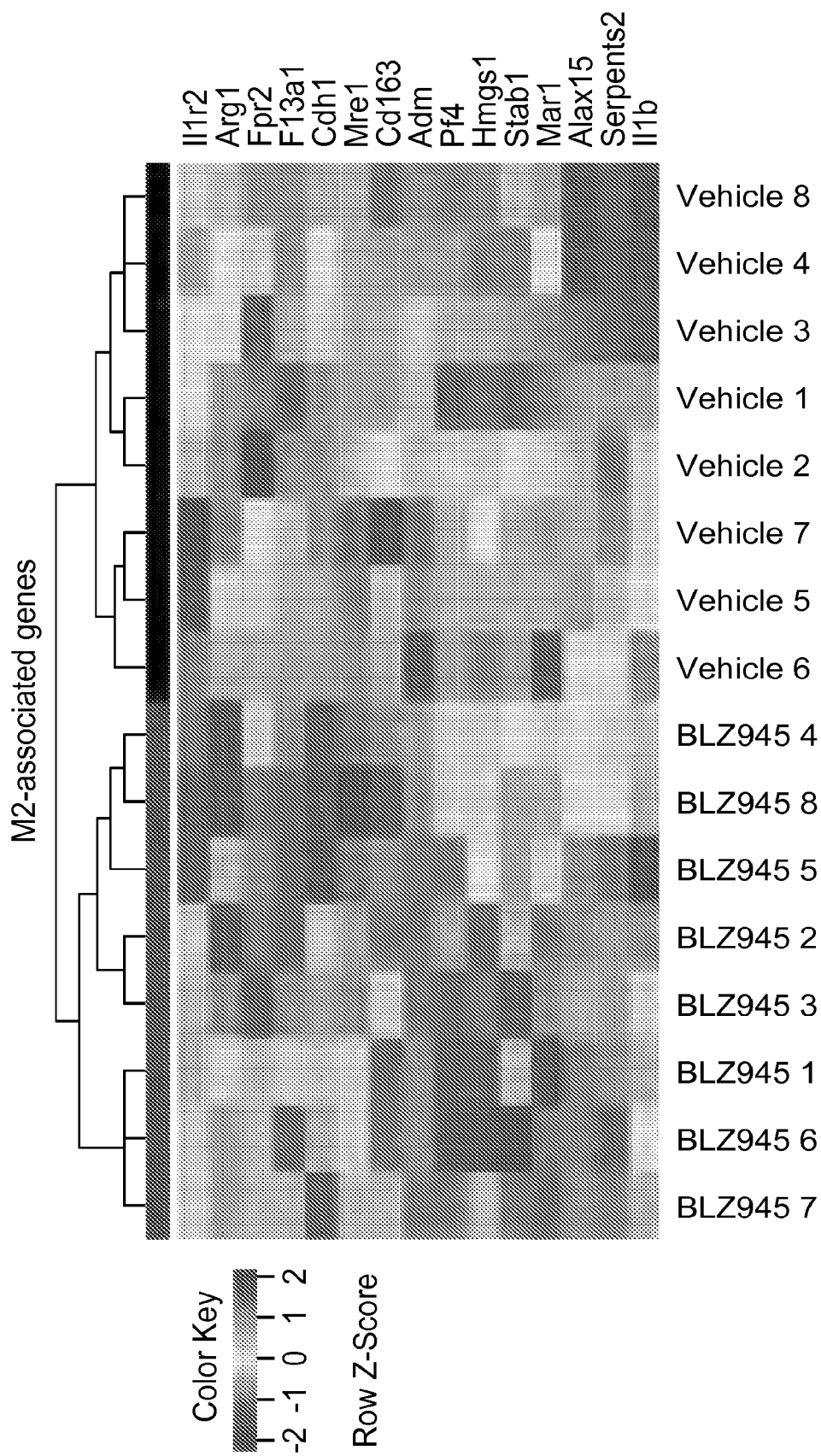
Figure 7E:
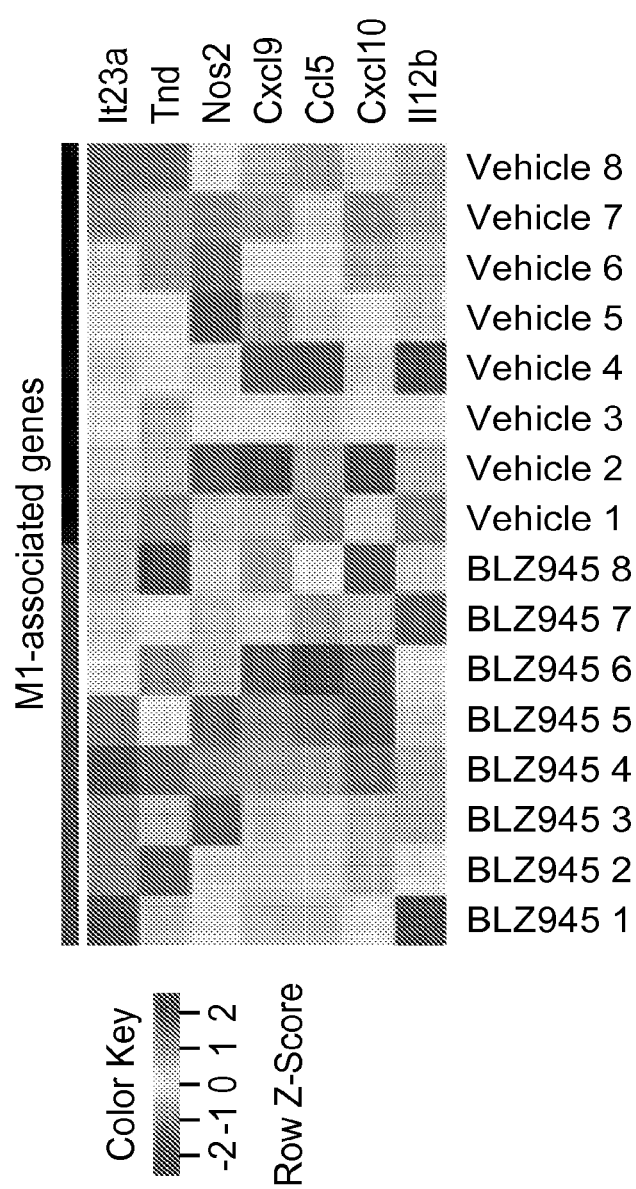

In many tissue contexts TAMs have been found to be more M2 polarized, which has been linked to their immunosuppressive and pro-tumorigenic functions. Further, macrophages in human gliomas exhibit an M2-like phenotype, determined by increased levels of the scavenger receptors CD163 and CD204, which are associated with higher tumor grade. Given the striking enrichment for M2 genes in the restricted 5-gene signature, the 257-gene list was examined to determine if there were additional M2-associated markers altered following BLZ945 treatment. This revealed 10 further genes [Alox15 (arachidonate 15-lipoxygenase); Cdh1 (cadherin); Cd163 (CD163 antigen); Fpr2 (formyl peptide receptor 2); Hmox1 (heme oxygenase (decycling) 1); il1b (interleukin 1 beta); and Stab1 (stabilin 1)], the majority of which were downregulated (FIG. 7D, table 2). Classically activated/M1 polarization genes were not correspondingly upregulated, with the exception of interleukin-1-beta receptor (FIG. 7E). These data suggest that in response to CSF-1R inhibition by BLZ945, TAMs lose their M2 polarization and may gain anti-tumorigenic functions.

This also suggests that monitoring these gene expression changes as biomarkers may provide valuable prognosis information for treatment of glioma patients with CSF-1R inhibitors. Treated subjects whose gene expression profiles change in the same or a similar pattern as these observed changes may be expected to respond positively to treatment with the CSF-1R inhibitor, and those who do not exhibit such gene expression changes may need to receive an alternative or additional treatment due to a negative prognosis on the CSF-1R inhibitor alone.

TABLE 2

Differential gene expression as a result of CSF-1R inhibitor treatment.

| Symbol | Description | Fold Change BLZ945-Vehicle | Nominal P value |
| --- | --- | --- | --- |
| Akap12 | A kinase (PRKA) anchor protein (gravin) 12 | −2.85 | 1.31E−04 |
| Abhd15 | abhydrolase domain containing 15 | −2.48 | 1.36E−05 |
| Acp5 | acid phosphatase 5, tartrate resistant | −2.38 | 2.08E−03 |
| Aoah | acyloxyacyl hydrolase | −2.43 | 3.83E−06 |
| Ada | adenosine deaminase | −3.00 | 2.28E−07 |
| Arxes1 | adipocyte-related X-chromosome expressed sequence 1 | −2.23 | 1.68E−03 |
| Arxes2 | adipocyte-related X-chromosome expressed sequence 2 | −2.96 | 3.37E−04 |
| Adm*# | adrenomedullin | −10.85 | 2.60E−09 |
| Aldh1a2 | aldehyde dehydrogenase family 1, subfamily A2 | −2.18 | 8.36E−04 |
| Apbb2 | amyloid beta (A4) precursor protein-binding, family B, member 2 | 2.27 | 2.97E−06 |
| Anln | anillin, actin binding protein | −2.99 | 1.38E−04 |
| Asb10 | ankyrin repeat and SOCS box-containing 10 | 2.10 | 1.14E−03 |
| Asb11 | ankyrin repeat and SOCS box-containing 11 | 2.19 | 3.00E−04 |

TABLE 2-continued

Differential gene expression as a result of CSF-1R inhibitor treatment.

| Symbol | Description | Fold Change BLZ945-Vehicle | Nominal P value |
|---|---|---|---|
| Mki67 | antigen identified by monoclonal antibody Ki 67 | −7.18 | 2.78E−05 |
| Apob | apolipoprotein B | −2.92 | 3.42E−05 |
| Apoc1 | apolipoprotein C-I | 3.21 | 1.56E−06 |
| Apoc4 | apoplipoprotein C-IV | 3.14 | 1.91E−04 |
| Alox15# | arachidonate 15-lipoxygenase | 4.24 | 8.85E−03 |
| Arg1*# | arginase, liver | −8.48 | 5.07E−03 |
| Aspm | asp (abnormal spindle)-like, microcephaly associated (Drosophila) | −2.22 | 1.02E−03 |
| Aurka | aurora kinase A | −2.23 | 1.30E−03 |
| Aurkb | aurora kinase B | −2.71 | 4.19E−06 |
| Birc5 | baculoviral IAP repeat-containing 5 | −6.13 | 3.00E−06 |
| Bambi | BMP and activin membrane-bound inhibitor, homolog (Xenopus laevis) | 2.64 | 6.53E−05 |
| Bub1 | budding uninhibited by benzimidazoles 1 homolog (S. cerevisiae) | −2.72 | 4.19E−06 |
| Cdh1# | cadherin 1 | −6.43 | 1.70E−04 |
| Cdh2 | cadherin 2 | −2.23 | 6.25E−04 |
| Camkk1 | calcium/calmodulin-dependent protein kinase kinase 1, alpha | −2.13 | 2.69E−08 |
| Calml4 | calmodulin-like 4 | −2.06 | 2.12E−05 |
| Chst2 | carbohydrate sulfotransferase 2 | 2.44 | 5.14E−04 |
| Cbr2 | carbonyl reductase 2 | −4.15 | 2.93E−07 |
| Cpa3 | carboxypeptidase A3, mast cell | 2.17 | 6.30E−04 |
| Ctnnd2 | catenin (cadherin associated protein), delta 2 | −2.94 | 8.46E−07 |
| Ctsf | cathepsin F | 2.10 | 1.53E−04 |
| Cd163# | CD163 antigen | −2.65 | 3.87E−07 |
| Cd22 | CD22 antigen | 2.35 | 1.09E−05 |
| Cd244 | CD244 natural killer cell receptor 2B4 | −2.71 | 1.11E−07 |
| Cd38 | CD38 antigen | −3.72 | 4.44E−05 |
| Cd5 | CD5 antigen | 3.62 | 2.96E−05 |
| Cd83 | CD83 antigen | 2.28 | 2.53E−05 |
| Cd93 | CD93 antigen | −2.42 | 2.30E−07 |
| Cks1b | CDC28 protein kinase 1b | −2.54 | 1.71E−06 |
| Cdc20 | cell division cycle 20 homolog (S. cerevisiae) | −2.75 | 1.16E−04 |
| Cdc45 | cell division cycle 45 homolog (S. cerevisiae) | −2.03 | 9.78E−08 |
| Cdc6 | cell division cylce 6 homolog (S. cerevisiae) | −3.67 | 8.12E−08 |
| Cdca5 | cell division cycle associated 5 | −2.24 | 6.77E−06 |
| Cenpe | centromere protein E | −4.18 | 1.96E−05 |
| Cenpk | centromere protein K | −2.45 | 1.46E−05 |
| Cep55 | centrosomal protein 55 | −2.40 | 8.23E−05 |
| Ccr1 | chemokine (C-C motif) receptor 1 | −4.56 | 6.86E−05 |
| Cxcr7 | chemokine (C—X—C motif) receptor 7 | −2.26 | 8.65E−03 |
| Cspg5 | chondroitin sulfate proteoglycan 5 | −2.61 | 1.09E−05 |
| Clu | clusterin | −2.34 | 3.55E−04 |
| F3 | coagulation factor III | −2.11 | 4.58E−03 |
| F9 | coagulation factor IX | 2.12 | 5.92E−04 |
| F13a1*# | coagulation factor XIII, A1 subunit | −10.66 | 1.39E−09 |
| Col11a1 | collagen, type XI, alpha 1 | −3.49 | 3.09E−04 |
| Col14a1 | collagen, type XIV, alpha 1 | −2.65 | 1.37E−06 |
| Cfp | complement factor properdin | −2.64 | 2.60E−04 |
| Cntn1 | contactin 1 | −4.93 | 2.80E−08 |
| Cpne2 | copine II | −2.20 | 1.13E−05 |
| Crybb1 | crystallin, beta B1 | −2.83 | 2.44E−05 |
| Clec4n | C-type lectin domain family 4, member n | −6.53 | 4.34E−10 |
| Ccna2 | cyclin A2 | −3.90 | 1.19E−05 |
| Ccnb1 | cyclin B1 | −3.55 | 2.25E−05 |
| Ccnb2 | cyclin B2 | −4.53 | 1.16E−05 |
| Ccnd1 | cyclin D1 | −3.01 | 1.06E−08 |
| Ccnd2 | cyclin D2 | −3.34 | 1.36E−05 |
| Ccne2 | cyclin E2 | −5.28 | 3.67E−08 |
| Ccnf | cyclin F | −2.30 | 1.48E−04 |
| Cdk1 | cyclin-dependent kinase 1 | −2.18 | 2.75E−05 |
| Cst7 | cystatin F (leukocystatin) | 2.62 | 2.29E−07 |
| Cyp4v3 | cytochrome P450, family 4, subfamily v, polypeptide 3 | 2.14 | 1.15E−05 |
| Cpeb1 | cytoplasmic polyadenylation element binding protein 1 | 2.86 | 1.97E−05 |
| Ckap2 | cytoskeleton associated protein 2 | −2.17 | 1.80E−04 |
| Ddhd1 | DDHD domain containing 1 | 2.06 | 4.86E−03 |
| Dner | delta/notch-like EGF-related receptor | −2.68 | 2.65E−04 |
| Dck | deoxycytidine kinase | −2.07 | 2.50E−04 |
| Depdc1a | DEP domain containing 1a | −2.81 | 9.05E−05 |
| Dhfr | dihydrofolate reductase | −2.40 | 5.79E−06 |
| Prim1 | DNA primase, p49 subunit | −2.76 | 2.87E−07 |
| D17H6S56E-5 | DNA segment, Chr 17, human D6S56E 5 | −2.01 | 1.66E−03 |

TABLE 2-continued

Differential gene expression as a result of CSF-1R inhibitor treatment.

| Symbol | Description | Fold Change BLZ945-Vehicle | Nominal P value |
|---|---|---|---|
| Ddit4 | DNA-damage-inducible transcript 4 | −2.43 | 5.07E−06 |
| Dusp1 | dual specificity phosphatase 1 | 2.33 | 3.55E−04 |
| E2f8 | E2F transcription factor 8 | −2.71 | 1.20E−05 |
| Ect2 | ect2 oncogene | −3.19 | 1.65E−04 |
| Emb | embigin | −2.59 | 9.66E−05 |
| Eepd1 | endonuclease/exonuclease/phosphatase family domain containing 1 | 2.70 | 1.62E−06 |
| Ezh2 | enhancer of zeste homolog 2 (Drosophila) | −2.54 | 1.36E−05 |
| Etl4 | enhancer trap locus 4 | 2.41 | 1.24E−05 |
| Eps8 | epidermal growth factor receptor pathway substrate 8 | −2.51 | 4.00E−06 |
| Emp1 | epithelial membrane protein 1 | −3.19 | 6.42E−04 |
| Ephx1 | epoxide hydrolase 1, microsomal | 2.76 | 1.75E−04 |
| Ero11 | ERO1-like (S. cerevisiae) | −2.64 | 1.07E−05 |
| Fam20c | family with sequence similarity 20, member C | 2.79 | 3.62E−06 |
| Fabp3 | fatty acid binding protein 3, muscle and heart | 2.93 | 4.99E−06 |
| Fabp7 | fatty acid binding protein 7, brain | −6.77 | 9.66E−06 |
| Fbxo32 | F-box protein 32 | 2.54 | 1.79E−05 |
| Fbn2 | fibrillin 2 | −2.13 | 3.89E−03 |
| Fap | fibroblast activation protein | −2.25 | 1.46E−03 |
| Fpr2# | formyl peptide receptor 2 | −2.83 | 6.68E−05 |
| Fhl1 | four and a half LIM domains 1 | −2.02 | 5.40E−03 |
| Gja1 | gap junction protein, alpha 1 | −2.78 | 1.97E−03 |
| Gpnmb | glycoprotein (transmembrane) nmb | 3.22 | 3.98E−05 |
| Ggta1 | glycoprotein galactosyltransferase alpha 1, 3 | −2.4 | 2.12E−06 |
| Gpm6a | glycoprotein m6a | −5.35 | 3.23E−06 |
| Gzma | granzyme A | 3.55 | 4.11E−03 |
| Gadd45a | growth arrest and DNA-damage-inducible 45 alpha | 2.40 | 2.77E−04 |
| Gap43 | growth associated protein 43 | −2.56 | 7.42E−05 |
| Gdf3 | growth differentiation factor 3 | −3.33 | 1.40E−07 |
| Gem | GTP binding protein (gene overexpressed in skeletal muscle) | 2.17 | 7.03E−04 |
| Hspa1a | heat shock protein 1A | −4.38 | 1.45E−05 |
| Hspa1b | heat shock protein 1B | −8.71 | 1.88E−08 |
| Hsp90aa1 | heat shock protein 90, alpha (cytosolic), class A member 1 | −2.23 | 1.01E−03 |
| Hells | helicase, lymphoid specific | −3.59 | 9.75E−06 |
| Hmox1# | heme oxygenase (decycling) 1 | −2.90 | 7.05E−05 |
| Hmgb3 | high mobility group box 3 | −2.42 | 2.32E−06 |
| Hmgn5 | high-mobility group nucleosome binding domain 5 | −2.58 | 1.79E−05 |
| Igj | immunoglobulin joining chain | 3.36 | 4.53E−03 |
| Ikbke | inhibitor of kappaB kinase epsilon | 2.38 | 1.50E−04 |
| Igf1 | insulin-like growth factor 1 | 2.13 | 8.56E−05 |
| Igfbp2 | insulin-like growth factor binding protein 2 | −3.54 | 1.24E−06 |
| Igfbp3 | insulin-like growth factor binding protein 3 | −6.53 | 1.05E−05 |
| Itgam | integrin alpha M | −2.25 | 2.27E−04 |
| Itgax | integrin alpha X | 2.08 | 1.36E−03 |
| Ifitm1 | interferon induced transmembrane protein 1 | −5.18 | 1.21E−04 |
| Ifitm2 | interferon induced transmembrane protein 2 | −2.82 | 1.54E−03 |
| Ifitm3 | interferon induced transmembrane protein 3 | −2.06 | 4.73E−03 |
| Ifitm6 | interferon induced transmembrane protein 6 | −4.14 | 6.14E−04 |
| Il1b# | interleukin 1 beta | 2.06 | 4.50E−04 |
| Il18bp | interleukin 18 binding protein | 3.66 | 4.53E−04 |
| Il7r | interleukin 7 receptor | −2.01 | 4.96E−03 |
| Kpna2 | karyopherin (importin) alpha 2 | −2.36 | 1.98E−05 |
| Khdrbs3 | KH domain containing, RNA binding, signal transduction associated 3 | −2.10 | 3.94E−04 |
| Klrb1a | killer cell lectin-like receptor subfamily B member 1A | 4.30 | 9.00E−05 |
| Kif11 | kinesin family member 11 | −2.57 | 9.00E−05 |
| Pbk | PDZ binding kinase | −5.63 | 9.20E−07 |
| Pttg1 | pituitary tumor-transforming gene 1 | −2.83 | 2.73E−06 |
| Plac8 | placenta-specific 8 | −2.79 | 6.64E−03 |
| Pdgfra | platelet derived growth factor receptor, alpha polypeptide | −3.16 | 4.84E−06 |
| Pf4 | platelet factor 4 | −2.96 | 1.21E−05 |
| Pdgfc | platelet-derived growth factor, C polypeptide | −2.25 | 2.98E−03 |
| Ptn | pletotrophin | −3.21 | 4.42E−04 |
| Pdpn | podoplanin | −2.01 | 3.51E−04 |
| Plk1 | polo-like kinase 1 (Drosophila) | −2.68 | 5.72E−05 |
| Pola1 | polymerase (DNA directed), alpha 1 | −2.37 | 3.52E−06 |
| Pold2 | polymerase (DNA directed), delta 2, regulatory subunit | −2.02 | 5.72E−06 |
| Pole | polymerase (DNA directed), epsilon | −2.27 | 5.96E−05 |
| Kcnk2 | potassium channel, subfamily K, member 2 | −2.13 | 8.52E−05 |
| Prickle1 | prickle homolog 1 (Drosophila) | 2.32 | 1.75E−04 |

TABLE 2-continued

Differential gene expression as a result of CSF-1R inhibitor treatment.

| Symbol | Description | Fold Change BLZ945-Vehicle | Nominal P value |
|---|---|---|---|
| P4ha2 | procollagen-proline, 2-oxoglutarate 4-dioxygenase (proline 4-hydroxylase), alpha II polypeptide | −3.54 | 1.25E−06 |
| Ptger4 | prostaglandin E receptor 4 (subtype EP4) | 2.43 | 5.12E−05 |
| Pmepa1 | prostate transmembrane protein, androgen induced 1 | −2.35 | 5.85E−04 |
| Psmb7 | proteasome (prosome, macropain) subunit, beta type 7 | −2.17 | 4.27E−03 |
| Prc1 | protein regulator of cytokinesis 1 | −3.06 | 1.26E−04 |
| Ptprz1 | protein tyrosin phosphatase, receptor type Z, polypeptide 1 | −3.66 | 4.43E−05 |
| P2ry12 | purinergic receptor P2Y, G-protein coupled 12 | −2.55 | 1.86E−04 |
| Rab34 | RAB34, member of RAS oncogene family | 2.08 | 3.95E−05 |
| Racgap1 | Rac GTPase-activating protein 1 | −2.56 | 2.92E−05 |
| Rad51ap1 | RAD51 associated protein 1 | −2.61 | 1.26E−07 |
| Rad51 | RAD51 homolog (S. cerevisiae) | −2.90 | 3.33E−06 |
| Ranbp1 | RAN binding protein 1 | −2.01 | 6.62E−07 |
| Rfc4 | replication factor C (activator 1) 4 | −2.17 | 4.24E−05 |
| Rbp1 | retinol binding protein 1, celluluar | −4.22 | 1.88E−05 |
| Rrm1 | ribonucleotide reductase M1 | −2.14 | 1.79E−05 |
| Rrm2 | ribonucleotide reductase M2 | −8.23 | 1.04E−07 |
| 2310016C08Rik | RIKEN cDNA 2310016C08 gene | −2.14 | 1.12E−04 |
| 2810417H13Rik | RIKEN cDNA 2810417H13 gene | −3.96 | 2.33E−07 |
| 4930583H14Rik | RIKEN cDNA 4930583H14 gene | −2.37 | 1.25E−05 |
| Rbm3 | RNA binding motif protein 3 | −2.20 | 2.23E−09 |
| Slfn4 | schlafen 4 | −3.35 | 3.42E−03 |
| Stil | Scl/Tal1 interrupting locus | −3.15 | 2.15E−06 |
| Serpinb2*# | serine (or cysteine) peptidase inhibitor, clade B, member 2 | 6.20 | 1.12E−02 |
| Serpinb6b | serine (or cysteine) peptidase inhibitor, clade B, member 6b | 2.03 | 1.22E−03 |
| Smyd2 | SET and MYND domain containing 2 | −2.25 | 6.90E−04 |
| Sh3bgr | SH3-binding domain glutamic acid-rich protein | 3.33 | 6.64E−07 |
| Sh3bgrl | SH3-binding domain glutamic acid-rich protein like | −2.02 | 4.68E−04 |
| Shcbp1 | Shc SH2-domain binding protein 1 | −4.72 | 1.74E−06 |
| Slamf8 | SLAM family member 8 | 2.81 | 5.20E−03 |
| Snrpa1 | small nuclear ribonucleoprotein polypeptide A' | −2.04 | 1.48E−06 |
| Slc2a5 | solute carrier family 2 (facilitated glucose transporter), member 5 | −3.46 | 8.15E−07 |
| Slc39a4 | solute carrier family 39 (zinc transporter), member 4 | 2.44 | 7.83E−05 |
| Slc6a1 | solute carrier family 6 (neurotransmitter transporter, GABA), member 1 | −2.09 | 5.66E−04 |
| Sparcl1 | SPARC-like 1 | −3.23 | 1.06E−03 |
| Spon1 | spondin 1, (f-spondin) extracellular matrix protein | −2.50 | 9.32E−05 |
| Sox2 | SRY-box containing gene 2 | −2.50 | 5.13E−03 |
| Stab1# | stabilin 1 | −2.64 | 3.92E−06 |
| Stmn1 | stathmin 1 | −2.52 | 5.52E−05 |
| Smc2 | structural maintenance of chromosomes 2 | −2.87 | 7.80E−05 |
| Smc4 | structural maintenance of chromosomes 4 | −3.20 | 2.26E−04 |
| St14 | suppression of tumorigenicity 14 (colon carcinoma) | 2.47 | 4.21E−06 |
| Tiparp | TCDD-inducible poly(ADP-ribose) polymerase | −2.06 | 1.25E−03 |
| Tnc | tenascin C | −2.56 | 2.48E−03 |
| Tk1 | thymidine kinase 1 | −3.39 | 1.24E−07 |
| Tipin | timeless interacting protein | −2.50 | 6.24E−06 |
| Tfpi2 | tissue factor pathway inhibitor 2 | −2.60 | 3.99E−03 |
| Timp1 | tissue inhibitor of metalloproteinase 1 | −2.07 | 1.64E−04 |
| Top2a | topoisomerase (DNA) II alpha | −2.11 | 2.13E−05 |
| Topbp1 | topoisomerase (DNA) II binding protein 1 | −2.37 | 9.96E−06 |
| Tpx2 | TPX2, microtubule-associated protein homolog (Xenopus laevis) | −2.52 | 1.16E−05 |
| Tcf19 | transcription factor 19 | −2.32 | 1.67E−06 |
| Tgfb1 | transforming growth factor, beta induced | −3.23 | 1.68E−06 |
| Tgm2 | transglutaminase 2, C polypeptide | −2.94 | 2.86E−03 |
| Tmem119 | transmembrane protein 119 | −3.12 | 1.71E−06 |
| Tmem163 | transmembrane protein 163 | 2.20 | 5.42E−03 |
| Trps1 | trichorhinophalangeal syndrome I (human) | −2.97 | 1.68E−07 |
| Trim59 | tripartite motif-containing 59 | −2.78 | 3.02E−04 |
| Ttk | Ttk protein kinase | −2.63 | 3.35E−05 |
| Tubb2c | tubulin, beta 2C | −2.13 | 3.84E−06 |
| Ube2c | ubiquitin-conjugating enzyme E2C | −3.98 | 1.12E−04 |
| Uhrf1 | ubiquitin-like, containing PHD and RING finger domains, 1 | −2.96 | 3.73E−07 |
| Ung | uracil DNA glycosylase | −2.50 | 5.81E−07 |
| Wdhd1 | WD repeat and HMG-box DNA binding protein 1 | −2.01 | 2.52E−04 |

TABLE 2-continued

Differential gene expression as a result of CSF-1R inhibitor treatment.

| Symbol | Description | Fold Change BLZ945-Vehicle | Nominal P value |
|---|---|---|---|
| Zwilch | Zwilch, kinetochore associated, homolog (*Drosophila*) | −4.32 | 3.61E−08 |

*Component of Lasso regression signature of response to BLZ945.
Relevant M2 macrophage-associated genes.

In the Table, downregulated genes are given a negative 'fold change' number, while upregulated genes have positive values. Nominal p values are from Student's two-tailed t-test.

Figure 8C:
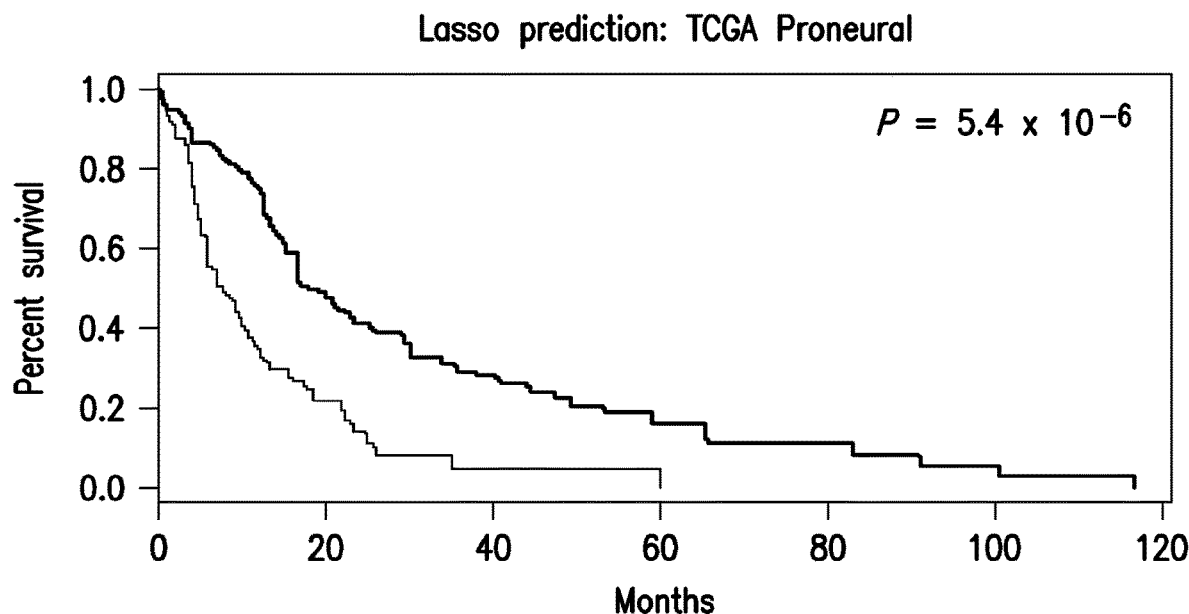
FIG. 8C shows the Lasso gene signature prediction for proneural GBM tumors in the TCGA data set.
Figure 8D:
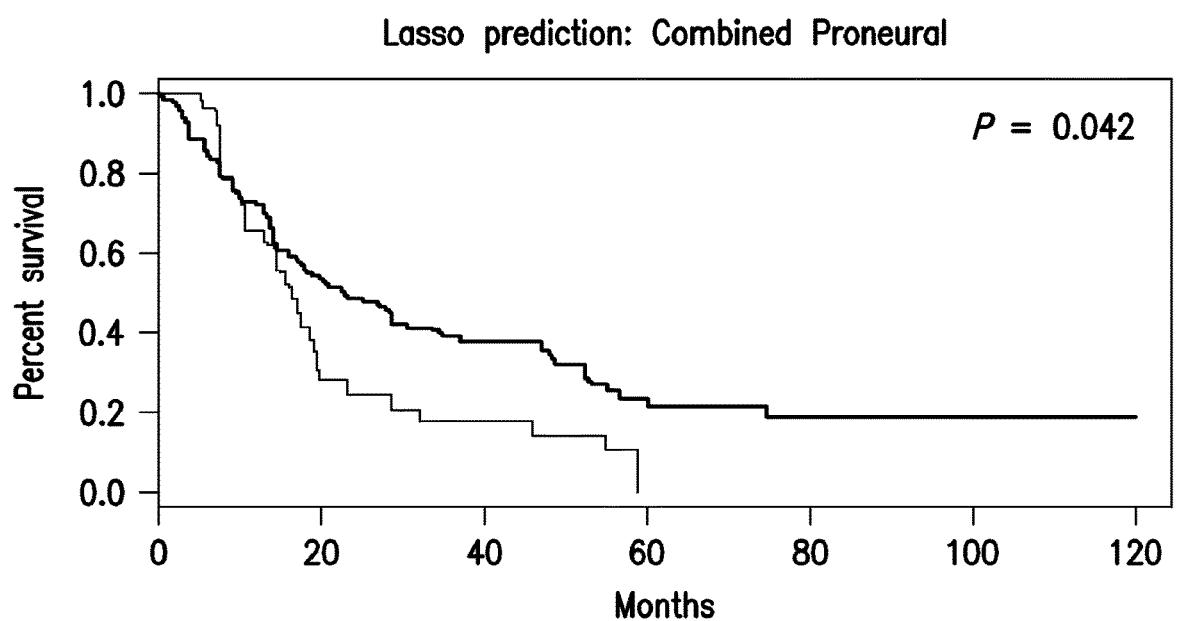
FIG. 8D shows the Lasso gene signature prediction for proneural GBM tumors in the combined data set.
Figure 8E:
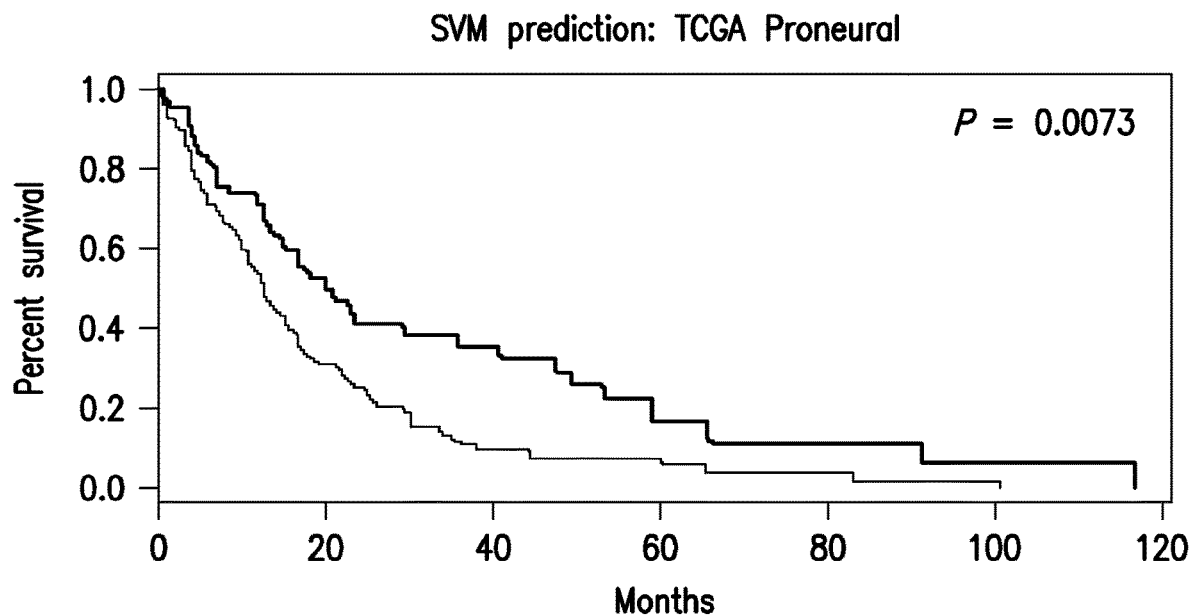
FIG. 8E shows the SVM gene signature prediction for proneural GBM tumors in the TCGA data set.
Figure 8F:
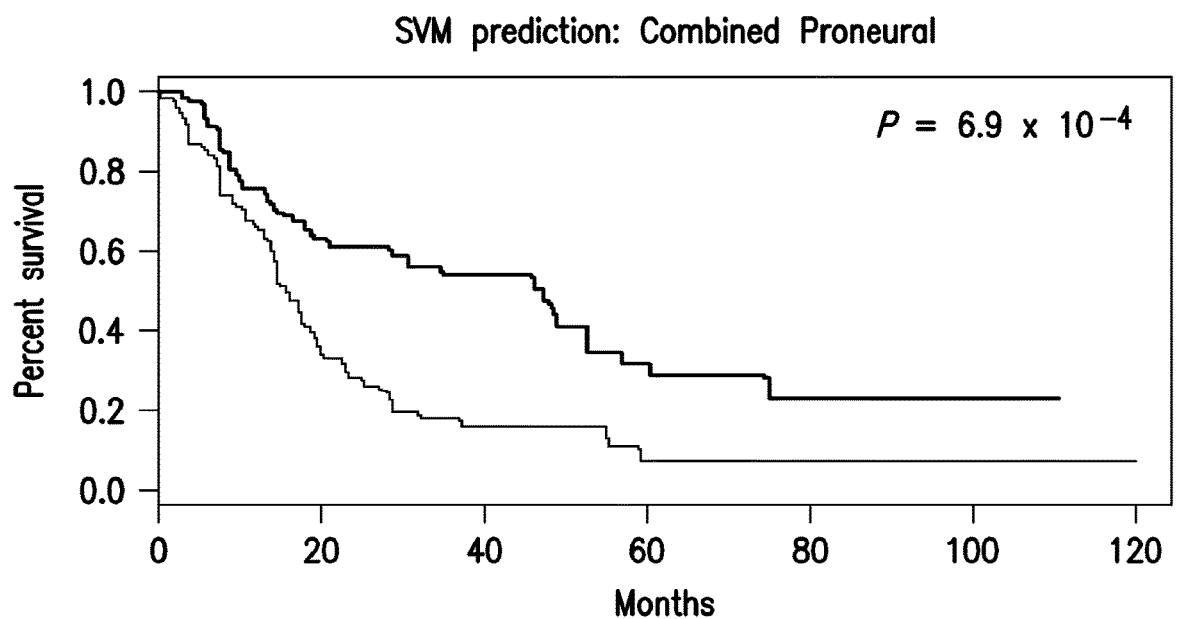
FIG. 8F shows the SVM gene signature prediction for proneural GBM tumors in the combined data set.

In addition, gene signatures generated from BLZ945-treated TAMs in mice appear to be associated with differential survival in GBM patients. A support vector machine (SVM) and the Lasso signature were used to analyze GBM data from The Cancer Gene Atlas (TCGA) and a second combined series of GBM datasets and segregate patients into either 'BLZ945' or 'Vehicle' classifiers. These analyses revealed an increase in median survival ranging from 10 months in TCGA proneural patients using the Lasso signature (FIGS. 8C and 8D) to 31.5 months in the combined datasets with the SVM signature (FIGS. 8E and 8F). Interestingly, this increase in survival was not evident in other subtypes of GBM, and was not dependent upon enrichment of G-CIMP$^+$ proneural patients.

TABLE 3

Survival data for the Support Vector Machine (SVM) and Lasso models in the different GBM populations.

| Group | BLZ945 | Vehicle | Median Survival | P value |
|---|---|---|---|---|
| SVM Combined Neural | 49 | 16 | 5.42 | 1.59E−01 |
| SVM Combined Proneural | 46 | 62 | 31.54 | 6.86E−04 |
| SVM Combined Mesenchymal | 37 | 102 | −2.25 | 8.92E−01 |
| SVM Combined Classical | 11 | 48 | 0.40 | 6.67E−01 |
| SVM TCGA Proneural | 45 | 88 | 7.64 | 7.27E−03 |
| SVM TCGA Proneural GCIMP | 13 | 8 | −40.60 | 2.01E−01 |
| SVM TCGA Proneural non GCIMP | 22 | 44 | −0.76 | 2.64E−01 |
| SVM TCGA GCIMP | 14 | 8 | −35.60 | 2.03E−01 |
| SVM TCGA non GCIMP | 83 | 157 | −1.06 | 7.27E−01 |
| SVM TCGA Neural | 23 | 30 | 2.84 | 7.73E−01 |
| SVM TCGA Mesenchymal | 53 | 99 | 0.30 | 7.62E−01 |
| SVM TCGA Classical | 31 | 56 | −3.14 | 7.71E−01 |
| Lasso Combined Neural | 51 | 14 | 7.01 | 6.50E−02 |

TABLE 3-continued

Survival data for the Support Vector Machine (SVM) and Lasso models in the different GBM populations.

| Group | BLZ945 | Vehicle | Median Survival | P value |
|---|---|---|---|---|
| Lasso Combined Proneural | 79 | 29 | 6.51 | 4.15E−02 |
| Lasso Combined Mesenchymal | 21 | 118 | 1.88 | 5.55E−01 |
| Lasso Combined Classical | 28 | 31 | 0.33 | 9.68E−01 |
| Lasso TCGA Proneural | 84 | 49 | 9.98 | 5.41E−06 |
| Lasso TCGA Proneural GCIMP | 20 | 1 | NA | NA |
| Lasso TCGA Proneural non GCIMP | 40 | 26 | 10.84 | 1.40E−02 |
| Lasso TCGA GCIMP | 20 | 2 | −16.13 | 7.21E−01 |
| Lasso TCGA non GCIMP | 100 | 140 | 0.10 | 4.14E−01 |
| Lasso TCGA Neural | 31 | 22 | −5.19 | 2.77E−02 |
| Lasso TCGA Mesenchymal | 23 | 129 | 0.40 | 8.35E−01 |
| Lasso TCGA Classical | 49 | 48 | −1.42 | 6.34E−01 |

Figure 8G:
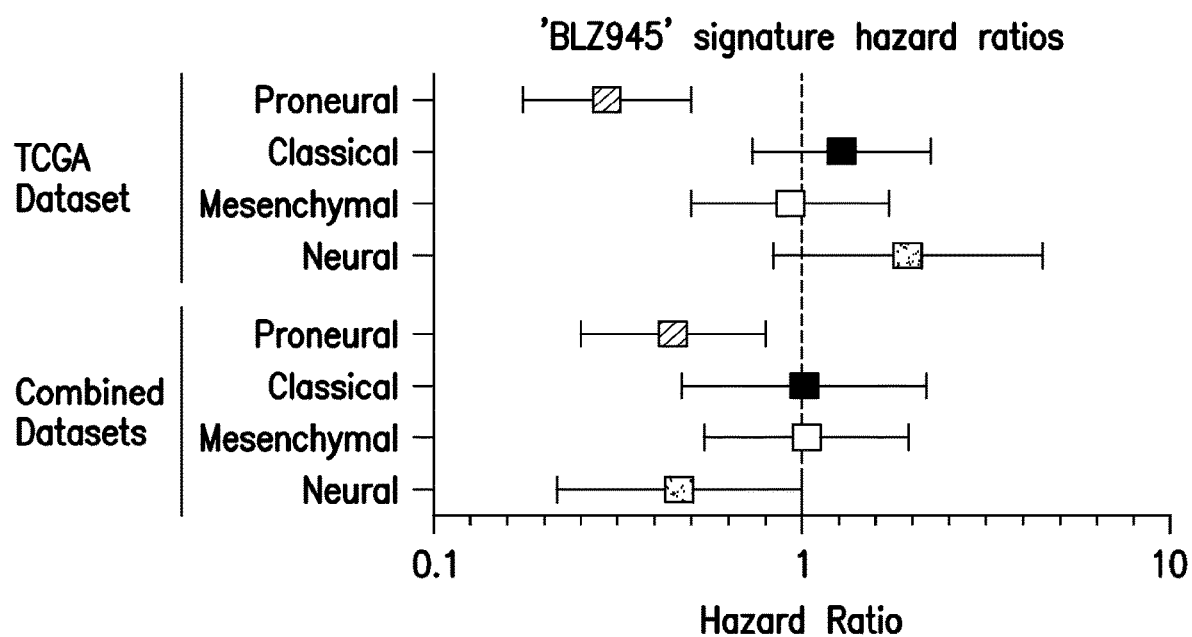
FIG. 8G depicts the BLZ945 gene signature hazard ratios for the TCGA and combined data sets, for proneural, classical, mesenchymal, and neural GBM tumors, and highlights the statistical correlation with proneural GBM across all of the data.

Analysis of associated hazard ratios demonstrated the proneural-specific survival advantage in both TCGA and the combined data sets (FIG. 8G). The proneural specificity is consistent with the TAM signatures originally having been generated from the PDG model of gliomagenesis, which most closely represents proneural GBM. This suggests these gene signatures can provide useful prognostic guidance for subjects undergoing treatment with chemotherapeutics, particularly GBM patients treated with CSF-1R inhibitors. As proneural GBM does not respond to aggressive chemo- and radiotherapy compared to the other subtypes, the finding of prognostic value associated with these signatures may have important translational potential for this group of patients. Based on the observed correlation, patients receiving chemotherapy who exhibit a gene signature at least about 80% similar to either the Lasso or the SVM gene signature are expected to respond positively to that chemotherapeutic. In particular, this correlation is expected to be useful with subjects treated with an inhibitor of CSF-1R, particularly compounds of Formula (I) as described herein.

TABLE 4

Hazard rations and associated 95% confidence intervals for the Lasso regression model in different G-CIMP and non-G-CIMP patient groups. G-CIMP corresponds to Glioma CpG Island Methylator Phenotype. P values were obtained using Wald's test.

| Strata | Patient Population | Model | Hazard Ratio | 95% CI | P value |
|---|---|---|---|---|---|
| 'BLZ945' Lasso | Non-GCIMP Proneural* | Univariate | 0.4921 | (0.2766-0.8756) | 0.0063 |
| 'BLZ945' Lasso | All Proneural | Univariate | 0.3937 | (0.2601-0.5961) | 9.729e−06 |
| G-CIMP | All Proneural | Univariate | 0.3289 | (0.1481-0.7304) | 0.01367 |
| G-CIMP | All Proneural | Multivariate* | 0.4601 | (0.1972-1.0733) | 0.00783 |

TABLE 4-continued

Hazard rations and associated 95% confidence intervals for the Lasso regression model in different G-CIMP and non-G-CIMP patient groups. G-CIMP corresponds to Glioma CpG Island Methylator Phenotype. P values were obtained using Wald's test.

| Strata | Patient Population | Model | Hazard Ratio | 95% CI | P value |
|---|---|---|---|---|---|
| 'BLZ945 Lasso | All Proneural | Multivariate** | 0.4295 | (0.2304-0.8007) | 0.07244 |

*Set of proneural patients with methylation data that are definitively not G-CIMP positive (67/133 total Proneural TCGA patients.)
** Multivariate cox proportional hazard model using both G-CIMP and 'BLZ945' classification strata.

TABLE 5

Hazard rations for the Lasso regression model in different patient datasets. P values were obtained using Wald's test. Only hazard ratios from the proneural subtypes are statistically significant.

| Group | Hazard Ratio | 95% CI | P value |
|---|---|---|---|
| TCGA - Proneural | 0.29 | (0.17-0.50) | 6.32E-06 |
| TCGA - Classical | 1.28 | (0.73-2.26) | 3.89E-01 |
| TCGA - Mesenchymal | 0.93 | (0.49-1.72) | 8.07E-01 |
| TCGA - Neural | 1.93 | (0.83-4.46) | 1.25E01 |
| Combined - Proneural | 0.44 | (0.25-0.79) | 5.97E-03 |
| Combined - Classical | 1.01 | (0.47-2.17) | 9.79E-01 |
| Combined - Mesenchymal | 1.02 | (0.54-1.94) | 9.43E-01 |
| Combined - Neural | 0.46 | (0.22-1.01) | 5.23E-02 |

Methods and Materials Used

Mice

All animal studies were approved by the Institutional Animal Care and Use Committee of Memorial Sloan-Kettering Cancer Center. The Nestin-Tv-a; Ink4a/Arf−/− mouse model (mixed strain background) has been previously described (see E. Tchougounova et al., Oncogene 26, 6289 (2007)). Wild-type (WT) C57BL/6 mice and β-actin-GFP (C57BL/6) mice were purchased from Charles River Laboratories and Jackson Laboratories respectively, and also bred within our animal facility.

Intracranial Injections

The initiation of tumors with RCAS-PDGF-B-HA in adult mice has been previously described (A. H. Shih et al., Cancer Res 64, 4783 (2004)). Briefly, mice were fully anesthetized with 10 mg/ml ketamine/1 mg/ml xylazine and were subcutaneously injected with 50 µl of the local anesthetic 0.25% bupivacaine at the surgical site. Mice were intracranially injected with 1 µl containing 2×105 DF-1: RCAS-PDGF-B-HA cells between 5-6 weeks of age using a fixed stereotactic apparatus (Stoelting). Injections were made to the right frontal cortex, approximately 1.5 mm lateral and 1 mm caudal from bregma, and ata depth of 2 mm.

To investigate the cell type specific expression of CSF-1 and CSF-1R in flow cytometric sorted cell populations, tumors were initiated in mice with RCAS-PDGF-B-HA-SV40-eGFP (RCAS-PDGF-GFP) as previously described (E. I. Fomchenko et al., PloS ONE 6, e20605 (2011).). Nestin-Tv-a; Ink4a/Arf−/− pups were injected with 1 µl of DF-1:RCAS-PDGF-B-GFP cells on post-natal day 2 into the left cortex between the eye and ear.

BLZ945 Inhibitor and Treatment

The CSF-1R inhibitor BLZ945 was formulated in 20% captisol at a concentration of 12.5 mg/ml. The vehicle control, 20% captisol, was processed in the same manner. For BLZ945 studies, mice were dosed with 200 mg/kg BLZ945 or vehicle (20% captisol) by oral gavage once per day.

To determine if the drug was able to cross the blood-brain barrier, tumor-bearing mice were treated with a single dose of BLZ945 and sacrificed at different time points post treatment. Plasma, and the left (contralateral) and right (tumor-bearing) hemispheres of the brain were snap frozen in liquid nitrogen for subsequent analysis of BLZ945 concentrations in the tissue. For long-term survival studies, dosing was begun at 17 days/2.5 weeks post-injection of RCAS-PDGF-B-HA. For the fixed time-point studies, mice underwent MRI scans at 4-5 weeks post-injection of RCAS-PDGF-B-HA, as previously described (Transl Oncol 2, 89 (2009)).

To determine tumor volume, regions of interest (ROI) were circumscribed on T2 weighted images and their corresponding area in $mm^2$ was multiplied by the slice height of 0.7 mm. The total tumor volume is the sum of the ROI volume in each slice, and the volume for the first and last slice in which the tumor appear is halved to approximate the volume of a trapezoid. When tumor volume was in the range of 4.5-40 $mm^3$, animals were randomly assigned to treatment groups. A third cohort of mice with tumors larger than 40 $mm^3$ was also treated with BLZ945 (denoted as BLZ945 Large). A size-matched vehicle treated cohort was not included for this cohort having the larger starting tumor burden because these mice would not have been able to survive to the trial endpoint.

Mouse Sacrifice and Tissue Harvest

Mice were euthanized at defined time points as described in the figure legends or when they became symptomatic from their tumors, which included signs of poor grooming, lethargy, weight loss, hunching, macrocephaly, or seizures.

To isolate tissues for snap freezing in liquid nitrogen, mice were euthanized by carbon dioxide asphyxiation or fully anesthetized with avertin (2,2,2-tribromoethanol, Sigma) and cervically dislocated prior to tissue harvest. For flow cytometry, mice were fully anesthetized with avertin and transcardially perfused with 20 ml of PBS. The brain was then isolated and the tumor macrodissected from the surrounding normal tissue. For proliferation analysis, mice were injected intraperitoneally with 100 mg/g of bromodeoxyuridine (BrdU; Sigma) 2 hours prior to sacrifice. To isolate tissues for frozen histology, mice were fully anesthetized with avertin, transcardially perfused with 10 ml of PBS, followed by 10 ml of 4% paraformaldehyde in PBS (PFA). The brain was postfixed in PFA overnight at 4° C. while other tissues were cryopreserved in 30% sucrose at 4° C. After post-fixation, the brain was then transferred to 30% sucrose and incubated at 4° C. until the brain was fully equilibrated and sank to the bottom of the tube (typically 2 to 3 days). All tissues were then embedded in OCT (Tissue-Tek) and 10 µm cryostat tissue sections were used for all subsequent analysis.

Histology, Immunohistochemistry, and Analysis

For grading of tumor malignancy, hematoxylin and eosin (H&E) staining was performed, and the tissues blindly scored by an independent neuropathologist.

For immunofluorescence, 10 μm thick frozen sections were thawed and dried at room temperature and then washed in PBS. For the standard staining protocol, tissue sections were blocked in 0.5% PNB in PBS for at least 1 hour at room temperature or up to overnight at 4° C., followed by incubation in primary antibody in 0.25% PNB for 2 hours at room temperature or overnight at 4° C. Primary antibody information and dilutions are listed in Table 6. Sections were then washed in PBS and incubated with the appropriate fluorophore-conjugated secondary antibody (Molecular Probes) at a dilution 1:500 in 0.25% PNB for 1 hour at room temperature. After washing in PBS, tissue sections were counterstained with DAPI (5 mg/ml stock diluted 1:5000 in PBS) for 5 minutes prior to mounting with ProLong Gold Antifade mounting media (Invitrogen).

For angiogenesis and proliferation analysis, tissue sections were first subjected to citrate buffer based antigen retrieval by submerging in antigen unmasking solution (0.94% v/v in distilled water; Vector Laboratories) and microwaving for 10 minutes on half power, followed by cooling to room temperature for at least 30 minutes. For angiogenesis analysis, tissues were then washed in PBS and blocked with mouse Ig blocking reagent (Vector Laboratories) according to the manufacturer's instructions for 1 hour at room temperature. For proliferation analysis, after antigen retrieval, tissue sections were incubated with 2M HCl for 15 minutes at room temperature to denature DNA and then in neutralizing 0.1M sodium borate buffer (pH 8.5) for 5 minutes. After PBS washes, the rest of the staining was performed according to the standard protocol.

For staining for phagocytosis analysis, 10 μm thick frozen sections were thawed and dried at room temperature and then washed in PBS. Tissue sections were blocked in 0.5% PNB in PBS for at least 1 hour at room temperature, followed by incubation in rabbit anti-cleaved caspase-3 primary antibody diluted 1:500 in 0.5% PNB overnight at 4° C. The next day, slides were washed 6 times for 5 minutes in PBS prior to incubation with goat-anti-rabbit Alexa568 secondary antibody (1:500 in 0.5% PNB) for 1 hour at room temperature. Tissue sections were then washed 6 times for 5 minutes in PBS and blocked overnight at 4° C. in a new buffer of 5% donkey serum, 3% bovine serum albumin, and 0.5% PNB in PBS. The following day, slides were incubated for 2 hours at room temperature with the next set of primary antibodies: rabbit anti-Olig2 (1:200) and rat anti-CD11b (1:200) diluted in 5% donkey serum, 3% bovine serum albumin, and 0.5% PNB in PBS. Slides were washed 6 times for 5 minutes in PBS prior to incubation with donkey-anti-rabbit Alexa647 (1:500) and donkey-anti-rat Alexa488 (1:500) secondary antibodies in 0.5% PNB for 1 hour at room temperature. Tissue sections were then washed 4 times for 5 minutes in PBS prior to staining with DAPI (5 mg/mL stock diluted 1:5000 in PBS) for 5 minutes, washed twice more in PBS for 5 minutes, and mounted with ProLong Gold Antifade mounting media (Invitrogen). Co-staining for CSF-1R (first primary antibody) and Iba1 (second primary antibody) was also performed in series in the same manner, with the addition of citrate buffer based antigen retrieval at the outset.

Tissue sections were visualized under a Carl Zeiss Axioimager Z1 microscope equipped with an Apotome. The analysis of immunofluorescence staining, cell number, proliferation, apoptosis, and colocalization studies were performed using TissueQuest analysis software (TissueGnostics) as previously described (*Journal Immunol Methods* 237, 39 (2000)).

Overviews of tissue sections from gliomas stained for angiogenesis analysis were generated by TissueGnostics acquisition software by stitching together individual 200× images. All parameters of angiogenesis were quantitated using MetaMorph (Molecular Devices), as previously described (V. Gocheva, et al., *Biol Chem* 391, 937 (2010)).

For analysis of phagocytosis, 15 randomly selected fields of view from within the tumor were acquired using the 63× oil immersion objective (total magnification 630×) and the Apotome to ensure cells were in the same optical section. Positive cells were counted manually using Volocity (PerkinElmer) and were discriminated by the presence of a DAPI+ nucleus. Apoptotic cells were counted as those that had cytoplasmic cleaved caspase-3 (CC3)+ staining and condensed nuclei. A cell was considered to have been engulfed by a macrophage when it was surrounded by a contiguous CD11b+ ring that encircled at least two-thirds of the cell border. The numbers of mice analyzed are specified in the figure legends.

Protein Isolation and Western Blotting

Mice were treated with BLZ945 or vehicle and sacrificed 1 hour following the final dose and tumors were harvested. Samples were biochemically fractionated as described previously. Synaptosomal membrane fractions were lysed in NP-40 lysis buffer (0.5% NP-40, 50 mM Tris-HCl [pH 7.5], 50 mM NaCl, 1× complete Mini protease inhibitor cocktail (Roche), 1× PhosSTOP phosphatase inhibitor cocktail (Roche)) and protein quantified using the BCA assay (Pierce). Protein lysates were loaded (90 μg/lane) onto SDS-PAGE gels and transferred to PVDF membranes for immunoblotting.

Membranes were probed with antibodies against phospho-CSF-1R Y721 (1:1000; Cell Signaling Technology), CSF-1R (1:1000; Santa Cruz Biotechnology), or GAPDH (1:1000; Cell Signaling Technology) and detected using HRP-conjugated anti-rabbit (Jackson Immunoresearch) antibodies using chemiluminescence detection (Millipore). Bands from western blots were quantified in the dynamic range using the Gel analysis module in ImageJ software.

Primary bone marrow derived macrophages (BMDMs) were cultured in the absence of CSF-1 for 12 hours prior to stimulation with CSF-1 (10 ng/ml) for the time points indicated in fig. S2, in the presence or absence of 67 nM BLZ945. Whole protein lysates were isolated with NP40 lysis buffer and detected by western blot as described above.

Preparation of Single Cell Suspensions and Flow Cytometry

For investigation of brain macrophage populations by flow cytometric analysis or sorting, the tumor was digested to a single cell suspension by incubation with 5 ml of papain digestion solution (0.94 mg/ml papain [Worthington], 0.48 mM EDTA, 0.18 mg/ml NAcety-L-cysteine [Sigma], 0.06 mg/ml DNase I [Sigma], diluted in Earl's Balanced Salt Solution and allowed to activate at room temperature for at least 30 minutes). Following digestion, the enzyme was inactivated by the addition of 2 ml of 0.71 mg/ml ovomucoid (Worthington). The cell suspension was then passed through a 40 μm mesh to remove undigested tissue, washed with FACS buffer (1% IgG Free BSA in PBS [Jackson Immunoresearch]), and centrifuged at a low speed of 750 rpm (Sorvall Legend RT), to remove debris and obtain the cell pellet. As many immune cell epitopes are papain-sensitive, for investigation of immune cell infiltration by flow cytometric analysis, tumors were digested to a single cell suspension by incubation for 10 minutes at 37° C. with 5 mL of 1.5 mg/ml collagenase III (Worthington) and 0.06 mg/mL DNase I in 1× Hanks Balanced Salt Solution (HBSS) with calcium and magnesium.

The cell suspension was then washed with PBS and passed through a 40 µm mesh to remove undigested tissue. To remove myelin debris, the cell pellet was resuspended in 15 ml of room temperature 25% Percoll prepared from stock isotonic Percoll (90% Percoll [Sigma], 10% 10×HBSS), and then spun for 15 minutes at 1500 rpm (Sorvall Legend RT) with accelerator and brake set to 1. The cell pellet was then washed with 1×HBSS prior to being resuspended in FACS buffer. After counting, cells were incubated with 1 µl of Fc Block for every million cells for at least 15 minutes at 4° C. Cells were then stained with the appropriate antibodies for 10 minutes at 4° C., washed with FACS buffer, and resuspended in FACS buffer containing DAPI (5 mg/ml diluted 1:5000) for live/dead cell exclusion. Antibodies used for flow cytometry are listed in Table 6.

TABLE 6

List of Antibodies and sources.

| Antibody | Clone | Vendor | Fluorophore(s) | Dilution |
| --- | --- | --- | --- | --- |
| CD45 | 30-F11 | BD Pharmingen | FITC, APC, PE-Cy7 | 1:100-1:200 |
| CD3e | 145-2C11 | BD Pharmingen | PE-Cy7 | 1:250 |
| Gr-1 | RB6-8C5 | BD Pharmingen | FITC | 1:200 |
| CD4 | GK1.5 | BD Pharmingen | PE | 1:1000 |
| CD11b | M1/70 | BD Pharmingen | A488, APC, PE | 1:200 |
| Ly6G | 1A8 | BD Pharmingen | PE-Cy7 | 1:2000 |
| F4/80 | CI:A3-1 | Serotec | PE | 1:50 |
| CD8a | 53-6.7 | Biolegend | A488 | 1:1000 |
| CD19 | 6D5 | Biolegend | PE | 1:2000 |
| NK1.1 | PK136 | Biolegend | APC | 1:1000 |
| CD206 | MR5D3 | Biolegend | A488 | 1:50 |

For analysis, samples were run on a BD LSR II (Becton Dickstein), and all subsequent compensation and gating performed with FlowJo analysis software (TreeStar). For sorting, samples were run on a BD FACSAria (Becton Dickstein) cell sorter and cells were collected into FACS buffer. Cells were then centrifuged and resuspended in 500 µl Trizol (Invitrogen) before snap freezing in liquid nitrogen and storage at −80° C.

Derivation of Mouse Primary Glioma Cultures, Neurospheres and Glioma Cell Lines

Macrodissected tumors were digested to a single cell suspension by incubation for 8-12 minutes at 37° C. as described above. The cell suspension was washed with Neural Stem Cell (NSC) Basal Media (Stem Cell Technologies), and centrifuged at low speed (750 rpm Sorvall Legend RT), to remove debris. To derive primary mouse glioma cultures the cell pellet was resuspended in DMEM containing 10% FBS (Gibco). These primary cultures were used at early passage (P2-P3), and contain a mixture of different cell types found in gliomas including tumor cells, macrophages, and astrocytes as determined by immunofluorescence staining. Primary glioma cultures were grown for 24 hours on poly-L-lysine coated coverslips (BD Biocoat). Cells were then fixed with 4% PFA in 0.1M phosphate buffer overnight at 4° C., permeabilized with 0.1% Triton-X for 5 minutes and blocked with 0.5% PNB for at least one hour. The presence of macrophages, tumor cells and astrocytes were examined by immunofluorescent staining of CD11b (1:200), Nestin (1:500) and GFAP (1:1000), respectively (Table 7).

TABLE 7

List of antibodies used for staining.

| Antibody | Clone | Vendor | Dilution |
| --- | --- | --- | --- |
| Goat anti-mouse CD31 | — | R&D Systms | 1:100 |
| Mouse anti-human smooth muscle actin (SMA) | 1A4 | DakoCytomation | 1:100 |
| Rabbit anti-cleaved caspase 3 (Asp175) (CC3) | — | Cell Signaling Technology | 1:500 |
| Rabbit anti-human CSF-1R | C-20 | Santa Cruz | 1:200 |
| Rabbit anti-Iba1 | — | Wako | 1:1000 |
| Rabbit anti-green fluorescent protein (GFP) | — | Molecular Probes | 1:200 |
| Rabbit anti-Olig2 | — | Millipore/Chemicon | 1:200 |
| Mouse anti-rat Nestin | — | BD Pharmingen | 1:500 |
| Rat anti-mouse CD11b | M1/70 | BD Pharmingen | 1:200 |
| Rat anti-BrdU | BU1/75 (ICR1) | Serotec | 1:200 |
| Rat anti-mouse CD68 | FA-11 | Setotec | 1:1000 |
| Chicken anti-GFAP | — | Abcam | 1:1000 |

For neurosphere formation the cell pellet was resuspended in neurosphere media consisting of mouse NSC Basal Media, NSC proliferation supplements, 10 ng/ml EGF, 20 ng/ml basic-FGF and 1 mg/ml Heparin (Stem Cell Technologies). Fresh media was added every 72 hours for 2 weeks. Primary neurospheres were collected, mechanically disaggregated to a single cell suspension and propagated by serial passaging. To generate glioma cell lines, secondary neurospheres were dissociated to single cell suspensions and cultivated in DMEM+10% FBS as a monolayer. Multiple glioma cell lines were derived from independent mice, denoted GBM1-4 herein. Glioma cells were infected with a pBabe-H2B-mCherry construct as described previously (O. Florey, et al., Nat Cell Biol 13, 1335 (2011)).

Isolation of Bone Marrow-Derived Macrophages (BMDMs)

For bone marrow isolation, followed by macrophage derivation, C57BL/6 WT, C57BL/6 β-actin-GFP or Nestin-Tv-a; Ink4a/Arf−/− mice were anesthetized with Avertin (Sigma) and then sacrificed via cervical dislocation. Femurs and tibiae were harvested under sterile conditions from both legs and flushed. The marrow was passed through a 40 µm strainer and cultured in 30 ml Teflon® bags (PermaLife PL-30) with 10 ng/ml recombinant mouse CSF-1 (R&D Systems). Bone marrow cells were cultured in Teflon® bags for 7 days, with fresh CSF-1-containing media replacing old media every other day to induce macrophage differentiation.

Additional cell lines U-87 MG (HTB-14) glioma and CRL-2467 microglia cell lines were purchased from the ATCC. The U-87 MG cell line was cultured in DMEM+10% FBS. The CRL-2467 cell line was cultured in DMEM+10% FBS with 30 ng/ml recombinant mouse CSF-1.

Glioma cell-conditioned media (GCM) experiments Media that had been conditioned by glioma tumor cell lines grown in serum free media for 24 hours was passed through 0.22 µm filters to remove cellular debris, and is referred to herein as glioma cell-conditioned media (GCM). GCM was used to stimulate differentiated C57BL/6 WT or β-actin-GFP+ BMDMs. Control macrophages received fresh media containing 10% FBS and 10 ng/ml recombinant mouse CSF-1. When indicated, differentiated BMDMs were cultivated in GCM containing either DMSO as vehicle, or 67 nM BLZ945, 670 nM BLZ945, or in regular media containing 10 ng/ml mouse recombinant CSF-1 and 10 ng/ml IL-4 (R&D Systems) for 24 hours or 48 hours prior to experimental analysis.

Analysis of Mrc1/CD206 Expression by Flow Cytometry

For mouse primary glioma cultures (containing a mixed population of tumor cells, TAMs, astrocytes etc.), 1×106 cells were cultivated in DMEM+10% FBS in the presence of BLZ945 or DMSO as vehicle. For BMDMs, $1 \times 10^6$ cells were cultivated in DMEM supplemented with recombinant mouse CSF-1 or GCM in the presence of BLZ945 or DMSO as vehicle. After 48 hours, cells were scraped and washed with FACS buffer. Cells were counted and incubated with 1 µl of Fc Block (BD Pharmingen) per 106 cells for at least 15 minutes at 4° C. Cells were then stained with CD45 and CD11b antibodies for 10 minutes at 4° C. and washed with FACS buffer. Cells were fixed and permeabilized using the BD Cytofix/Cytoperm™ kit (BD Biosciences) according to the manufacturer's instructions. Subsequently cells were stained with anti-CD206 antibody. For analysis, samples were run on a BD LSR II (Becton Dickstein), and all subsequent compensation and gating performed with FlowJo analysis software (TreeStar).

Cell Cycle Analysis

Control or GCM pre-stimulated macrophages derived from β-actin-GFP+ mice were cocultured in a 1:1 ratio with 1×105 serum starved mCherry-positive glioma cells (from the cell lines derived above) for 48 hours in the presence of 670 nM BLZ945 or DMSO as vehicle. Following collection of trypsinized co-cultured cells, wells were rinsed in additional media and this volume was collected to ensure harvesting of all macrophages, which adhered tightly to cell culture dishes. Samples were then washed once with FACS buffer, followed by incubation for 10 minutes at room temperature in permeabilizing buffer (10 mM PIPES, 0.1 M NaCl, 2 mM MgCl2, 0.1% Triton X-100, pH 6.8) containing 0.1 mg DAPI (Invitrogen). After acquisition on an LSR II flow cytometer (BD) using a UV laser (350-360 nm), cell cycle status of glioma tumor cells was analyzed using the Flow Jo Dean-Jett-Fox program for cell cycle analysis.

Proliferation Assays

Cell growth rate was determined using the MTT cell proliferation kit (Roche). Briefly, cells were plated in triplicate in 96-well plates ($1 \times 10^3$ cells/well for glioma cell lines and $5 \times 10^3$ cells/well for BMDM and CRL-2467 cells) in the presence or absence of 6.7-6700 nM of BLZ945. Media was changed every 48 hours. BMDM and CRL-2467 cells were supplemented with 10 ng/ml and 30 ng/ml recombinant mouse CSF-1 respectively unless otherwise indicated. 10 µl of MTT labeling reagent was added to each well and then incubated for 4 hours at 37° C., followed by the addition of 100 µl MTT solubilization reagent overnight. The mixture was gently resuspended and absorbance was measured at 595 nm and 750 nm on a spectraMax 340pc plate reader (Molecular Devices).

Secondary Neurosphere Formation Assay

Primary neurospheres were disaggregated to a single cell suspension and $5 \times 10^3$ cells were plated in a 6 well plate in neurosphere media in the presence of BLZ945 or DMSO as vehicle. Media was changed every 48 hours. Secondary neurosphere formation was assayed by counting the number of neurospheres obtained after 2 weeks.

RNA Isolation, cDNA Synthesis and Quantitative Real Time PCR

RNA was isolated with Trizol, DNase treated, and 0.5 µg of RNA was used for cDNA synthesis. Taqman probes (Applied Biosystems) for Cd11b (Mm00434455_m1), Cd68 (Mm03047343_m1), Csf-1 (Mm00432688_m1), Csf-1r (Mm00432689_m1), Il34 (Mm00712774_m1), Mrc1 (Mm00485148_m1), and Tv-a (custom), were used for qPCR. Assays were run in triplicate and expression was normalized to ubiquitin C (Mm01201237_m1) for each sample.

Microarrays and Gene Expression Profiling

All samples were prepared and processed by the genomics core facility at MSKCC. RNA was isolated using Trizol and the quality was assessed by running on an Agilent Bioanalyzer. 75 ng of total RNA was reverse transcribed and labeled using the Genechip 3' IVT Express Kit (Affymetrix). The resulting cRNA was hybridized to Affymetrix MOE 430A 2.0 chips. Raw expression data were analyzed using GCOS 1.4 (Affymetrix). Data were normalized to a target intensity of 500 to account for differences in global chip intensity.

Microarray Analysis

All bioinformatic analyses were completed in R using the Bioconductor Suite of packages. Robust Multi-Array Average (RMA) expression values were generated using the 'affy' package and quantile normalized (R. A. Irizarry et al., *Nucleic Acids Res* 31, e15 (2003); L. Gautier, et al., *Bioinformatics* 20, 307 (2004). The 'limma' package (G. K. Smyth, *Statistical Applications in Genetics and Molecular Biology* 3, Article 3 (2004)) was used to identify differentially expressed genes between the vehicle and BLZ945 treated samples. Differential expression was considered significant at a fold change of +/−2 with a false discovery rate of 10%. Gene set enrichment analysis (GSEA) was used as described previously (15). For subsequent analysis and comparison to human datasets, mouse expression values were mean centered across all samples.

Lasso Regression Method for Gene Signature Identification

Mouse expression data was normalized and mean centered as described above. Differentially expressed genes were used for further analysis. A Lasso regression model was trained to differentiate between Vehicle and BLZ945 treated samples using the 'glmnet' package (J. Friedman, et al., *Journal of Statistical Software* 33, 1 (2010).). The regularization parameter for Lasso regression was chosen by 4-fold cross validation.

Patient Datasets

TCGA expression data was downloaded from the TCGA data portal and all clinical data was downloaded from the data portal ≤http://tcga-data.nci.nih.gov/tcga/tcgaHome2.jsp>. Clinical and expression data for the Rembrandt data set was downloaded from <https://caintegrator.nci.nih.gov/rembrandt/>. The Freije (GSE4412), Murat (GSE7696), and Phillips (GSE4271) datasets were downloaded from the NCBI <http://www.ncbi.nlm.nih.gov/geo/>. For the Freije datasets, only samples that were run on the HGU133A platform were considered, as samples on the HGU133B platform contained minimal overlap with the remaining datasets. Each data set was imported separately using the 'Affy' package and RMA expression values were generated. All data sets were quantile normalized and each gene was mean centered across all patients.

Subtyping of Non TCGA Patients

To investigate subtype specific survival differences in all publically available datasets, a subtype classifier described previously (R. G. Verhaak et al., *Cancer Cell* 17, 98 (2010)) was utilized to train a support vector machine (SVM). The 840 genes used by Verhaak and colleagues for the ClacNc analysis were used to subset the dataset. Subsequently, data sets were subsetted for genes that were called present across all patient data sets described above. The remaining 776 genes were used to train a multiclass SVM on the Core samples from the TCGA dataset. The SVM was completed using a Gaussian radial basis kernel function using the 'kernlab' package (A. Karatzoglou, et al., *J. Statistical Software*, 11, 9 (2004)). This SVM was then used to predict the subtype of the remainder of the TCGA patients and public datasets.

Patient Classification

A SVM was trained on mouse expression data to classify patients into "Vehicle" classification or "BLZ945" classification. Patient expression data was subsetted for common genes across all data sets and genes that have known mouse homologues. Similarly, mouse expression data was subsetted for genes with human homologues that were common across all patient samples. Subsequently, mouse data was subsetted for differentially expressed genes identified using the 'limma' package. Human data was subsetted for the human homologues of these differentially expressed genes. This led to a feature reduction from 257 differentially expressed genes to 206 differentially expressed genes with known human homologues across all patient datasets. The 'kernlab' package was then used to train a SVM on the mouse expression data using a vanilla kernel function. This SVM was then used to predict patients into either "Vehicle" classifier or "BLZ945" classifier.

A similar approach was used to classify patients with a Lasso regression model. The subsetting of patient and mouse data was identical to that described above. Instead of using the 'kernlab' package, the Lasso regression model was trained using the 'glmnet' package. This model was then used to predict patient classification into either "Vehicle" classifier or "BLZ945" classifier. G-CIMP patient status was determined by hierarchical clustering of patient methylation data (H. Noushmehr et al., *Cancer Cell* 17, 510 (2010)) as described below.

Stratification of Patients by G-CIMP Status

Experimentally, it appears that the survival advantage offered by the "BLZ945" treatment signature was not due to an enrichment of Glioma CpG Island Methylator Phenotype (GCIMP) patients, which have previously been shown to be associated with improved overall survival (Noushmehr). Of the 453 GBMs analyzed from the TCGA dataset, 263 also had genomic methylation data and were classified into the methylation clusters as described previously. Of the 21 G-CIMP patients, 20 (95%) were classified into the "BLZ945" classification, showing a strong enrichment of BLZ945 samples in the G-CIMP patients. Despite this enrichment, survival analysis of Proneural patients known to be GCIMP negative (67/133 total Proneural patients) revealed that the "BLZ945" classification group still showed an increase in survival of ~10.8 months (P=0.014).

Moreover, cox proportional hazard models demonstrated that the increase in survival demonstrated by "BLZ945" classification was not dependent upon G-CIMP patients. The hazard ratio associated with the BLZ945 signature was significant with and without G-CIMP patients. Also, the hazard ratio for G-CIMP strata was not significant when the BLZ945 signature was also considered in a mixed model. Thus, although the G-CIMP patients are clearly enriched for mock "BLZ945" classification samples, the survival benefit offered by this classification is not dependent upon GCIMP status.

Survival Analysis

Survival analysis was completed using the 'survival' package in R (T. Therneau, in R package version 2.36-12. (2012)). Hazard ratios were determined utilizing the 'coxph' function from the 'survival' package. Patients were stratified based on the probability of the Lasso regression classification model, G-CIMP status, or both as indicated. P values were generated using Wald's test.

Plots for Patient Analyses

All Kaplan-Meier survival curves, heatmaps and volcano plots were generated in R v 2.14.1 using the 'gplots' package (G. R. Warnes et al., R package version 2.10.1, (2011).). Hazard ratio forest plots were generated in GraphPad Prism ProS.

Data Presentation and Statistical Analysis

Data are presented as means with their respective standard error (SEM) or as statistical scatter plots using GraphPad Prism ProS. Numeric data were analyzed by unpaired twotailed Student's t-test unless otherwise noted. For survival curves, P values were obtained using Log Rank (Mantel-Cox) test, and Fisher's exact test was used for histological tumor grading. P=0.05 was considered as statistically significant.

The invention claimed is:

1. A method of treating glioblastoma multiforme in a human subject having glioblastoma multiforme, said method comprising administering to the subject an effective amount of a CSF-1 R kinase inhibitor compound of formula:

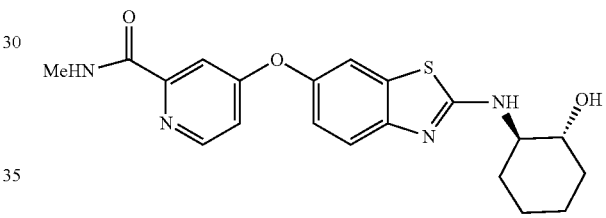

or a pharmaceutically acceptable salt thereof.

2. The method of claim 1, wherein the compound is a pharmaceutically acceptable salt.

3. The method of claim 1, wherein the method further comprises the step of: administering to the subject an effective amount of an additional cancer therapeutic selected from bevacizumab with or without irinotecan, a nitrosourea, a platin, an alkylating agent, a tyrosine kinase inhibitor, Ukrain, and a cannabinoid.

4. The method of claim 1, wherein the compound or pharmaceutically acceptable salt thereof is administered orally.

5. The method of claim 1, wherein the compound or pharmaceutically salt thereof is administered to the subject in an amount between about 10 mg/kg per day to about 500 mg/kg per day.

6. The method of claim 1, wherein the compound or pharmaceutically salt thereof is administered to the subject in one or two oral doses per day.

7. The method of claim 3 wherein the additional cancer therapeutic is an alkylating agent.

8. The method of claim 7 wherein the alkylating agent is temozolomide.

* * * * *